United States Patent
Kodama

(10) Patent No.: US 7,202,014 B2
(45) Date of Patent: Apr. 10, 2007

(54) STIMULUS-SENSITIVE COMPOSITION, COMPOUND AND PATTERN FORMATION METHOD USING THE STIMULATION-SENSITIVE COMPOSITION

(75) Inventor: Kunihiko Kodama, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 85 days.

(21) Appl. No.: 10/893,345

(22) Filed: Jul. 19, 2004

(65) Prior Publication Data

US 2005/0019689 A1   Jan. 27, 2005

(30) Foreign Application Priority Data

Jul. 22, 2003  (JP) ............ P.2003-277359
Feb. 5, 2004   (JP) ............ P.2004-028944

(51) Int. Cl.
  G03C 1/73  (2006.01)
  G03F 7/038 (2006.01)
  G03F 7/039 (2006.01)
  G03F 7/20  (2006.01)
  G03F 7/30  (2006.01)
  C07C 381/12 (2006.01)

(52) U.S. Cl. ............ 430/270.1; 430/921; 430/325; 430/326; 430/907; 568/75

(58) Field of Classification Search ............ None
See application file for complete search history.

(56) References Cited

U.S. PATENT DOCUMENTS 6,093,753 A * 7/2000 Takahashi ............ 522/25
2003/0215739 A1 * 11/2003 Harada et al. ........... 430/270.1
2004/0185378 A1 * 9/2004 Kodama et al. ........... 430/311

FOREIGN PATENT DOCUMENTS

| EP | 1 353 225 A2 | 10/2003 |
| JP | 2000-292917 A | 10/2000 |
| JP | 2001-187780 | * 7/2001 |
| JP | 2001-294570 A | 10/2001 |
| JP | 2002-236358 | * 8/2002 |
| JP | 2002-255930 A | 9/2002 |
| JP | 2002-265512 | * 9/2002 |

OTHER PUBLICATIONS

JPO English abstract for JP 2002-255930 (AOSO et al), provided by Japan Patent Office.*
Machine-assisted English translation of JP 2002-236358 (Kodama et al) provided by JPO.*
Machine-asssited English translation of JP 2001-187780 (Iwasa et al) provided by JPO.*
Machine-assisted English translation of JP 2002-265512 (Uesugi et al) provided by JPO.*
European Search Report dated Nov. 22, 2004.

* cited by examiner

*Primary Examiner*—Sin Lee
(74) *Attorney, Agent, or Firm*—Sughrue Mion, PLLC

(57) ABSTRACT

A stimulus-sensitive composition comprising a compound (A) that generates one of an acid and a radical by external stimulation, the compound (A) having a specific structure.

14 Claims, No Drawings

STIMULUS-SENSITIVE COMPOSITION, COMPOUND AND PATTERN FORMATION METHOD USING THE STIMULATION-SENSITIVE COMPOSITION

BACKGROUND OF THE INVENTION

1. Field of the Invention

The present invention relates to a stimulus-sensitive composition for use in the production process of a semiconductor such as IC, in the production of a circuit substrate of liquid crystal, thermal head and the like, in other photofabrication processes or in the lithographic printing plate, acid-curable composition, radical-curable composition and the like, and also relates to a compound for use in the stimulus-sensitive composition and a pattern forming method using the stimulus-sensitive composition.

2. Description of the Related Art

The stimulus-sensitive composition is a composition of generating an acid or a radical by external stimulation and causing change in the physical properties in the portion stimulated by the reaction of the acid or radical, and this is more preferably a pattern-forming material of forming a pattern on a substrate by causing change in the solubility in a developer between the part irradiated with actinic rays, radiation or heat and the non-irradiated part.

In such a stimulus-sensitive composition, various acid generators of generating an acid upon irradiation with actinic rays or radiation have been proposed.

For example, JP-A-2000-292917 (the term "JP-A" as used herein means an "unexamined published Japanese patent application") describes a resist composition using a mixture of a triarylsulfonium salt and a phenacylsulfonium salt, and JP-A-2001-294570 describes a resist composition containing a phenacylsulfonium salt having a ring structure.

However, conventional resist compositions are being demanded to be more improved in the sensitivity and profile.

SUMMARY OF THE INVENTION

Accordingly, an object of the present invention is to provide a stimulus-sensitive composition exhibiting high sensitivity and good profile, a photosensitive composition exhibiting high sensitivity and good profile at an exposure wavelength of 200 nm or less, particularly, at the exposure to ArF excimer laser light (193 nm) or $F_2$ excimer laser light (157 nm), a novel compound of generating an acid or a radical by external stimulation, which is used in these compositions, and a pattern forming method using such a composition.

The present invention has the following constitutions and by these constitutions, the object of the present invention can be attained.

(1) A stimulus-sensitive composition comprising a compound that generates one of an acid and a radical by external stimulation, the compound being represented by formula (I):

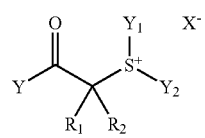

(I)

wherein

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$), $R_1$ and $R_2$ each independently represents a hydrogen atom, an alkyl group, a cycloalkyl group, an aryl group, the —C(=O)—$Y_{3a}$ group or the —$Y_{3b}$—C(=O)—$Y_{3c}$ group, and $R_1$ and $R_2$ may combine to form a ring, $Y_1$ and $Y_2$ each independently represents an alkyl group, a cycloalkyl group, an aryl group, the —C(=O)—$Y_{3a}$ group or the —$Y_{3b}$—C(=O)—$Y_{3c}$ group, and $Y_1$ and $Y_2$ may combine to form a ring, Y and $R_1$ may combine to form a ring, provided that (i) at least one of Y, $Y_1$, $Y_2$, $R_1$ and $R_2$ is the —C(=O)—$Y_{3a}$ group or the —$Y_{3b}$—C(=O)—$Y_{3c}$ group, or (ii) at least one of the ring formed by the combining of $R_1$ and $R_2$, the ring formed by the combining of $Y_1$ and $Y_2$, the ring formed by the combining of Y and $R_1$, Y, $Y_1$, $Y_2$, $R_1$ and $R_2$ contains the —C(=O)—$Y_{3a}$ group or the —$Y_{3b}$—C(=O)—$Y_{3c}$ group, and $X^-$ represents a non-nucleophilic anion.

(2) The stimulus-sensitive composition as described in (1), wherein the compound represented by formula (I) is represented by formula (I'):

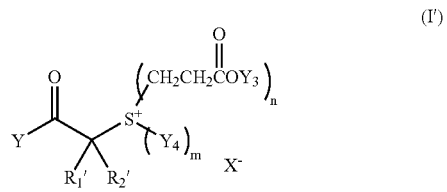

(I')

wherein

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$), $R_1'$ and $R_2'$ each independently represents a hydrogen atom, an alkyl group or a cycloalkyl group, $Y_3$ and $Y_4$ each independently represents an alkyl group or a cycloalkyl group, $X^-$ represents a non-nucleophilic anion, m represents 0 or 1, and n represents 1 or 2, provided that m+n=2.

(3) A compound represented by formula (I):

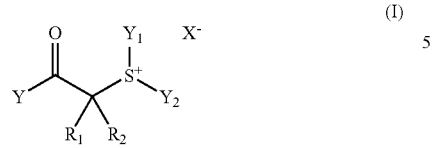

wherein

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$), $R_1$ and $R_2$ each independently represents a hydrogen atom, an alkyl group, a cycloalkyl group, an aryl group, the —C(=O)—$Y_{3a}$ group or the —$Y_{3b}$—C(=O)—$Y_{3c}$ group, and $R_1$ and $R_2$ may combine to form a ring, $Y_1$ and $Y_2$ each independently represents an alkyl group, a cycloalkyl group, an aryl group, the —C(=O)—$Y_{3a}$ group or the —$Y_{3b}$—C(=O)—$Y_{3c}$ group, and $Y_1$ and $Y_2$ may combine to form a ring, Y and $R_1$ may combine to form a ring, provided that (i) at least one of Y, $Y_1$, $Y_2$, $R_1$ and $R_2$ is the —C(=O)—$Y_{3a}$ group or the —$Y_{3b}$—C(=O)—$Y_{3c}$ group, or (ii) at least one of the ring formed by the combining of $R_1$ and $R_2$, the ring formed by the combining of $Y_1$ and $Y_2$, the ring formed by the combining of Y and $R_1$, Y, $Y_1$, $Y_2$, $R_1$ and $R_2$ contains the —C(=O)—$Y_{3a}$ group or the —$Y_{3b}$—C(=O)—$Y_{3c}$ group, and $X^-$ represents a non-nucleophilic anion.

(4) A compound represented by the following formula (I'):

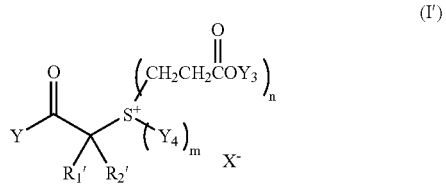

wherein

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$), $R_1'$ and $R_2'$ each independently represents a hydrogen atom, an alkyl group or a cycloalkyl group, $Y_3$ and $Y_4$ each independently represents an alkyl group or a cycloalkyl group, $X^-$ represents a non-nucleophilic anion, m represents 0 or 1, and n represents 1 or 2, provided that m+n=2.

(5) A pattern forming method comprising: forming a resist film by using the stimulus-sensitive composition described in (1) or (2); and exposing and developing the resist film.

Preferred embodiments of the present invention are as follows.

(6) A positive stimulus-sensitive composition comprising:

(A) a compound that generates an acid upon irradiation with an actinic ray, represented by formula (I); and (B) a resin that increases a solubility of the resin in an alkali developer by an action of an acid.

(7) The positive stimulus-sensitive composition as described in (6) above, wherein the resin (B) has a fluorine atom in the main or side chain.

(8) The positive stimulus-sensitive composition as described in (6) above, wherein the resin (B) has a hexafluoro-isopropanol structure.

(9) The positive stimulus-sensitive composition as described in (6) above, wherein the resin (B) has a hydroxystyrene structure.

(10) The positive stimulus-sensitive composition as described in (6) above, wherein the resin (B) has a monocyclic or polycyclic alicyclic hydrocarbon structure.

(11) The positive stimulus-sensitive composition as described in (10) above, wherein the resin (B) further has a lactone structure.

(12) The positive stimulus-sensitive composition as described in any one of (6) to (10) above, further comprising (C) a dissolution inhibiting compound that increases a solubility of the compound (C) by an action of acid, the compound (C) having a molecular weight of 3,000 or less.

(13) A positive stimulus-sensitive composition comprising:

(A) a compound that generates an acid upon irradiation with an actinic ray, represented by formula (I);

(D) a resin soluble in an alkali developer; and (C) a dissolution inhibiting compound that increases a solubility of the compound (C) by an action of an acid, the compound (C) having a molecular weight of 3,000 or less.

(14) A negative stimulus-sensitive composition comprising:

(A) a compound that generates an acid upon irradiation with an actinic ray, represented by formula (I);

(D) a resin soluble in an alkali developer; and (E) an acid crosslinking agent that cross-links with the alkali developer-soluble resin by an action of an acid.

(15) The stimulus-sensitive composition as described in any one of (1) to (2) and (6) to (14), further comprising at least one of (F) a basic compound and (G) a surfactant containing at least one of a fluorine and a silicon. (16) The stimulus-sensitive composition as described in (15), wherein (F) the basic compound is one of (i) a compound having a structure selected from an imidazole structure, a diazabicyclo structure, an onium hydroxide structure, an onium carboxylate structure, a trialkylamine structure, an aniline structure and a pyridine structure, (ii) an alkylamine derivative having at least one of a hydroxyl group and an ether bond, and (iii) an aniline derivative having at least one of a hydroxyl group and an ether bond.

DETAILED DESCRIPTION OF THE INVENTION

The present invention is described in detail below.

In the present invention, when a group (atomic group) is denoted without specifying "substituted or unsubstituted", the group includes a group having no substituent and a group having a substituent. For example, "an alkyl group" includes not only an alkyl group having no substituent (unsubstituted alkyl group) but also an alkyl group having a substituent (substituted alkyl group).

The stimulus-sensitive composition of the present invention comprises a compound that generates an acid or a radical by external stimulation, which is represented by formula (I) (hereinafter sometimes referred to as a "compound (A)").

The stimulus-sensitive composition of the present invention preferably includes a photosensitive or heat-sensitive composition, more specifically, a positive or negative photosensitive or heat-sensitive composition.

The positive photosensitive or heat-sensitive composition, preferably positive resist composition, of the present invention comprises (A) a compound that generates an acid upon irradiation with an actinic ray and (B) a resin that increases a solubility of the resin in an alkali developer by an action of an acid (that is, a resin that decomposes under the action of an acid to increase the solubility in an alkali developer) and if desired, further comprises (C) a dissolution inhibiting compound that increases a solubility of the compound (C) by an action of an acid, the compound (C) having a molecular weight of 3,000 or less (that is, a resin that decomposes under the action of an acid to increase the solubility in an alkali developer and having a molecular weight of 3,000 or less), or the composition comprises (A) a compound that generates an acid upon irradiation with an actinic ray, (D) a resin soluble in an alkali developer and (C) a dissolution inhibiting compound that increases a solubility of the compound (C) by an action of an acid, the compound (C) having a molecular weight of 3,000 or less.

The negative photosensitive or heat-sensitive composition, preferably negative resist composition, of the present invention comprises (A) a compound that generates an acid upon irradiation with an actinic ray, (D) a resin soluble in an alkali developer and (E) an acid crosslinking agent that cross-links with the alkali developer-soluble resin by an action of an acid.

[1] (A) Compound that Generates an Acid or a Radical by External Stimulation, Represented by Formula (I)

The compound of generating an acid or a radical by external stimulation is a compound of generating an acid or a radical by external stimulation such as an actinic ray (e.g., radiation, infrared light, visible light, ultraviolet light, far ultraviolet light, X ray, electron beam), heat and ultrasonic wave.

In the present invention, a compound represented by formula (I) is used as the compound that generates an acid or a radical by external stimulation.

In formula (I),

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$), $R_1$ and $R_2$ each independently represents a hydrogen atom, an alkyl group, a cycloalkyl group, an aryl group, the —C(=O)—$Y_{3a}$ group or the —$Y_{3b}$—C(=O)—$Y_{3c}$ group, and $R_1$ and $R_2$ may combine to form a ring, $Y_1$ and $Y_2$ each independently represents an alkyl group, a cycloalkyl group, an aryl group, the —C(=O)—$Y_{3a}$ group or the —$Y_{3b}$—C(=O)—$Y_{3c}$ group, and $Y_1$ and $Y_2$ may combine to form a ring, Y and $R_1$ may combine to form a ring, provided that at least one of Y, $Y_1$, $Y_2$, $R_1$ and $R_2$ is the —C(=O)—$Y_{3a}$ group or the —$Y_{3b}$—C(=O)—$Y_{3c}$ group, or at least one of the ring formed by the combining of $R_1$ and $R_2$, the ring formed by the combining of $Y_1$ and $Y_2$, the ring formed by the combining of Y and $R_1$, Y, $Y_1$, $Y_2$, $R_1$ and $R_2$ contains the —C(=O)—$Y_{3a}$ group or the —$Y_{3b}$—C(=O)—$Y_{3c}$ group, and $X^-$ represents a non-nucleophilic anion.

In formula (I), the aryl group of Y is preferably an aryl group having from 6 to 14 carbon atoms, such as phenyl group, naphthyl group and anthryl group.

The alkyl group of Y is preferably a linear or branched alkyl group having from 1 to 30 carbon atoms, such as methyl group, ethyl group, propyl group, isopropyl group, n-butyl group, isobutyl group, sec-butyl group, pentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and eicosyl group.

The cycloalkyl group of Y is preferably a monocyclic or polycyclic cycloalkyl group having from 3 to 30 carbon, such as cyclopropyl group, cyclopentyl group, cyclohexyl group, adamantyl group, norbornyl group and boronyl group.

The alkenyl group of Y is preferably an alkenyl group having from 2 to 6 carbon atoms, such as vinyl group, propenyl group, allyl group, butenyl group, pentenyl group, hexenyl group, cyclopentenyl group, cyclohexenyl group, 3-oxocyclohexenyl group, 3-oxocyclopentenyl group and 3-oxoindenyl group.

These aryl group, alkyl group, cycloalkyl group and alkenyl group of Y each includes a group not having a substituent and a group having a substituent. Examples of the substituent for the aryl group, alkyl group, cycloalkyl group and alkenyl group of Y include a nitro group, a halogen atom (e.g., fluorine, chlorine, bromine, iodine), a hydroxyl group, an amino group, a cyano group, an alkoxy group (preferably having from 1 to 5 carbon atoms), an acyl group (preferably having from 2 to 12 carbon atoms), an alkoxycarbonyloxy group (preferably having from 2 to 7 carbon atoms), a di(alkoxycarbonylalkyl)thio group (preferably having from 4 to 20 carbon atoms), a di(alkoxycarbonylalkyl)thioalkylcarbonyl group (preferably having from 6 to 22 carbon atoms), the —C(=O)—$Y_{3a}$ group described above, and the —$Y_{3b}$—C(=O)—$Y_{3c}$ group described above. Furthermore, examples of the substituent for the aryl group of Y include the above-described alkyl groups and cycloalkyl groups, examples of the substituent for the alkyl group of Y include the above-described aryl groups and cycloalkyl groups, and examples of the substituent for the cycloalkyl group of Y include the above-described aryl groups and alkyl groups.

The alkyl group of $R_1$, $R_2$, $Y_1$ and $Y_2$ may have a substituent and may be linear or branched, and the alkyl group is, for example, a linear or branched alkyl group having from 1 to 20 carbon atoms, preferably a linear or branched alkyl group having from 1 to 12 carbon atoms, such as methyl group, ethyl group, linear or branched propyl group, linear or branched butyl group and linear or branched pentyl group. The alkyl group of $R_1$, $R_2$, $Y_1$ and $Y_2$ may have an ether linking group.

The cycloalkyl group of $R_1$, $R_2$, $Y_1$ and $Y_2$ may have a substituent and the cycloalkyl group is, for example, a cycloalkyl group having from 3 to 20 carbon atoms, preferably a cycloalkyl group having from 3 to 8 carbon atoms, such as cyclopentyl group and cyclohexyl group. The cycloalkyl group of $R_1$, $R_2$, $Y_1$ and $Y_2$ may have an ether linking group.

The aryl group of $R_1$, $R_2$, $Y_1$ and $Y_2$ may have a substituent and the aryl group is preferably an aryl group having from 6 to 14 carbon atoms, such as phenyl group, naphthyl group and anthryl group, and more preferably a phenyl group or a naphthyl group.

$R_1$ and $R_2$ may combine to form a ring.

$Y_1$ and $Y_2$ may combine to form a ring together with $S^+$ in formula (I).

Y and $R_1$ may combine to form a ring.

The group formed by the combining of $R_1$ and $R_2$, $Y_1$ and $Y_2$, or Y and $R_1$ is, for example, an alkylene group having from 2 to 10 carbon atoms, preferably a butylene group, a pentylene group or a hexylene group, more preferably a butylene group or a pentylene group. The ring formed may contain a double bond or a heteroatom.

These aryl group, alkyl group, cycloalkyl group and ring structure formed by the combining of $R_1$ and $R_2$, $Y_1$ and $Y_2$, or Y and $R_1$ each may or may not have a substituent. Examples of the substituent include a nitro group, a halogen atom (e.g., fluorine, chlorine, bromine, iodine), a hydroxyl group, an amino group, a cyano group, an alkoxy group (preferably having from 1 to 5 carbon atoms), an aryl group (preferably having from 6 to 14 carbon atoms), a cycloalkyl group (preferably having from 3 to 20 carbon atoms), an acyl group (preferably having from 2 to 12 carbon atoms), an alkoxycarbonyloxy group (preferably having from 2 to 7 carbon atoms), the —C(=O)—$Y_{3a}$ group described above, and the —$Y_{3b}$—C(=O)—$Y_{3c}$ group described above. Furthermore, examples of the substituent for the aryl group, cycloalkyl group and ring structure in each group include an alkyl group (preferably having from 1 to 20 carbon atoms).

In formula (I), at least one of Y, $Y_1$, $Y_2$, $R_1$ and $R_2$ is the —C(=O)—$Y_{3a}$ group or —$Y_{3b}$—C(=O)—$Y_{3c}$ group, or at least one of the ring formed by the combining of $R_1$ and $R_2$, the ring formed by the combining of $Y_1$ and $Y_2$, the ring formed by the combining of Y and $R_1$, Y, $Y_1$, $Y_2$, $R_1$ and $R_2$ contains the —C(=O)—$Y_{3a}$ group or —$Y_{3b}$—C(=O)—$Y_{3c}$ group. In these formulae, $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from the $Y_{3a}$.

The alkyl group of $Y_{3a}$, $Y_{3c}$, $R_3$ and $R_4$ is preferably a linear or branched alkyl group having from 1 to 30 carbon atoms, such as methyl group, ethyl group, propyl group, isopropyl group, n-butyl group, isobutyl group, sec-butyl group, pentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and eicosyl group.

The cycloalkyl group of $Y_{3a}$, $Y_{3c}$, $R_3$ and $R_4$ is preferably a cycloalkyl group having from 3 to 30 carbon, such as cyclopropyl group, cyclopentyl group, cyclohexyl group, adamantyl group, norbornyl group and boronyl group.

The aryl group of $Y_{3a}$ and $Y_{3c}$ is preferably an aryl group having from 6 to 16 carbon atoms, such as phenyl group, naphthyl group and anthryl group.

The alkenyl group of $Y_{3a}$ and $Y_{3c}$ is preferably an alkenyl group having from 2 to 6 carbon atoms, such as vinyl group, propenyl group, allyl group, butenyl group, pentenyl group, hexenyl group, cyclopentenyl group, cyclohexenyl group, 3-oxocyclohexenyl group, 3-oxocyclopentenyl group and 3-oxoindenyl group.

The alkoxy group of $Y_{3a}$ and $Y_{3c}$ is preferably an alkoxy group having from 1 to 30 carbon atoms, such as methoxy group, ethoxy group, propoxy group, butoxy group, pentyloxy group, hexyloxy group, heptyloxy group, octyloxy group, nonyloxy group, decyloxy group, undecyloxy group, dodecyloxy group, tridecyloxy group, tetradecyloxy group, pentadecyloxy group, hexadecyloxy group, heptadecyloxy group, octadecyloxy group, nonadecyloxy group, eicosyloxy group, cyclopropoxy group, cyclobutoxy group, cyclopentyloxy group, cyclohexyloxy group, norbornyloxy group, menthyloxy group and adamantyloxy group.

The aryloxy group of $Y_{3a}$ and $Y_{3c}$ is preferably an aryloxy group having from 6 to 16 carbon atoms, such as phenyloxy group, naphthyloxy group and anthryloxy group.

The divalent linking group of $Y_{3b}$ is a divalent linking group resulting from removal of one hydrogen atom from the above-described $Y_{3a}$, for example, a divalent linking group resulting from removal of one hydrogen atom from the alkyl group, the aryl group, the alkyl group in the alkoxy group, the aryl group in the aryloxy group, the hydroxyl group, the —$NR_3R_4$ group, the —NHCO—$R_3$ group or the —$NHSO_2R_3$ group of $Y_{3a}$.

$Y_1$ and $Y_2$ each is preferably a —$(CH_2)_{n1}C(=O)OY_{3a1}$ group, whereby good profile is obtained and furthermore, development defects can be reduced. In the formula, $Y_{3a1}$ represents an alkyl group (preferably having from 1 to 30 carbon atoms) or a cycloalkyl group (preferably having from 3 to 30 carbon atoms), and n1 is a number of 1 to 10 (preferably from 2 to 6, more preferably from 2 to 4, still more preferably 2). These alkyl group and cycloalkyl group of $Y_{3a1}$ may be substituted by a fluorine atom or the like. $Y_{3a1}$ is preferably an alkyl group having from 1 to 20 carbon atoms or a fluoroalkyl group having from 1 to 20 carbon atoms, more preferably a partially fluorinated fluoroalkyl group having from 1 to 20 carbon atoms, and most preferably a group represented by —$(CH_2)_k(CF_2)_j$F (wherein k is a number of 1 to 10 (preferably from 1 to 6, more preferably from 1 to 4, still more preferably 2) and j is a number of 1 to 10 (preferably from 1 to 6, more preferably from 1 to 4)).

Examples of the non-nucleophilic anion as $X^-$ include sulfonate anion, carboxylate anion, sulfonylimide anion, bis(alkylsulfonyl)imide anion and tris(alkylsulfonyl)methyl anion.

The non-nucleophilic anion is an anion having an extremely low ability of causing a nucleophilic reaction and this anion can prevent the decomposition in aging due to intramolecular nucleophilic reaction, whereby the aging stability of resist is enhanced.

Examples of the sulfonate anion include alkyl-sulfonate anion, arylsulfonate anion and camphorsulfonate anion.

Examples of the carboxylate anion include alkyl-carboxylate anion, arylcarboxylate anion and aralkyl-carboxylate anion.

The alkyl group in the alkylsulfonate anion is preferably an alkyl group having from 1 to 30 carbon atoms, such as methyl group, ethyl group, propyl group, isopropyl group, n-butyl group, isobutyl group, sec-butyl group, pentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, cyclopropyl group, cyclopentyl group, cyclohexyl group, adamantyl group, norbornyl group and boronyl group.

The aryl group in the arylsulfonate anion is preferably an aryl group having from 6 to 14 carbon atoms, such as phenyl group, tolyl group and naphthyl group.

The alkyl group and aryl group in the alkylsulfonate anion and arylsulfonate anion each may have a substituent.

Examples of the substituent include a nitro group, a halogen atom (e.g., fluorine, chlorine, bromine, iodine), a carboxyl group, a hydroxyl group, an amino group, a cyano group, an alkoxy group (preferably having from 1 to 5 carbon atoms), an aryl group (preferably having from 6 to 14 carbon atoms), an alkoxycarbonyl group (preferably having from 2 to 7 carbon atoms), an acyl group (preferably having from 2 to 12 carbon atoms) and an alkoxycarbonyloxy group (preferably having from 2 to 7 carbon atoms). Furthermore, examples of the substituent for the aryl group and ring structure in each group include an alkyl group (preferably having from 1 to 15 carbon atoms).

Examples of the alkyl group in the alkylcarboxylate anion are the same as those of the alkyl group in the alkylsulfonate anion.

Examples of the aryl group in the arylcarboxylate anion are the same as those of the aryl group in the arylsulfonate anion.

The aralkyl group in the aralkylcarboxylate anion is preferably an aralkyl group having from 6 to 12 carbon atoms, such as benzyl group, phenethyl group, naphthylmethyl group, naphthylethyl group and naphthylmethyl group.

The alkyl group, aryl group and aralkyl group in the alkylcarboxylate anion, arylcarboxylate anion and aralkylcarboxylate anion each may have a substituent and examples of the substituent include the same halogen atom, alkyl group, alkoxy group and alkylthio group as in the case of arylsulfonate anion.

Examples of the sulfonylimide anion include saccharin anion.

The alkyl group in the bis(alkylsulfonyl)imide anion and tris(alkylsulfonyl)methyl anion is preferably an alkyl group having from 1 to 5 carbon atoms, such as methyl group, ethyl group, propyl group, isopropyl group, n-butyl group, isobutyl group, sec-butyl group, pentyl group and neopentyl group. The alkyl group may have a substituent and examples of the substituent include a halogen atom, a halogen atom-substituted alkyl group, an alkoxy group and an alkylthio group, with a halogen atom-substituted alkyl group being preferred.

Other examples of the non-nucleophilic anion include fluorinated phosphorus, fluorinated boron and fluorinated antimony.

The non-nucleophilic anion of $X^-$ is preferably alkanesulfonate anion with the α-position of sulfonic acid being substituted by a fluorine atom, arylsulfonate anion substituted by a fluorine atom or a group having a fluorine atom, bis(alkylsulfonyl)imide anion with the alkyl group being substituted by a fluorine atom, or tris(alkyl-sulfonyl)methide anion with the alkyl group being substituted by a fluorine atom, more preferably perfluoroalkanesulfonate anion having from 4 to 8 carbon atoms or benzenesulfonate anion having a fluorine atom, and most preferably nonafluorobutanesulfonate anion, perfluoro-octanesulfonate anion, pentafluorobenzenesulfonate anion or 3,5-bis(trifluoromethyl)benzenesulfonate anion.

The compound represented by formula (I) is preferably represented by formula (I').

In formula (I'),

Y represents an aryl group, an alkyl group, a cycloalkyl group, an alkenyl group, a —C(=O)—$Y_{3a}$ group or a —$Y_{3b}$—C(=O)—$Y_{3c}$ group (wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group (wherein $R_3$ and $R_4$ each independently represents a hydrogen atom, an alkyl group or a cycloalkyl group), and $Y_{3b}$ represents a divalent linking group resulting from removal of one hydrogen atom from said $Y_{3a}$), $R_1'$ and $R_2'$ each independently represents a hydrogen atom, an alkyl group or a cycloalkyl group, $Y_3$ and $Y_4$ each independently represents an alkyl group or a cycloalkyl group, $X^-$ represents a non-nucleophilic anion, m represents 0 or 1, and n represents 1 or 2, provided that m+n=2.

Y and $X^-$ in formula (I') have the same meanings as Y and $X^-$ in formula (I).

Examples of the alkyl group and cycloalkyl group of $R_1'$ and $R_2'$ in formula (I') are the same as those of the alkyl group and cycloalkyl group of $R_1$ and $R_2$ in formula (I).

Examples of the alkyl group and cycloalkyl group of $Y_4$ in formula (I') are the same as those of the alkyl group and cycloalkyl group of $Y_1$ and $Y_2$ in formula (I).

The alkyl group of $Y_3$ in formula (I') is preferably an alkyl group having from 1 to 30 carbon atoms, such as methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and eicosyl group.

The cycloalkyl group of $Y_3$ in formula (I') is preferably a cycloalkyl group having from 3 to 30 carbon atoms, such as cyclopropyl group, cyclobutyl group, cyclopentyl group, cyclohexyl group, norbornyl group, menthyl group and adamantyl group.

The alkyl group and cycloalkyl group of $Y_3$ each may have a substituent such as fluorine atom.

$Y_3$ is preferably an alkyl group having from 1 to 20 carbon atoms or a fluoroalkyl group having from 1 to 20 carbon atoms, more preferably a partially fluorinated fluoroalkyl group having from 1 to 20 carbon atoms, and most preferably a group represented by —$(CH_2)_k(CF_2)_j$F (wherein k is a number of 1 to 10 (preferably from 1 to 6, more preferably from 1 to 4, still more preferably 2) and j is a number of 1 to 10 (preferably from 1 to 6, more preferably from 1 to 4)).

The compound (A) of the present invention has a high photo-acid generating ability for light of 200 nm or less, particularly ArF excimer laser light (193 nm) and $F_2$ excimer laser light (157 nm), and a photosensitive composition using this compound exhibits high sensitivity and good profile.

Specific preferred examples of the compound (A) of the present invention are set forth below, but the present invention is not limited thereto.
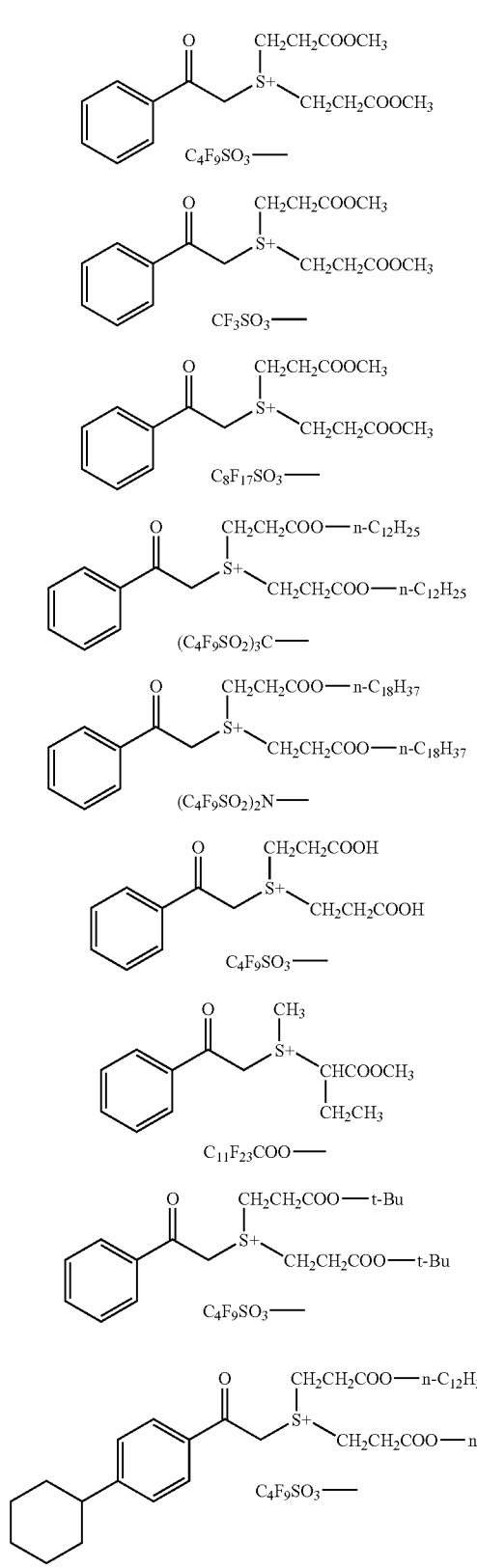
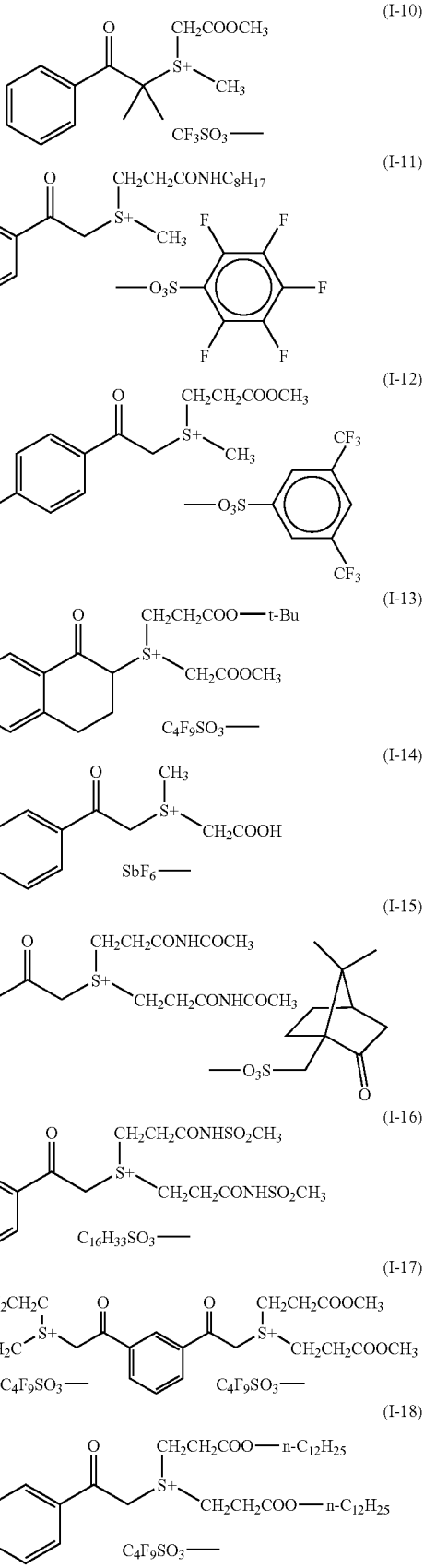

-continued
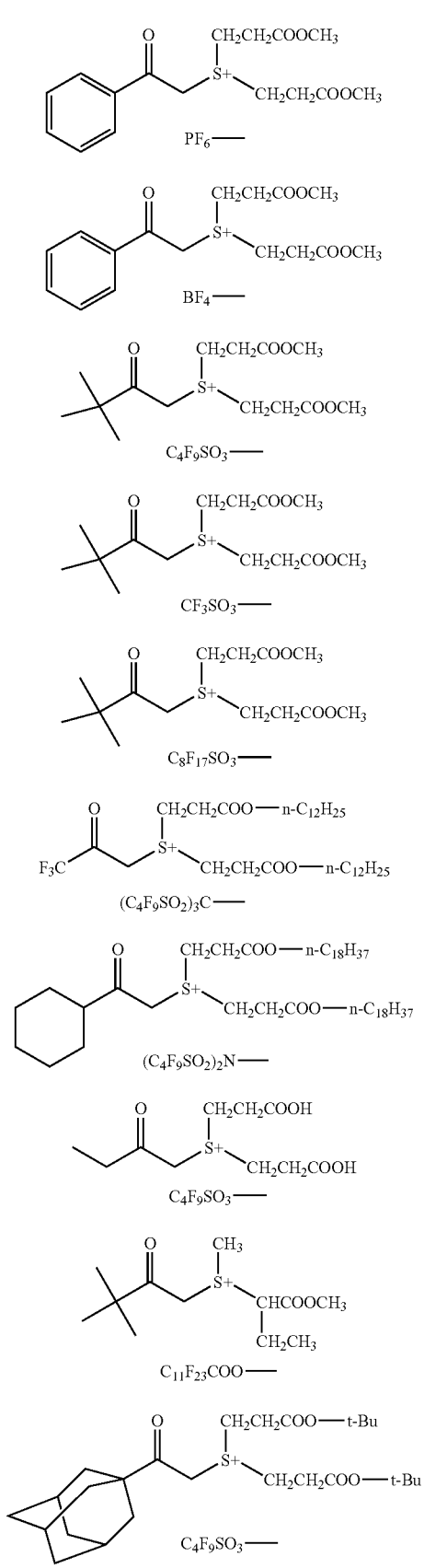
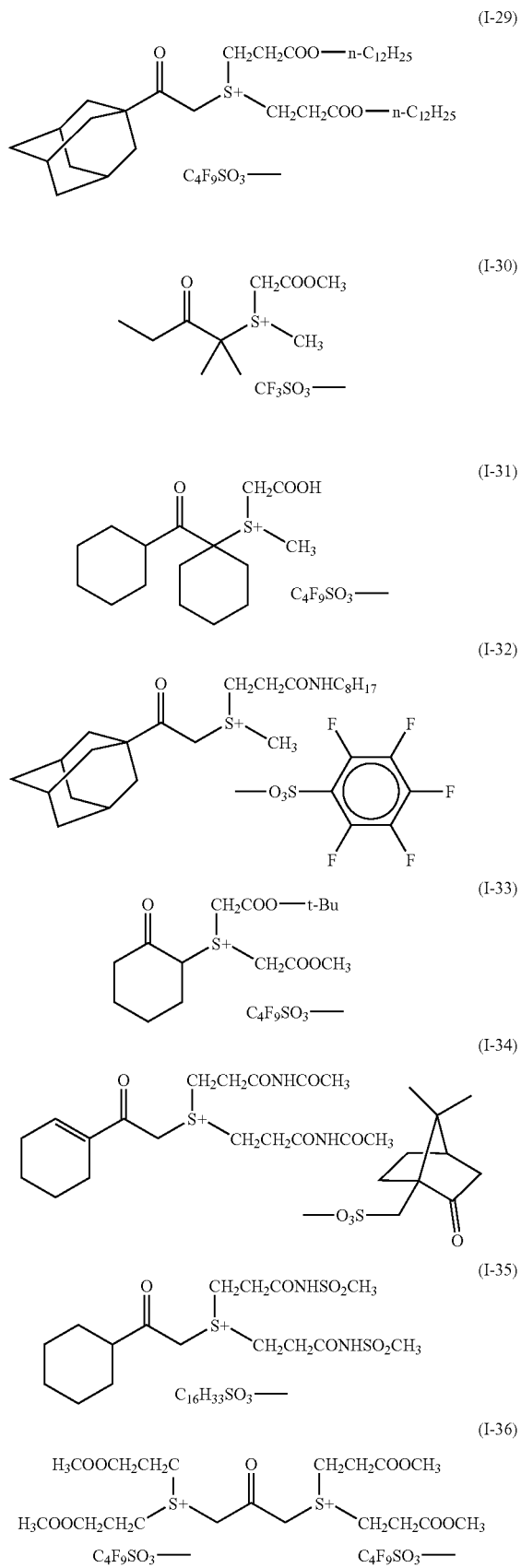

-continued
(I-37) 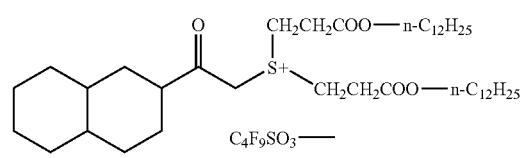
(I-38) 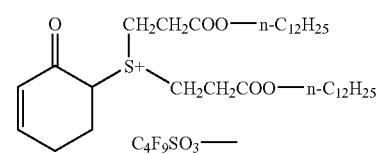
(I-39) 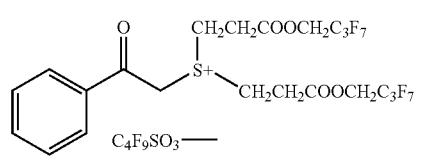
(I-40) 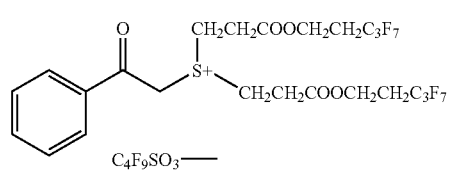
(I-41) 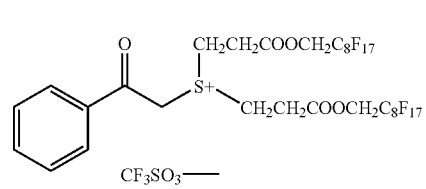
(I-42) 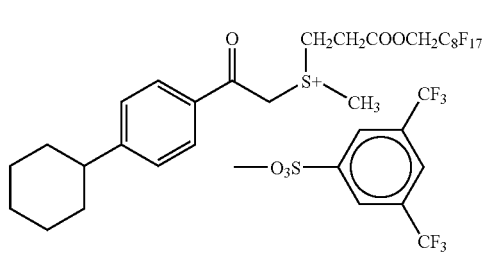
(I-43) 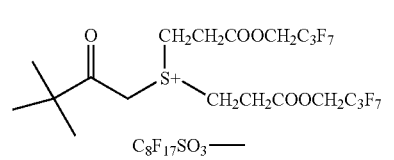
(I-44) 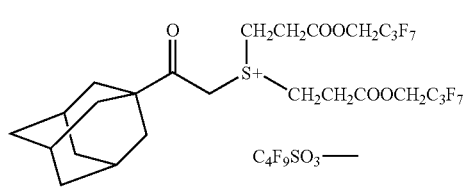
(I-45) 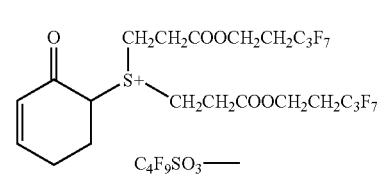
-continued
(I-46) 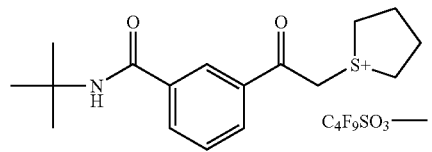
(I-47) 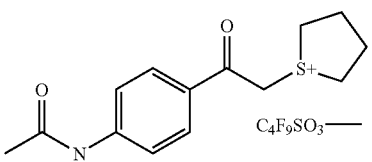
(I-48) 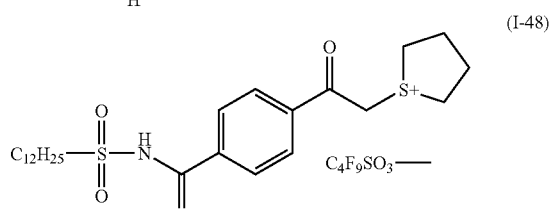
(I-49) 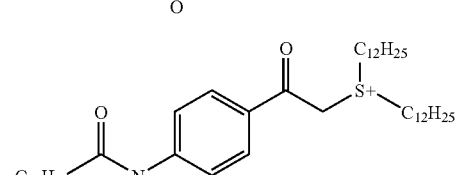
(I-50) 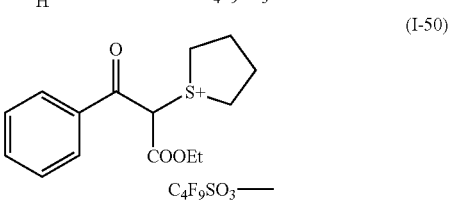
(I-51) 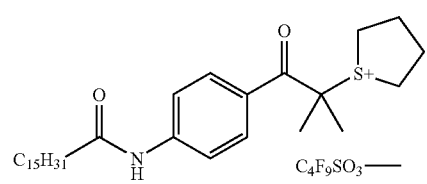
(I-52) 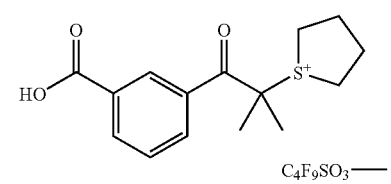
(I-53) 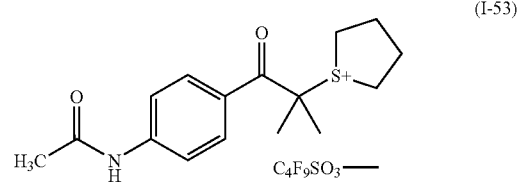
(I-54) 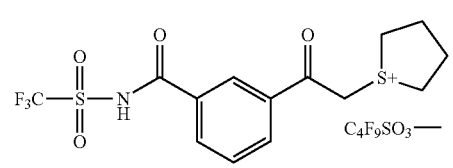

-continued

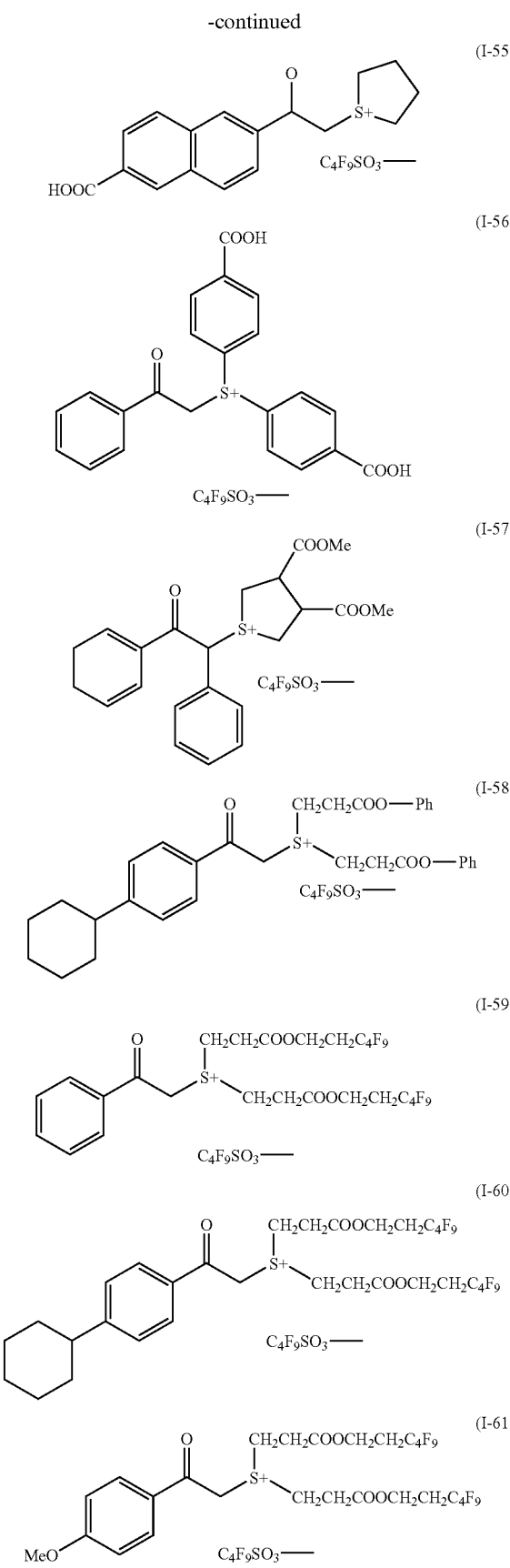
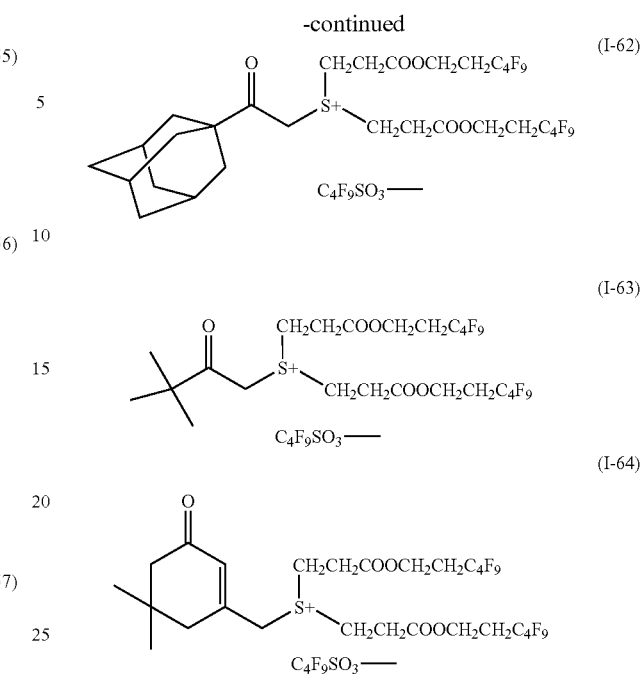

One compound (A) may be used alone or two or more compounds (A) may be used in combination.

The compound (A) can be obtained by reacting a corresponding 2-halogen-substituted ketone and a sulfide compound in the presence or absence of a silver catalyst to synthesize a sulfonium skeleton and salt-exchanging the skeleton with a corresponding anion. In another synthesis method, a corresponding ketone derivative is reacted with a trialkylsilylhalogenide under basic conditions to produce a silylenol ether form, reacting this with a sulfoxide to synthesize a sulfonium skeleton and salt-exchanging the skeleton with a corresponding anion, whereby the compound (A) can be obtained.

The content of the compound (A) in the stimulus-sensitive composition of the present invention is, based on the solid content of the composition, preferably from 0.1 to 20 mass %, more preferably from 1.0 to 15 mass %, still more preferably from 3.0 to 10 mass %.

(Acid Generator Used in Combination)

In the present invention, a compound of decomposing upon irradiation with an actinic ray to generate an acid may be further used in combination, in addition to the compound (A).

The amount of the photo-acid generator which can be used in combination is, in terms of the molar ratio (compound (A)/another acid generator), usually from 100/0 to 20/80, preferably from 100/0 to 40/60, more preferably from 100/0 to 50/50.

This photo-acid generator which can be used in combination may be appropriately selected from a photoinitiator for photocationic polymerization, a photoinitiator for photoradical polymerization, a photo-decoloring agent for dyes, a photo-discoloring agent, a known compound of generating an acid upon irradiation with an actinic ray used for microresist and the like, and a mixture thereof.

Examples thereof include diazonium salt, phosphonium salt, sulfonium salt, iodonium salt, imidosulfonate, oxime sulfonate, diazodisulfone, disulfone and o-nitrobenzyl sulfonate.

In addition, compounds where the above-described group or compound of generating an acid upon irradiation with an actinic ray is introduced into the polymer main or side chain, described, for example, in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029 may also be used.

Furthermore, compounds of generating an acid under the action of light, described, for example, in U.S. Pat. No. 3,779,778 and European Patent 126,712 may also be used.

Among the compounds of decomposing upon irradiation with an actinic ray to generate an acid, which can be used in combination, preferred are the compounds represented by the following formulae (ZI), (ZII) and (ZIII):

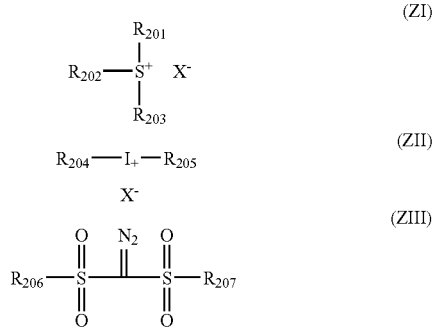

In formula (ZI), $R_{201}$, $R_{202}$ and $R_{203}$ each independently represents an organic group.

$X^-$ represents a non-nucleophilic anion and examples thereof are the same as those of the non-nucleophilic anion of $X^-$ in formula (I).

The carbon number of the organic group of $R_{201}$, $R_{202}$ and $R_{203}$ is generally from 1 to 30, preferably from 1 to 20.

Two out of $R_{201}$, $R_{202}$ and $R_{203}$ may combine to form a ring structure and the ring may contain an oxygen atom, a sulfur atom, an ester bond, an amide bond or a carbonyl group.

Examples of the group formed by the combining of two out of $R_{201}$ to $R_{203}$ include an alkylene group (e.g., butylene, pentylene).

Specific examples of the organic group of $R_{201}$, $R_{202}$ and $R_{203}$ include the corresponding groups in the compounds (Z1-1), (Z1-2) and (Z1-3) described later.

The compound may have a plurality of structures represented by formula (Z1). For example, a compound having a structure that at least one of $R_{201}$ to $R_{203}$ in the compound represented by formula (Z1) is bonded to at least one of $R_{201}$ to $R_{203}$ in another compound represented by formula (Z1) may also be used.

The (Z1) component is more preferably a compound of (Z1-1), (Z1-2) or (Z1-3) described below.

The compound (Z1-1) is an arylsulfonium compound where at least one of $R_{201}$ to $R_{203}$ in formula (Z1) is an aryl group, that is, a compound having an arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group.

Examples of the arylsulfonium compound include a triarylsulfonium compound, a diarylalkylsulfonium compound and an aryldialkylsulfonium compound.

The aryl group in the arylsulfonium compound is preferably a phenyl group or a naphthyl group, more preferably a phenyl group. In the case where the arylsulfonium compound has two or more aryl groups, these two or more aryl groups may be the same of different.

The alkyl group which is present, if desired, in the arylsulfonium compound is preferably a linear, branched or cyclic alkyl group having from 1 to 15 carbon atoms, such as methyl group, ethyl group, propyl group, n-butyl group, sec-butyl group, tert-butyl group, cyclopropyl group, cyclobutyl group and cyclohexyl group.

The aryl group and alkyl group of $R_{201}$ to $R_{203}$ each may have, as the substituent, an alkyl group (for example, having from 1 to 15 carbon atoms), an aryl group (for example, having from 6 to 14 carbon atoms), an alkoxy group (for example, having from 1 to 15 carbon atoms), a halogen atom, a hydroxyl group or a phenylthio group. The substituent is preferably a linear, branched or cyclic alkyl group having from 1 to 12 carbon atoms or a linear, branched or cyclic alkoxy group having from 1 to 12 carbon atoms, and most preferably an alkyl group having from 1 to 4 carbon atoms or an alkoxy group having from 1 to 4 carbon atoms. The substituent may be substituted to any one of $R_{201}$ to $R_{203}$ or may be substituted to all of these three groups. In the case where $R_{201}$ to $R_{203}$ are an aryl group, the substituent is preferably substituted at the p-position of the aryl group.

The compound (Z1-2) is described below.

The compound (Z1-2) is a compound where $R_{201}$ to $R_{203}$ in formula (1) each independently represents an organic group not containing an aromatic ring. The aromatic ring as used herein includes an aromatic ring containing a heteroatom.

The aromatic ring-free organic group of $R_{201}$ to $R_{203}$ generally has from 1 to 30 carbon atoms, preferably from 1 to 20 carbon atoms.

$R_{201}$ to $R_{203}$ each is independently preferably an alkyl group, an allyl group or a vinyl group, more preferably a linear, branched cyclic 2-oxoalkyl group or an alkoxycarbonylmethyl group, and most preferably a linear or branched 2-oxoalkyl group.

The alkyl group of $R_{201}$ to $R_{203}$ may be linear, branched or cyclic and is preferably a linear or branched alkyl group having from 1 to 10 carbon atoms (e.g., methyl, ethyl, propyl, butyl, pentyl) or a cyclic alkyl group having from 3 to 10 carbon atoms (e.g., cyclopentyl, cyclohexyl, norbornyl), more preferably a 2-oxoalkyl group or an alkoxycarbonylmethyl group.

The 2-oxoalkyl group may be linear, branched or cyclic and is preferably a group having >C=O at the 2-position of the above-described alkyl group.

The alkoxy group in the alkoxycarbonylmethyl group is preferably an alkyl group having from 1 to 5 carbon atoms (e.g., methyl, ethyl, propyl, butyl, pentyl).

$R_{201}$ to $R_{203}$ may be further substituted by a halogen atom, an alkoxy group (for example, having from 1 to 5 carbon atoms), a hydroxyl group, a cyano group or a nitro group.

Two out of $R_{201}$ to $R_{203}$ may combine to form a ring structure and the ring may contain an oxygen atom, a sulfur atom, an ester bond, an amide bond or a carbonyl group. Examples of the group formed by the combining of two out of $R_{201}$ to $R_{203}$ include an alkylene group (e.g., butylene, pentylene).

The compound (Z1-3) is a compound represented by the following formula (Z1-3) and this is a compound having a phenacylsulfonium salt structure.

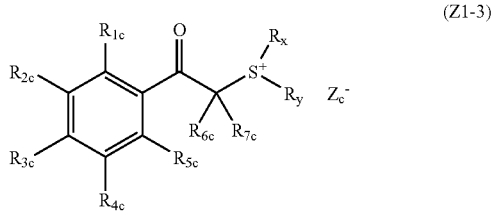

(Z1-3)

R<sub>1c</sub> to R<sub>5c</sub> each independently represents a hydrogen atom, an alkyl group, an alkoxy group or a halogen atom.

$R_{6c}$ and $R_{7c}$ each represents a hydrogen atom or an alkyl group.

$R_x$ and $R_y$ each independently represents an alkyl group, an aryl group or a vinyl group.

Any two or more out of $R_{1c}$ to $R_{5c}$, or $R_x$ and $R_y$ may combine to form a ring structure and the ring structure may contain an oxygen atom, a sulfur atom, an ester bond or an amide bond.

Zc⁻ represents a non-nucleophilic anion and examples thereof are the same as those of the non-nucleophilic anion of X⁻ in formula (I).

The alkyl group of $R_{1c}$ to $R_{5c}$ may be linear, branched or cyclic and this is, for example, an alkyl group having from 1 to 20 carbon atoms, preferably a linear or branched alkyl group having from 1 to 12 carbon atoms (e.g., methyl, ethyl, linear or branched propyl, linear or branched butyl, linear or branched pentyl) or a cyclic alkyl group having from 3 to 8 carbon atoms (e.g., cyclopentyl, cyclohexyl).

The alkoxy group of $R_{1c}$ to $R_{5c}$ may be linear, branched or cyclic and this is, for example, an alkoxy group having from 1 to 10 carbon atoms, preferably a linear or branched alkoxy group having from 1 to 5 carbon atoms (e.g., methoxy, ethoxy, linear or branched propoxy, linear or branched butoxy, linear or branched pentoxy) or a cyclic alkoxy group having from 3 to 8 carbon atoms (e.g., cyclopentyloxy, cyclohexyloxy).

A compound where any one of $R_{1c}$ to $R_{5c}$ is a linear, branched or cyclic alkyl group or a linear, branched or cyclic alkoxy group is preferred, and a compound where the sum of carbon atoms of $R_{1c}$ to $R_{5c}$ is from 2 to 15 is more preferred. If the case is so, the solubility in solvent is enhanced and the generation of particles during storage is prevented.

Examples of the alkyl group of $R_x$ and $R_y$ are the same as those of the alkyl group of $R_{1c}$ to $R_{5c}$. Among these, preferred are a 2-oxoalkyl group or an alkoxycarbonylmethyl group.

Examples of the 2-oxoalkyl group include a group having >C=O at the 2-position of the alkyl group of $R_{1c}$ to $R_{5c}$.

Examples of the alkoxy group in the alkoxycarbonylmethyl group are the same as those of the alkoxy group of $R_{1c}$ to $R_{5c}$.

Examples of the group formed by the combining of $R_x$ and $R_y$ include a butylenes group and a pentylene group.

$R_x$ and $R_y$ each is preferably an alkyl group having 4 or more carbon atoms, more preferably 6 or more carbon atoms, still more preferably 8 or more carbon atoms.

In formulae (ZII) and (ZIII), $R_{204}$ to $R_{207}$ each independently represents an aryl group which may have a substituent, or an alkyl group which may have a substituent.

The aryl group of $R_{204}$ to $R_{207}$ is preferably a phenyl group or a naphthyl group, more preferably a phenyl group.

The alkyl group of $R_{204}$ to $R_{207}$ may be linear, branched or cyclic and is preferably a linear or branched alkyl group having from 1 to 10 carbon atoms (e.g., methyl, ethyl, propyl, butyl, pentyl) or a cyclic alkyl group having from 3 to 10 carbon atoms (e.g., cyclopentyl, cyclohexyl, norbornyl).

Examples of the substituent which may be substituted to $R_{204}$ to $R_{207}$ include an alkyl group (for example, having from 1 to 15 carbon atoms), an aryl group (for example, having from 6 to 15 carbon atoms), an alkoxy group (for example, having from 1 to 15 carbon atoms), a halogen atom, a hydroxyl group and a phenylthio group.

X⁻ represents a non-nucleophilic anion and examples thereof are the same as those of the non-nucleophilic anion of X⁻ in formula (I).

Among the compounds of decomposing upon irradiation with actinic rays or radiation to generate an acid, which can be used in combination, also preferred are the compounds represented by the following formulae (ZIV), (ZV) and (ZVI):

(ZIV)

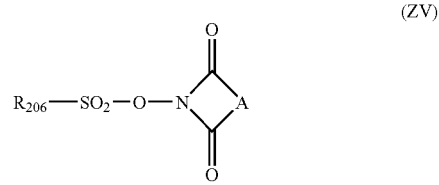

(ZV)

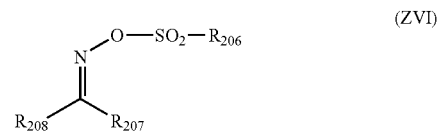

(ZVI)

wherein $Ar_3$ and $Ar_4$ each independently represents a substituted or unsubstituted aryl group, $R_{206}$, $R_{207}$ and $R_{208}$ each represents a substituted or unsubstituted alkyl group or a substituted or unsubstituted aryl group, and A represents a substituted or unsubstituted alkylene group, a substituted or unsubstituted alkenylene group or a substituted or unsubstituted arylene group.

Among the compounds of decomposing upon irradiation with an actinic ray to generate an acid, which can be used in combination, more preferred are the compounds represented by formulae (ZI) to (ZIII).

Preferred examples of the compound of decomposing upon irradiation with an actinic ray to generate an acid, which can be used in combination, are set forth below.

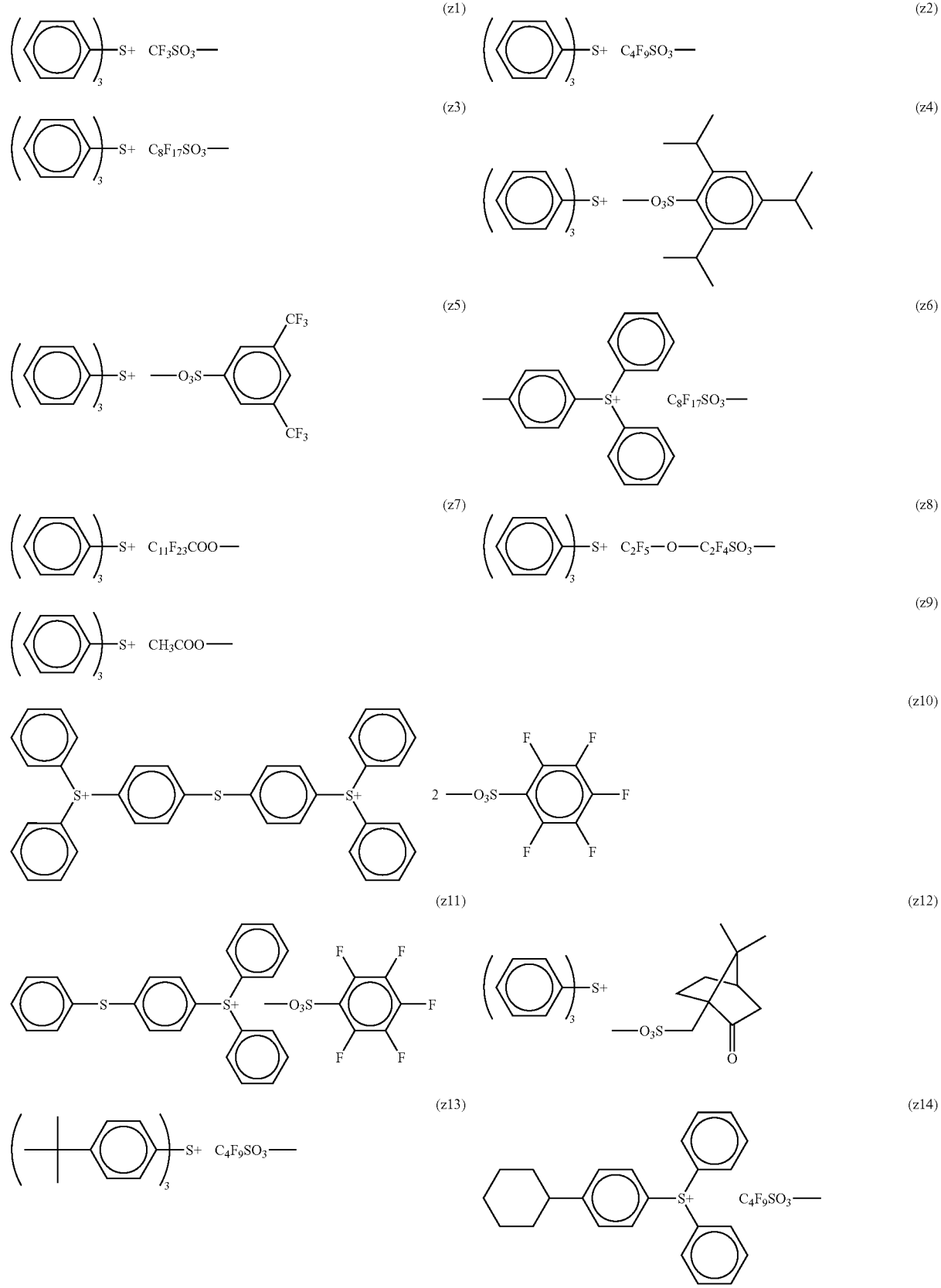

-continued
(z15)
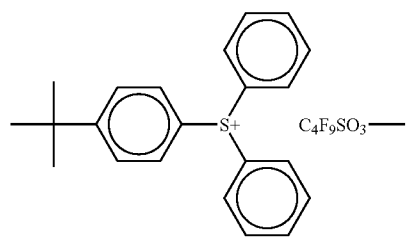
(z16)
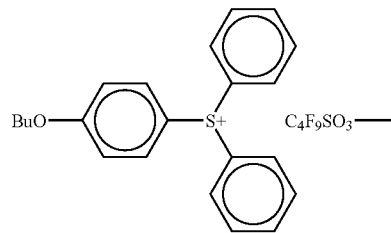
(z17)
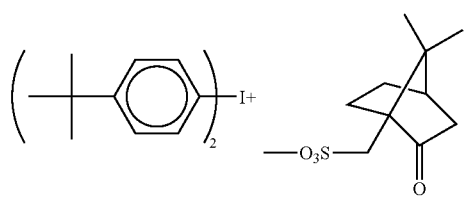
(z18)
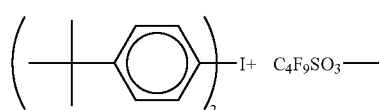
(z19)
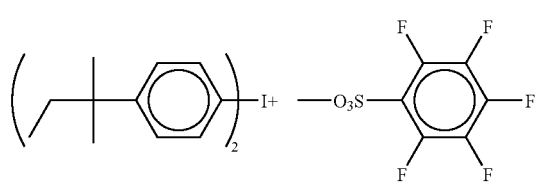
(z20)
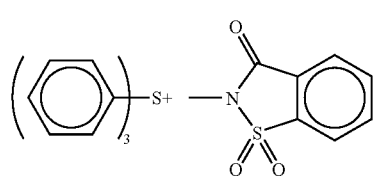
(z21)
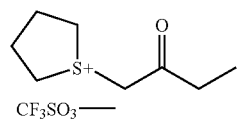
(z22)
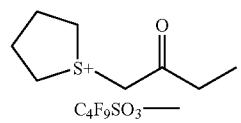
(z23)
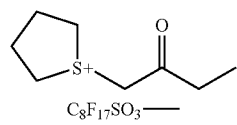
(z24)
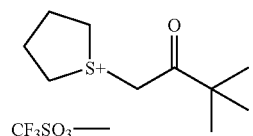
(z25)
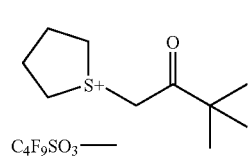
(z26)
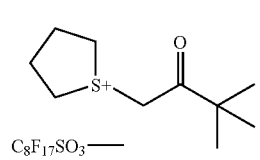
(z27)
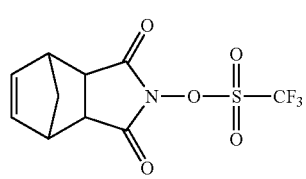
(z28)
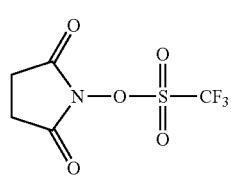
(z29)
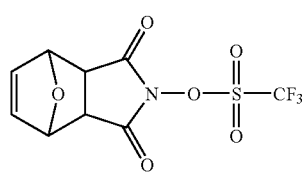
(z30)
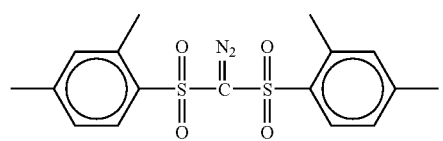
(z31)
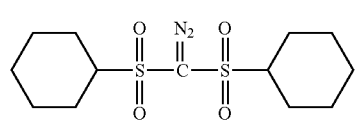
(z32)
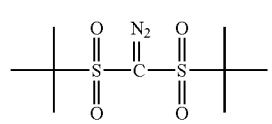

-continued
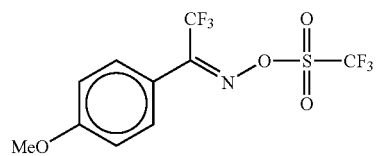 (z33)
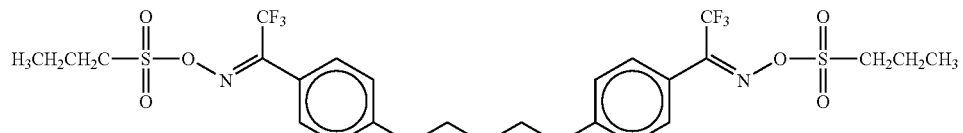 (z34)
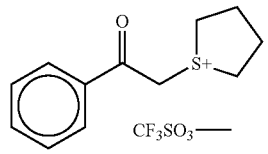 (z35)
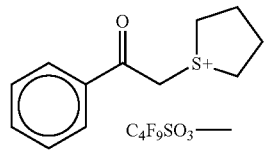 (z36)
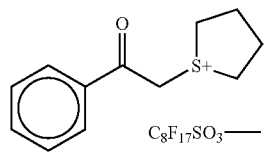 (z37)
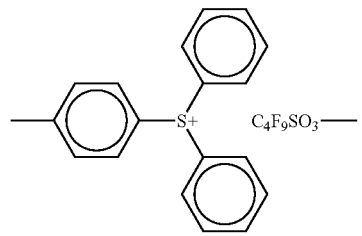 (z38)
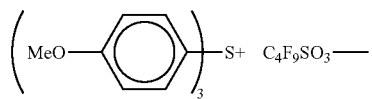 (z39)
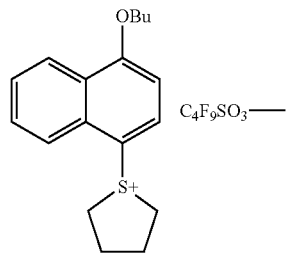 (z40)
 (z41)
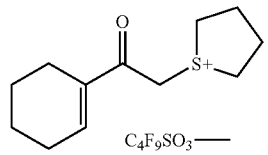 (z42)
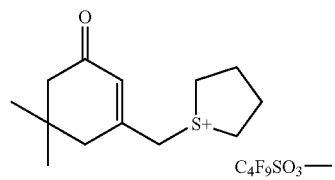 (z43)
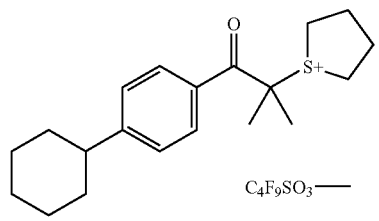 (z44)
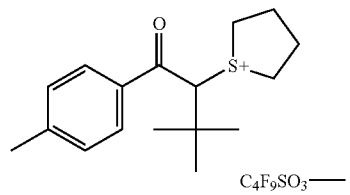 (z45)
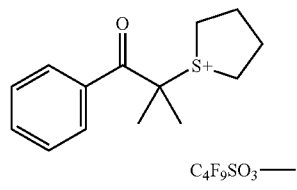 (z46)

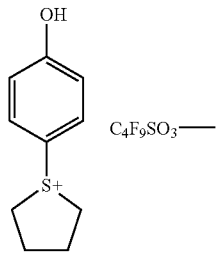
(z47)

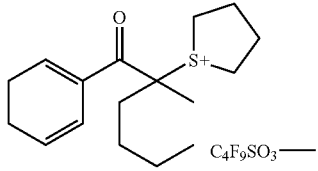
(z48)

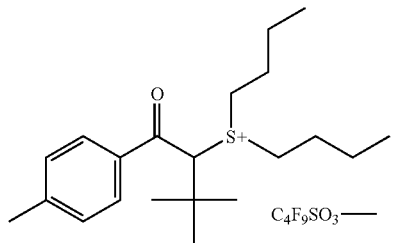
(z49)

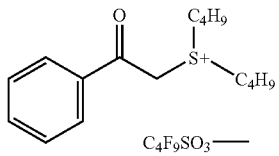
(z50)

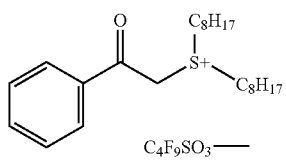
(z51)

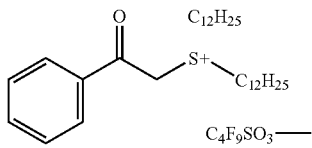
(z52)

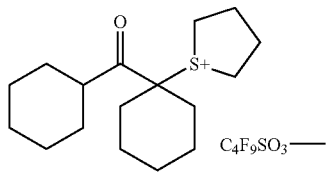
(z53)

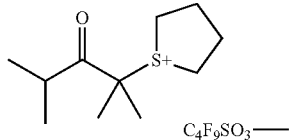
(z54)

[2] (B) Resin that Decomposes Under the Action of an Acid to Increase the Solubility in an Alkali Developer (Hereinafter Sometimes Referred to as a "Component B")

The resin that decomposes under the action of an acid to increase the solubility in an alkali developer, which is used for the positive stimulus-sensitive composition of the present invention, is a resin where a group capable of decomposing by an acid (hereinafter sometimes referred to as an "acid decomposable group") is present in ether one or both of the main chain and the side chain of resin. Among these resins, a resin having an acid decomposable group in the side chain is preferred.

The group capable of decomposing by an acid is preferably a group resulting from displacement of a hydrogen atom of a —COOH or —OH group with a group which splits off by an acid.

In the present invention, the acid decomposable group is an acetal group or a tertiary ester group.

In the case where the group capable of decomposing by an acid is bonded as a side chain, the mother resin is an alkali-soluble resin having an —OH or —COOH group in the side chain. Examples thereof include alkali-soluble resins described later.

The alkali dissolution rate of the alkali-soluble resin is preferably 170 Å/sec or more, more preferably 330 Å/sec or more (Å is angstrom), as measured (at 23° C.) in 0.261N tetramethylammonium hydroxide (TMAH).

From this standpoint, the alkali-soluble resin is preferably an alkali-soluble resin having a hydroxystyrene structure unit, such as an o-, m- or p-poly(hydroxystyrene) or a copolymer thereof, a hydrogenated poly(hydroxystyrene), a halogen- or alkyl-substituted poly(hydroxystyrene), a partially O-alkylated or O-acylated poly(hydroxystyrene), a styrene-hydroxystyrene copolymer, an α-methylstyrene-hydroxystyrene copolymer and a hydrogenated novolak resin.

Examples of the repeating unit having an acid decomposable group preferred in the present invention include tert-butoxycarbonyloxystyrene, 1-alkoxyethoxy-styrene and tertiary alkyl (meth)acrylate.

The component (B) for use in the present invention can be obtained by reacting an acid decomposable group precursor with an alkali-soluble resin or copolymerizing an acid decomposable group-bonded alkali-soluble resin monomer with various monomers, and this is disclosed in European Patent 254853, JP-A-2-25850, JP-A-3-223860 and JP-A-4-251259.

Specific examples of the component (B) for use in the present invention are set forth below, but the present invention is not limited thereto.

p-tert-Butoxystyrene/p-hydroxystyrene copolymer
p-(tert-Butoxycarbonyloxy)styrene/p-hydroxystyrene copolymer
p-(tert-Butoxycarbonylmethyloxy)styrene/p-hydroxystyrene copolymer
4-(tert-Butoxycarbonylmethyloxy)-3-methylstyrene/4-hydroxy-3-methylstyrene copolymer
p-(tert-Butoxycarbonylmethyloxy)styrene/p-hydroxystyrene (10% hydrogenated product) copolymer m-(tert-Butoxycarbonylmethyloxy)styrene/m-hydroxystyrene copolymer
o-(tert-Butoxycarbonylmethyloxy)styrene/o-hydroxystyrene copolymer
p-(Cumyloxycarbonylmethyloxy)styrene/p-hydroxystyrene copolymer
Cumyl methacrylate/methyl methacrylate copolymer
4-tert-Butoxycarbonylstyrene/dimethyl maleate copolymer
Benzyl methacrylate/tetrahydropyranyl methacrylate copolymer
p-(tert-Butoxycarbonylmethyloxy)styrene/p-hydroxystyrene/styrene copolymer
p-tert-Butoxystyrene/p-hydroxystyrene/fumaronitrile copolymer
tert-Butoxystyrene/hydroxyethyl methacrylate copolymer
Styrene/N-(4-hydroxyphenyl)maleimide/N-(4-tert-butoxycarbonyloxyphenyl)maleimide copolymer p-Hydroxystyrene/tert-butyl methacrylate copolymer
Styrene/p-hydroxystyrene/tert-butyl methacrylate copolymer
p-Hydroxystyrene/tert-butyl acrylate copolymer
Styrene/p-hydroxystyrene/tert-butyl acrylate copolymer
p-(tert-Butoxycarbonylmethyloxy)styrene/p-hydroxystyrene/N-methylmaleimide copolymer
tert-Butyl methacrylate/1-adamantylmethyl methacrylate copolymer
p-Hydroxystyrene/tert-butyl acrylate/p-acetoxystyrene copolymer
p-Hydroxystyrene/tert-butyl acrylate/p-(tert-butoxycarbonyloxy)styrene copolymer
p-Hydroxystyrene/tert-butyl acrylate/p-(tert-butoxycarbonylmethyloxy)styrene copolymer

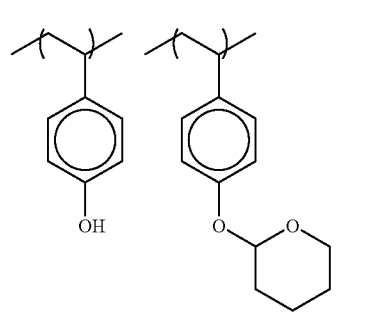

(R-1) (R-2)

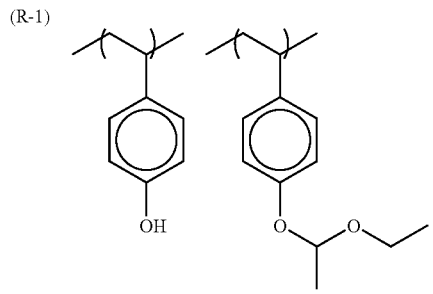

(R-3) (R-4)

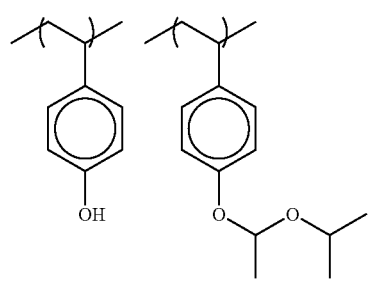

(R-5) (R-6)

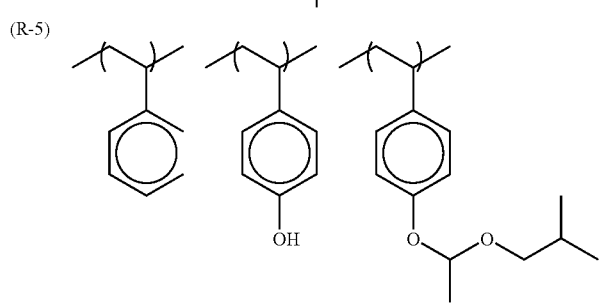

(R-7) (R-8)

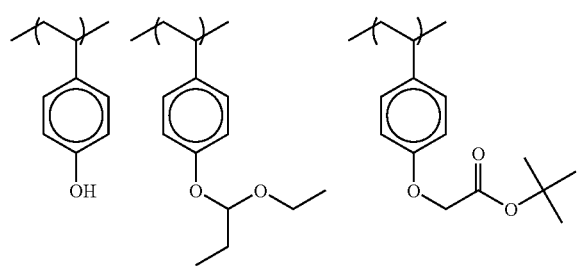

-continued
(R-9)
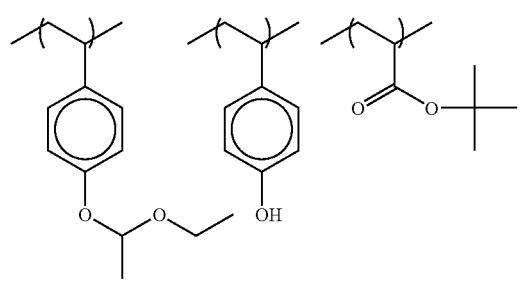
(R-10)
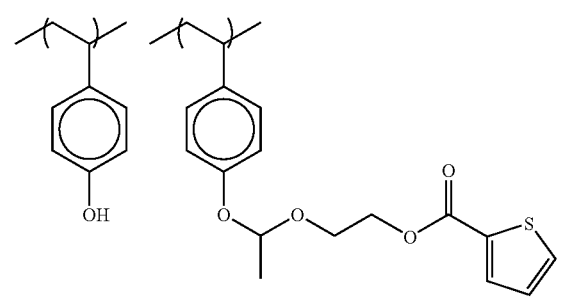
(R-11)
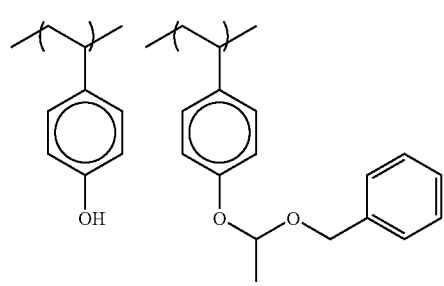
(R-12)
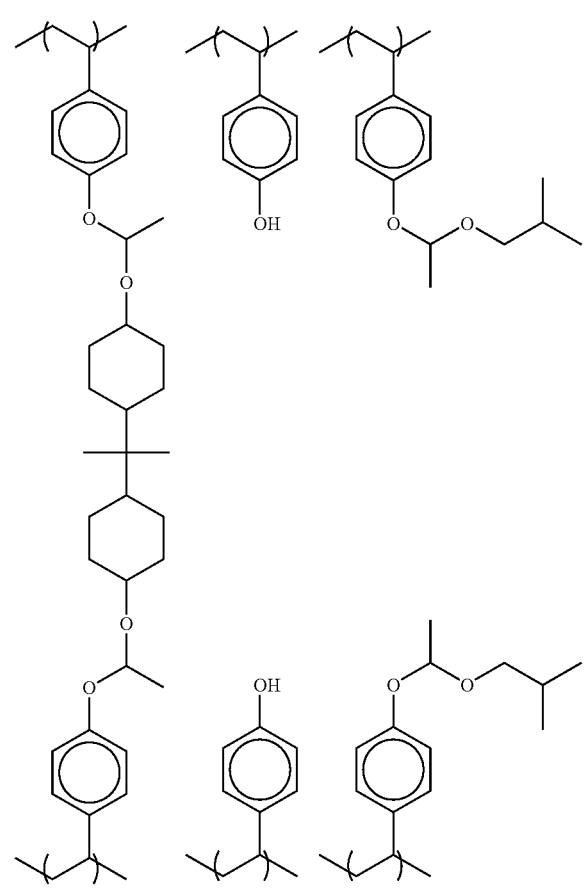
(R-13)
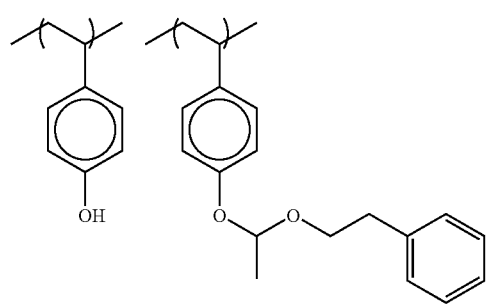
(R-14)

-continued
(R-15) 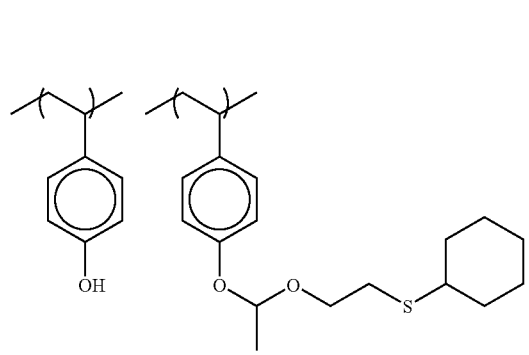
(R-16) 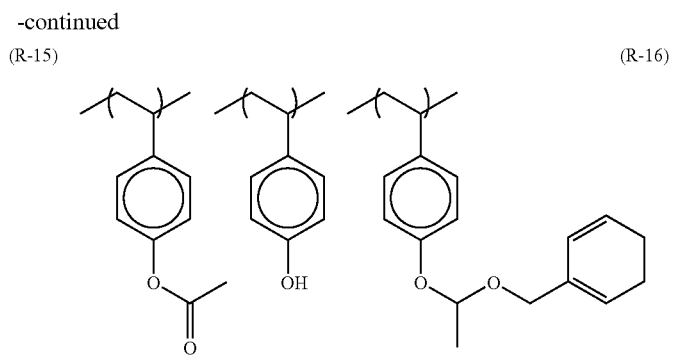
(R-17) 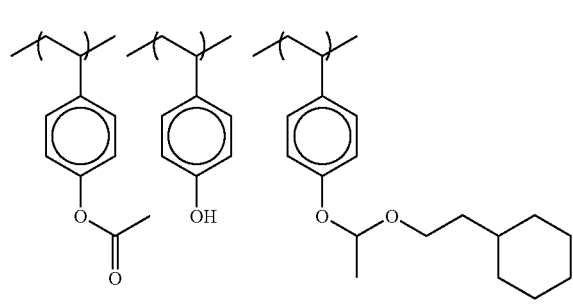
(R-18) 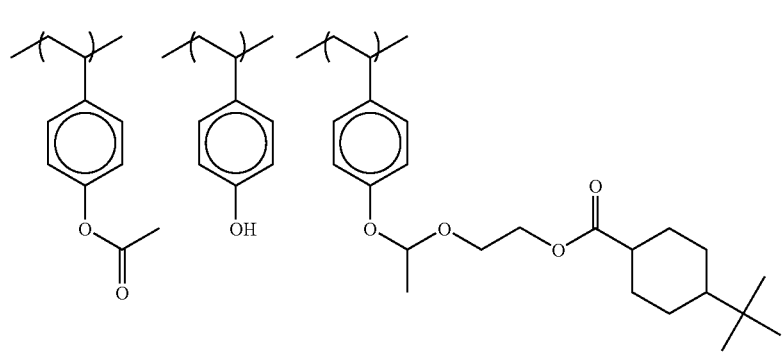
(R-19) 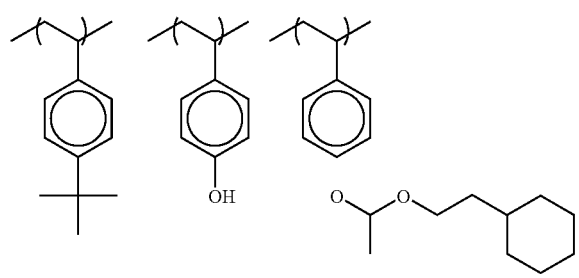
(R-20) 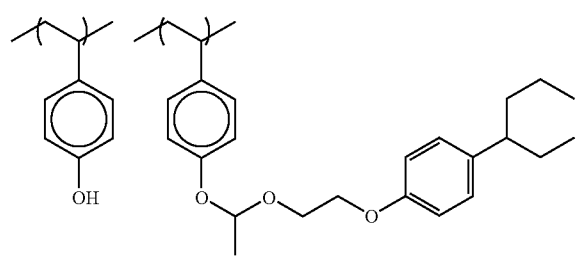
(R-21) 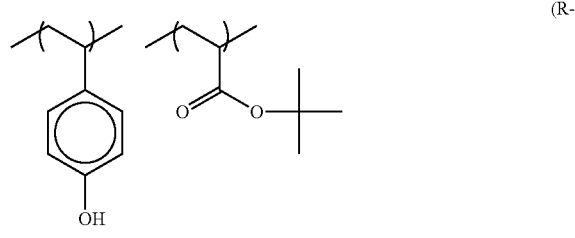
(R-22) 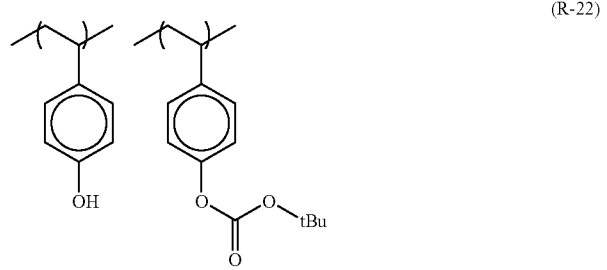

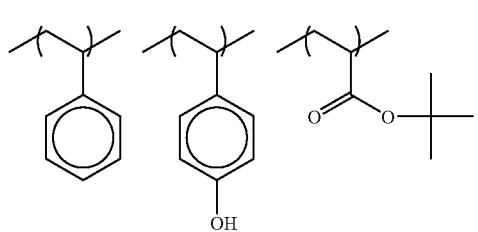

(R-23)

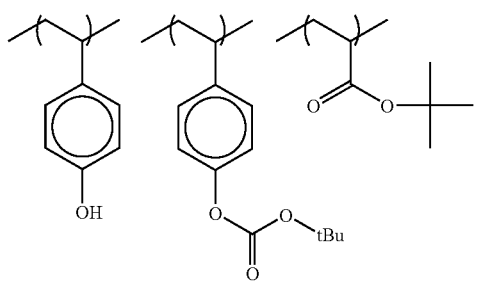

(R-24)

In these specific examples, "tBu" indicates a tert-butyl group.

The content of the group capable of decomposing by an acid is expressed by B/(B+S) using the number (B) of acid decomposable groups in the resin and the number (S) of alkali-soluble groups not protected by a group which splits off by an acid. The content is preferably from 0.01 to 0.7, more preferably from 0.05 to 0.50, still more preferably from 0.05 to 0.40.

In the case of irradiating ArF excimer laser light on the positive stimulus-sensitive composition of the present invention, the resin as the component (B) is preferably a resin having a monocyclic or polycyclic alicyclic hydrocarbon structure and undergoing decomposition under the action of an acid to increase the solubility in an alkali developer.

The resin having a monocyclic or polycyclic alicyclic hydrocarbon structure and undergoing decomposition under the action of an acid to increase the solubility in an alkali developer (hereinafter sometimes referred to as an "alicyclic hydrocarbon-base acid decomposable resin") is preferably a resin containing at least one repeating unit selected from the group consisting of a repeating unit having a partial structure containing an alicyclic hydrocarbon represented by any one of the following formulae (pI) to (pVI), and a repeating unit represented by the following formula (II-AB):

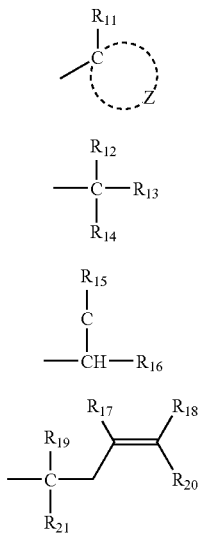

(pI)
(pII)
(pIII)
(pIV)

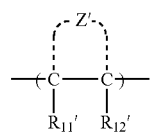

(pV)

(pVI)

(wherein $R_{11}$ represents a methyl group, an ethyl group, an n-propyl group, an isopropyl group, an n-butyl group, an isobutyl group or a sec-butyl group, Z represents an atomic group necessary for forming an alicyclic hydrocarbon group together with the carbon atom, $R_{12}$ to $R_{16}$ each independently represents a linear or branched alkyl group having from 1 to 4 carbon atoms or an alicyclic hydrocarbon group, provided that at least one of $R_{12}$ to $R_{14}$ or either one of $R_{15}$ and $R_{16}$ represents an alicyclic hydrocarbon group, $R_{17}$ to $R_{21}$ each independently represents a hydrogen atom, a linear or branched alkyl group having from 1 to 4 carbon atoms or an alicyclic hydrocarbon group, provided that at least one of $R_{17}$ to $R_{21}$ represents an alicyclic hydrocarbon group and that either one of $R_{19}$ and $R_{21}$ represents a linear or branched alkyl group having from 1 to 4 carbon atoms or an alicyclic hydrocarbon group, $R_{22}$ to $R_{25}$ each independently represents a hydrogen atom, a linear or branched alkyl group having from 1 to 4 carbon atoms or an alicyclic hydrocarbon group, provided that at least one of $R_{22}$ to $R_{25}$ represents an alicyclic hydrocarbon group, and $R_{23}$ and $R_{24}$ may combine with each other to form a ring).

(II-AB)

wherein $R_{11}'$ and $R_{12}'$ each independently represents a hydrogen atom, a cyano group, a halogen atom or an alkyl group which may have a substituent, and Z' represents an atomic group for forming an alicyclic structure containing two bonded carbon atoms (C—C), which may have a substituent.

Formula (II-AB) is preferably the following formula (II-A) or (II-B).

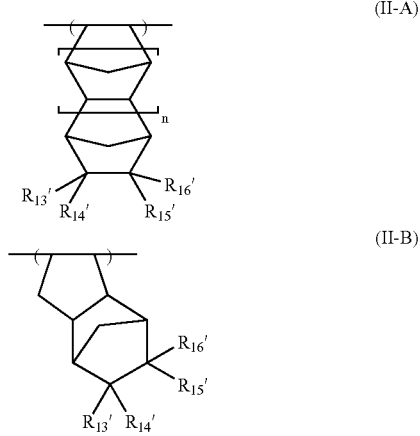

wherein $R_{13}'$ to $R_{16}'$ each independently represents a hydrogen atom, a halogen atom, a cyano group, —COOH, -COOR$_5$, a group of decomposing under the action of an acid, —C(=O)—X—A'—R$_{17}'$, or an alkyl or cyclic hydrocarbon group which may have a substituent, R$_5$ represents an alkyl group which may have a substituent, a cyclic hydrocarbon group or a —Y group shown below, X represents an oxygen atom, a sulfur atom, —NH—, —NHSO$_2$— or —NHSO$_2$NH—, A' represents a sing bond or a divalent linking group, at least two of $R_{13}'$ to $R_{16}'$ may combine to form a ring, n represents 0 or 1, $R_{17}'$ represents —COOH, —COOR$_5$, —CN, a hydroxyl group, an alkoxy group which may have a substituent, —CO—NH—R$_6$, —CO—NH—SO$_2$—R$_6$ or a —Y group shown below, and R$_6$ represents an alkyl or cyclic hydrocarbon group which may have a substituent: —Y group:

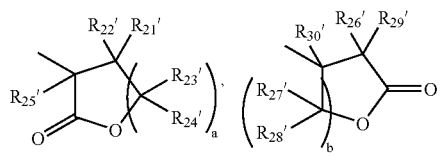

(wherein $R_{21}'$ to $R_{30}'$ each independently represents a hydrogen atom or an alkyl group, and a and b each represents 1 or 2).

In formulae (pI) to (pVI), the alkyl group of $R_{12}$ to $R_{25}$ is a linear or branched alkyl group having from 1 to 4 carbon atoms, which may be substituted or unsubstituted. Examples of the alkyl group include a methyl group, an ethyl group, an n-propyl group, an isopropyl group, an n-butyl group, an isobutyl group, a sec-butyl group and a tert-butyl group.

Examples of the substituent which is further substituted to the alkyl group include an alkoxy group having from 1 to 4 carbon atoms, a halogen atom (e.g., fluorine, chlorine, bromine, iodine), an acyl group, an acyloxy group, a cyano group, a hydroxyl group, a carboxy group, an alkoxycarbonyl group and a nitro group.

The alicyclic hydrocarbon group of $R_{11}$ to $R_{25}$ and the alicyclic hydrocarbon group formed by Z and the carbon atoms each may be monocyclic or polycyclic. Specific examples thereof include a group having a monocyclo-, bicyclo-, tricyclo- or tetracyclo-structure having 5 or more carbon atoms. The carbon number thereof is preferably from 6 to 30, more preferably from 7 to 25. These alicyclic hydrocarbon groups may have a substituent.

Among these alicyclic hydrocarbon groups, preferred are an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group, more preferred are an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituent for the alicyclic hydrocarbon group include an alkyl group, a halogen atom, a hydroxyl group, an alkoxy group, a carboxyl group and an alkoxycarbonyl group. The alkyl group is preferably a lower alkyl group such as methyl group, ethyl group, propyl group, isopropyl group and butyl group, more preferably a methyl group, an ethyl group, a propyl group or an isopropyl group. Examples of the alkoxy group include an alkoxy group having from 1 to 4 carbon atoms, such as methoxy group, ethoxy group, propoxy group and butoxy group. The alkyl group, alkoxy group and the alkoxycarbonyl group each may further have a substituent and examples of the substituent include a hydroxyl group, a halogen atom and an alkoxy group.

The structures represented by formulae (pI) to (pVI) each can be used for the protection of an alkali-soluble group in the resin. Examples of the alkali-soluble group include various groups known in this technical field.

Specific examples thereof include a carboxylic acid group, a sulfonic acid group, a phenol group and a thiol group. Among these, preferred are a carboxylic acid group and a sulfonic acid group.

Preferred examples of the alkali-soluble group protected by a structure represented by any one of formulae (pI) to (pVI) in the resin include structures where the hydrogen atom of a carboxyl group is substituted by a structure represented by any one of formulae (pI) to (pVI).

The repeating unit having an alkali-soluble group protected by a structure represented by any one of formulae (pI) to (pVI) is preferably a repeating unit represented by the following formula (pA):

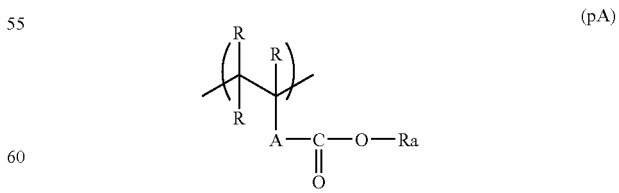

wherein R represents a hydrogen atom, a halogen atom or a substituted or unsubstituted linear or branched alkyl group having from 1 to 4 carbon atoms, and the plurality of Rs may be the same or different;

A represents a single bond, or a sole group or a combination of two or more groups, selected from the group consisting of an alkylene group, a substituted alkylene group, an ether group, a thioether group, a carbonyl group, an ester group, an amido group, a sulfonamido group, a urethane group and a urea group; and Ra represents any one group of formulae (pI) to (pVI).

The repeating unit represented by formula (pA) is most preferably a repeating unit comprising 2-alkyl-2-adamantyl (meth)acrylate or dialkyl(1-adamantyl)methyl (meth)acrylate.

Specific examples of the repeating unit represented by formula (pA) are set forth below.

(In formulae, Rx is H, CH$_3$ or CF$_3$.)

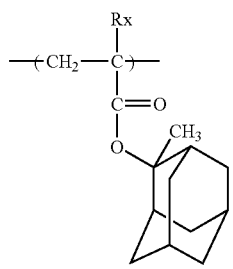

1

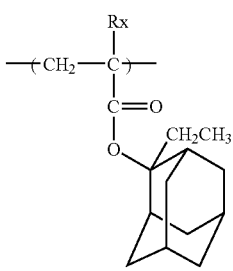

2

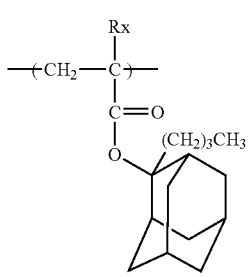

3

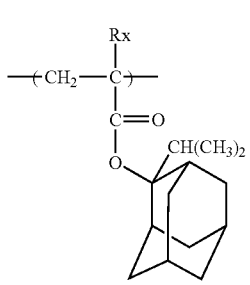

4

-continued

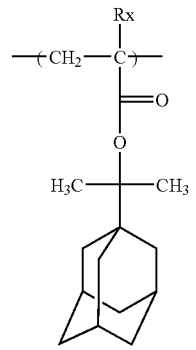

5

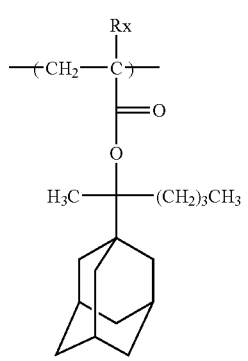

6

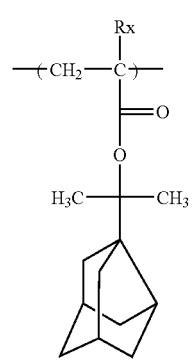

7

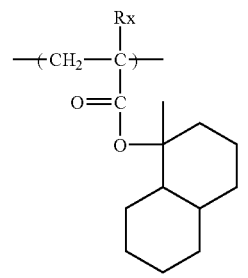

8

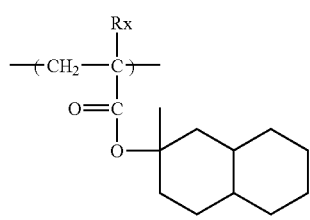

9

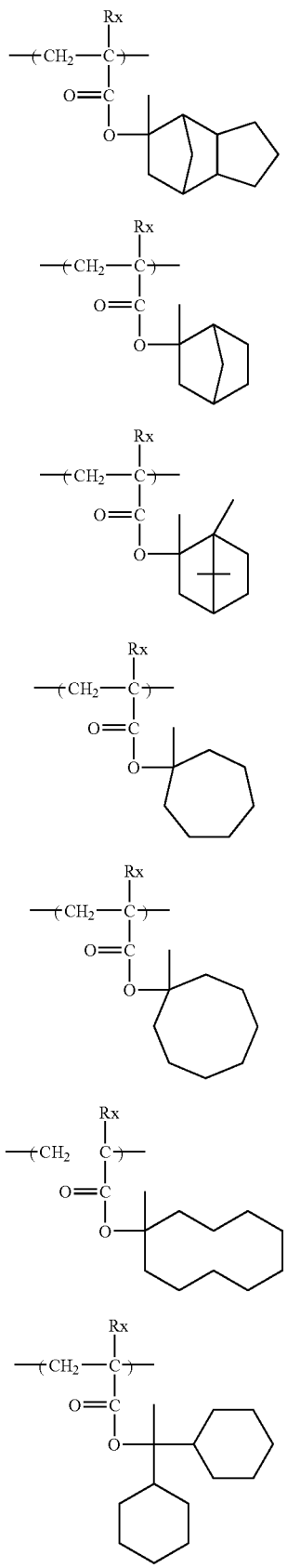
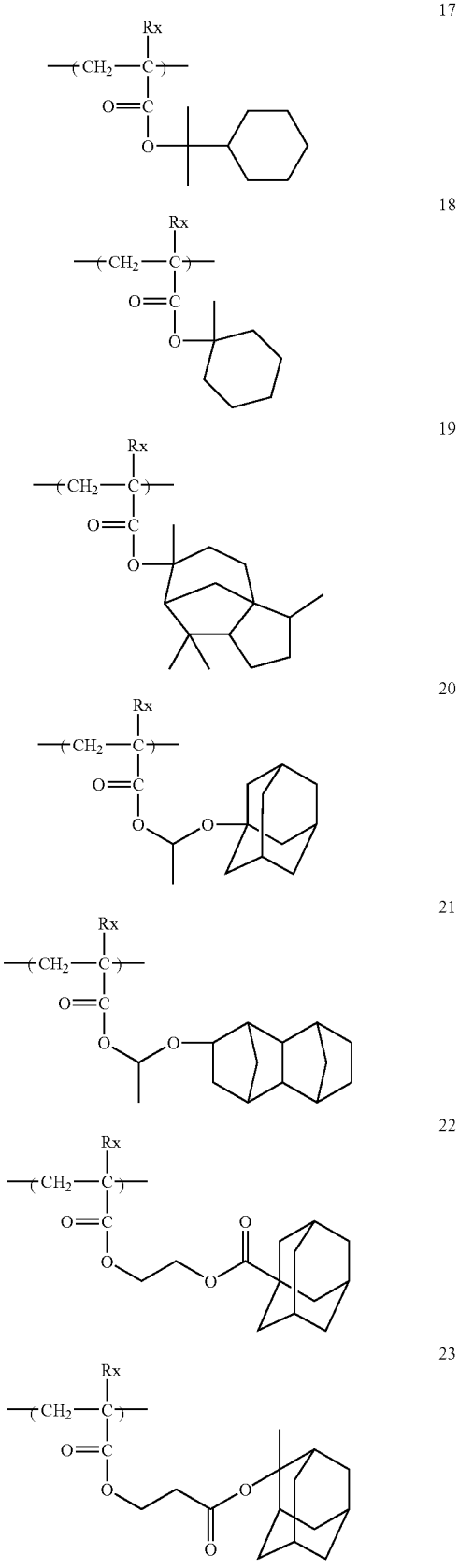

In formula (II-AB), $R_{11}'$ and $R_{12}'$ each independently represents a hydrogen atom, a cyano group, a halogen atom or an alkyl group which may have a substituent.

Z' represents an atomic group for forming an alicyclic structure containing two bonded carbon atoms (C—C), which may have a substituent.

Examples of the halogen atom of $R_{11}'$ and $R_{12}'$ include a chlorine atom, a bromine atom, a fluorine atom and an iodine atom.

The alkyl group of $R_{11}'$, $R_{12}'$ and $R_{21}'$ to $R_{30}'$ is preferably a linear or branched alkyl group having from 1 to 10 carbon atoms, more preferably a linear or branched alkyl group having from 1 to 6 carbon atoms, still more preferably a methyl group, an ethyl group, a propyl group, an isopropyl group, a n-butyl group, an isobutyl group, a sec-butyl group or a tert-butyl group.

Examples of the substituent which is further substituted to the alkyl group include a hydroxyl group, a halogen atom, a carboxyl group, an alkoxy group, an acyl group, a cyano group and an acyloxy group. Examples of the halogen atom include a chlorine atom, a bromine atom, a fluorine atom and an iodine atom, examples of the alkoxy group include an alkoxy group having from 1 to 4 carbon atoms, such as methoxy group, ethoxy group, propoxy group and butoxy group, examples of the acyl group include a formyl group and an acetyl group, and examples of the acyloxy group include an acetoxy group.

The atomic group for forming an alicyclic structure, represented by Z', is an atomic group for forming a repeating unit of alicyclic hydrocarbon which may have a substituent, in the resin and among these atomic groups, preferred are an atomic group for forming a crosslinked alicyclic structure to form a crosslinked alicyclic hydrocarbon repeating unit.

Examples of the skeleton of alicyclic hydrocarbon formed are the same as those of the alicyclic hydrocarbon group of $R_{11}$ to $R_{25}$ in formulae (pI) to (pVI).

The alicyclic hydrocarbon skeleton may have a substituent and examples of the substituent include $R_{13}'$ to $R_{16}'$ in formulae (II-A) and (II-B).

Among the crosslinked alicyclic hydrocarbon repeating units, the repeating units represented by formulae (II-A) and (II-B) are more preferred.

In the alicyclic hydrocarbon-base acid decomposable resin for use in the present invention, the acid decomposable group may be contained in the —C(═O)—X—A'—$R_{17}$' or may be contained as the substituent of Z' in formula (II-AB).

The structure of the acid decomposable group is represented by —C(═O)—$X_1$—$R_o$.

In this formula, $R_o$ represents, for example, a tertiary alkyl group such as tert-butyl group and tert-amyl group, a 1-alkoxyethyl group such as isoboronyl group, 1-ethoxyethyl group, 1-butoxyethyl group, 1-isobutoxyethyl group and 1-cyclohexyloxyethyl group, an alkoxymethyl group such as 1-methoxymethyl group and 1-ethoxymethyl group, a 3-oxoalkyl group, a tetrahydropyranyl group, a tetrahydrofuranyl group, a trialkylsilylester group, a 3-oxocyclohexylester group, a 2-methyl-2-adamantyl group or a mevalonic lactone residue, and $X_1$ has the same meaning as X above.

Examples of the halogen atom of $R_{13}'$ to $R_{16}'$ include a chlorine atom, a bromine atom, a fluorine atom and an iodine atom.

The alkyl group of $R_5$, $R_6$ and $R_{13}'$ to $R_{16}'$ is preferably a linear or branched alkyl group having from 1 to 10 carbon atoms, more preferably a linear or branched alkyl group having from 1 to 6 carbon atoms, still more preferably a methyl group, an ethyl group, a propyl group, an isopropyl group, a n-butyl group, an isobutyl group, a sec-butyl group or a tert-butyl group.

The cyclic hydrocarbon group of $R_5$, $R_6$ and $R_{13}'$ to $R_{16}'$ is, for example, a cyclic alkyl group or a crosslinked hydrocarbon and examples thereof include a cyclopropyl group, a cyclopentyl group, a cyclohexyl group, an adamantyl group, a 2-methyl-2-adamantyl group, a norbornyl group, a boronyl group, an isoboronyl group, a tricyclodecanyl group, a dicyclopentenyl group, a norbornane epoxy group, a menthyl group, an isomenthyl group, a neomenthyl group and a tetracyclododecanyl group.

The ring formed by the combining of at least two of $R_{13}'$ to $R_{16}'$ includes a ring having from 5 to 12 carbon atoms, such as cyclopentene, cyclohexene, cycloheptane and cyclooctane.

The alkoxy group of $R_{17}'$ includes an alkoxy group having from 1 to 4 carbon atoms such as methoxy group, ethoxy group, propoxy group and butoxy group.

Examples of the substituent which is further substituted to the alkyl group, cyclic hydrocarbon group and alkoxy group include a hydroxyl group, a halogen atom, a carboxyl group, an alkoxy group, an acyl group, a cyano group, an acyloxy group, an alkyl group and a cyclic hydrocarbon group. Examples of the halogen atom include a chlorine atom, a bromine atom, a fluorine atom and an iodine atom, examples of the alkoxy group include an alkoxy group having from 1 to 4 carbon atoms, such as methoxy group, ethoxy group, propoxy group and butoxy group, examples of the acyl group include a formyl group and an acetyl group, and examples of the acyloxy group include an acetoxy group.

Examples of the alkyl group and cyclic hydrocarbon group include those described above.

The divalent group of A' includes a sole group or a combination of two or more groups, selected from the group consisting of an alkylene group, a substituted alkylene group, an ether group, a thioether group, a carbonyl group, an ester group, an amido group, a sulfonamido group, a urethane group and a urea group.

In the alicyclic hydrocarbon-base acid decomposable resin for use in the present invention, the group of decomposing under the action of an acid may be contained in at least one repeating unit out of the repeating unit having a partial structure containing an alicyclic hydrocarbon represented by any one of formulae (pI) to (pVI), the repeating unit represented by formula (II-AB), and the repeating unit of a copolymerization component which is described later.

Various substituents $R_{13}'$ to $R_{16}'$ in formulae (II-A) and (II-B) work out to the substituents of an atomic group for forming an alicyclic structure in formula (II-AB) or an atomic group Z for forming a crosslinked alicyclic structure.

Specific examples of the repeating units represented by formulae (II-A) and (II-B) are set forth below, but the present invention is not limited to these specific examples.

[II-1]

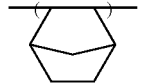

-continued
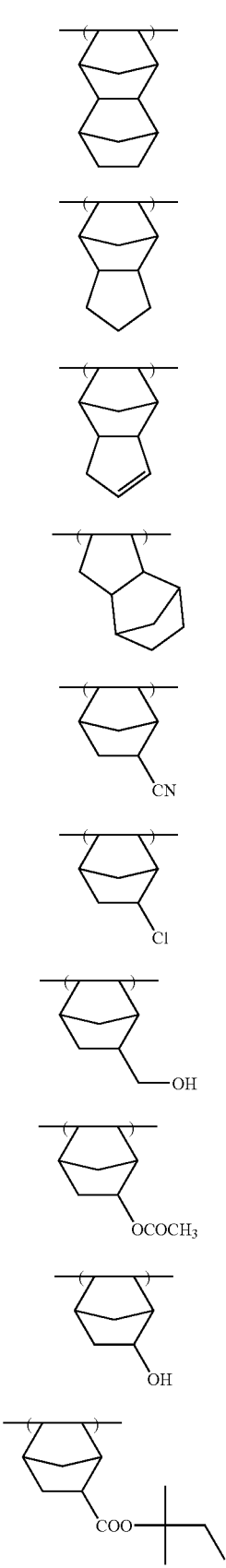
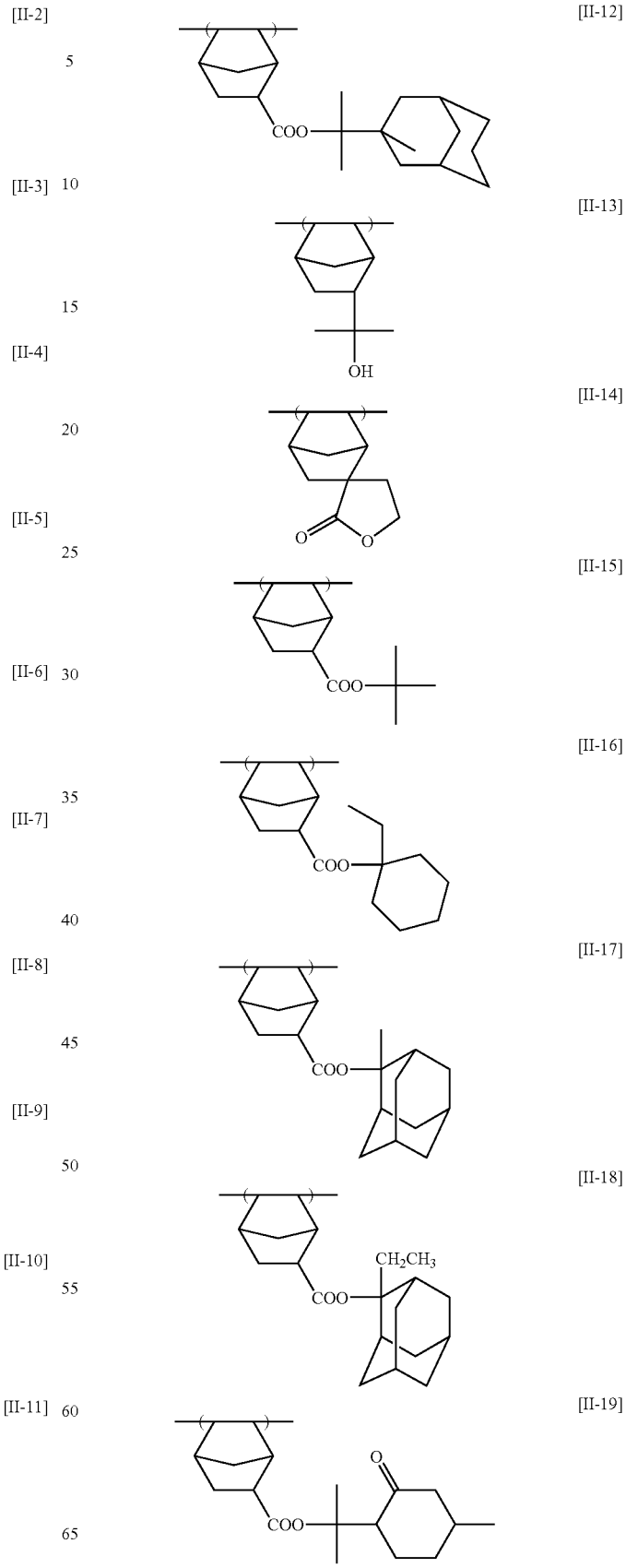

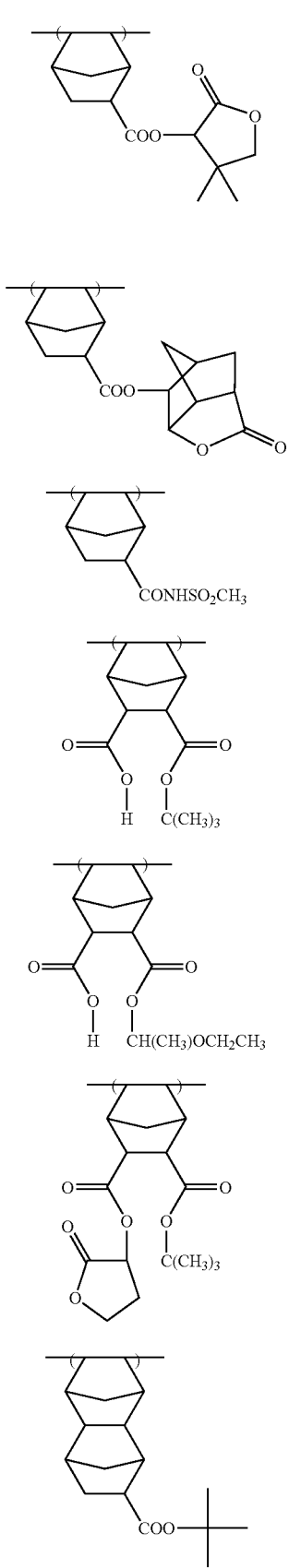
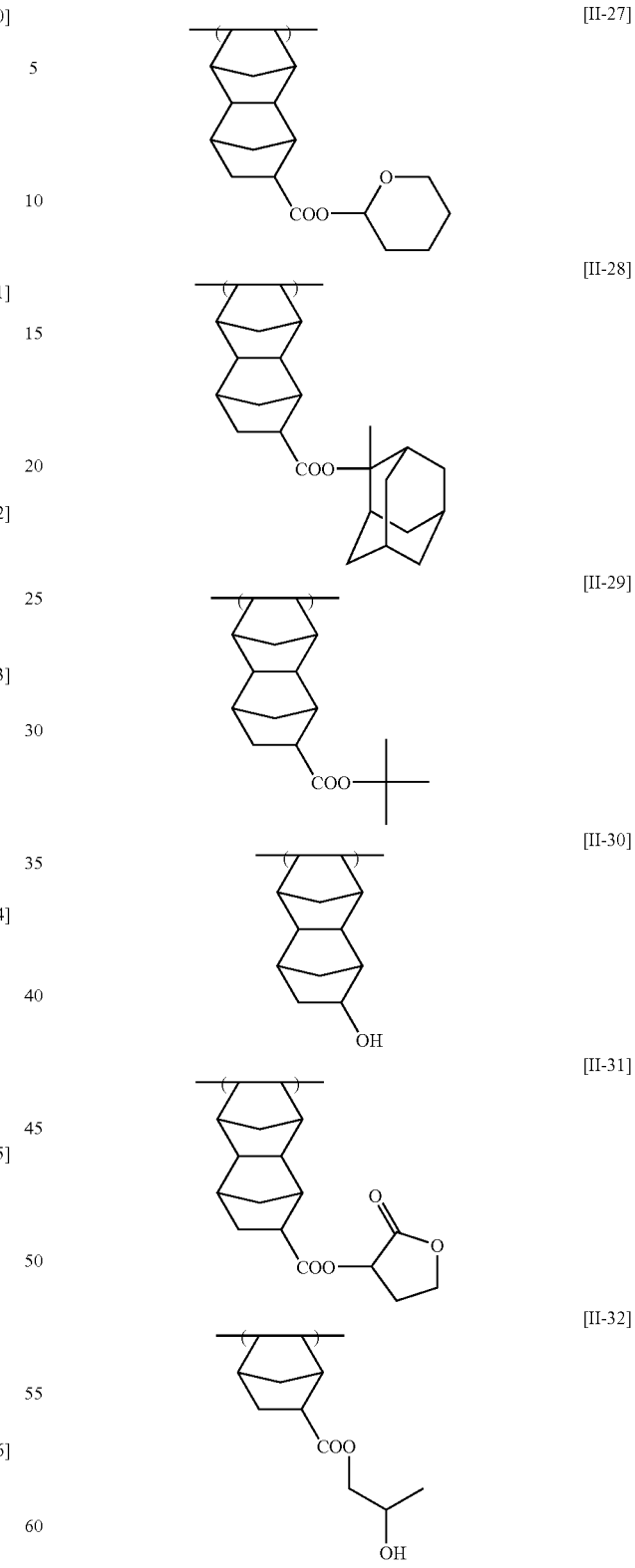
The alicyclic hydrocarbon-base acid decomposable resin for use in the present invention preferably has a lactone group, more preferably a repeating unit containing a group having a lactone structure represented by the following formulae (Lc) or by any one of (V-1) to (V-5), and the group having a lactone structure may be bonded directly to the main chain.

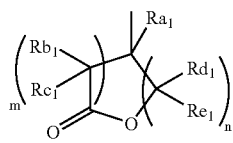
(Lc)

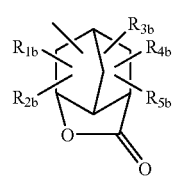
(V-1)

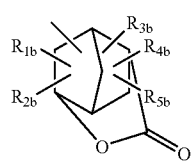
(V-2)

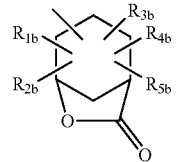
(V-3)

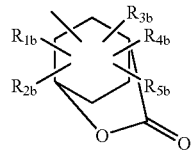
(V-4)

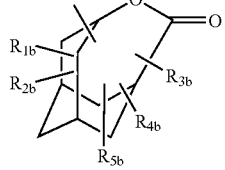
(V-5)

In formula (Lc), $R_{a1}$, $R_{b1}$, $R_{c1}$, $R_{d1}$ and $R_{e1}$ each independently represents a hydrogen atom or an alkyl group, m and n each independently represents an integer of 0 to 3, and m+n is from 2 to 6.

In formulae (V-1) to (V-5), $R_{1b}$ to $R_{5b}$ each independently represents a hydrogen atom, an alkyl group, a cycloalkyl group, an alkoxy group, an alkoxycarbonyl group, an alkylsulfonylimino group or an alkenyl group, and two of $R_{1b}$ to $R_{5b}$ may combine to form a ring.

The alkyl group of $R_{a1}$ to $R_{e1}$ in formula (Lc) and the alkyl group in the alkyl group, alkoxy group, alkoxy-carbonyl group and alkylsulfonylimino group of $R_{1b}$ to $R_{5b}$ in formulae (V-1) to (V-5) include a linear or branched alkyl group and may have a substituent.

Examples of the repeating unit having a lactone structure represented by formula (Lc) or by any one of formulae (V-1) to (V-5) include a repeating unit where at least one of $R_{13}'$ to $R_{16}'$ in formula (II-A) or (II-B) has a group represented by formula (Lc) or by any one of formulae (V-1) to (V-5) (for example, when $R_5$ of —COOR$_5$ is a group represented by formula (Lc) or by any one of formulae (V-1) to (V-5)), and a repeating unit represented by the following formula (AI):

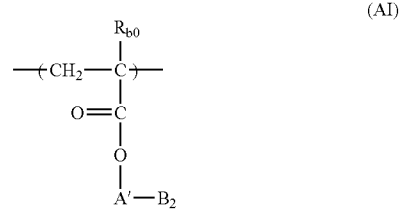
(AI)

In formula (AI), $R_{b0}$ represents a hydrogen atom, a halogen atom or a substituted or unsubstituted alkyl group having from 1 to 4 carbon atoms. Preferred examples of the substituent which may be substituted to the alkyl group of $R_{b0}$ include those described above as preferred examples of the substituent which may be substituted to the alkyl group of $R_{1b}$ in formulae (V-1) to (V-5).

Examples of the halogen atom of $R_{b0}$ include a fluorine atom, a chlorine atom, a bromine atom and an iodine atom. $R_{b0}$ is preferably a hydrogen atom.

A' represents a single bond, an ether group, an ester group, a carbonyl group, an alkylene group or a divalent group comprising a combination thereof.

$B_2$ represents a group represented by formula (Lc) or by any one of formulae (V-1) to (V-5).

Specific examples of the repeating unit containing a group having a lactone structure are set forth below, but the present invention is not limited thereto.

(In formulae, Rx is H, CH$_3$ or CF$_3$.)

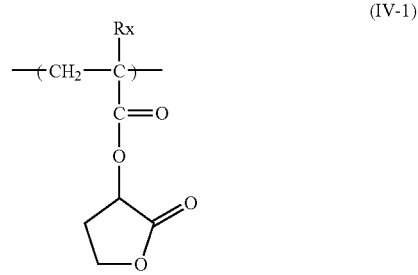
(IV-1)

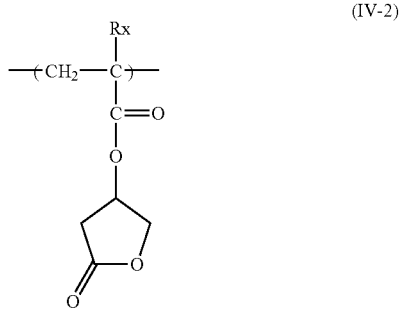
(IV-2)

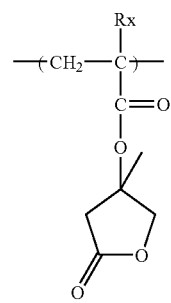
(IV-3)
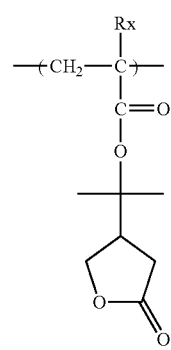
(IV-4)
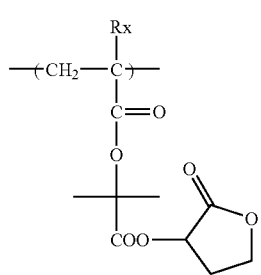
(IV-5)
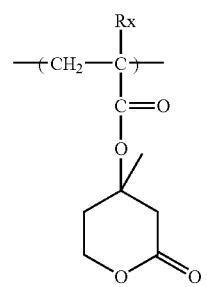
(IV-6)
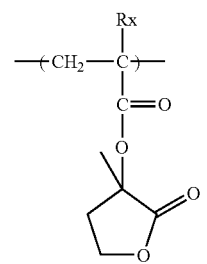
(IV-7)
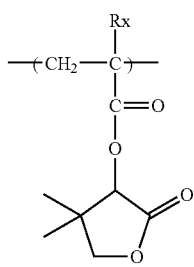
(IV-8)
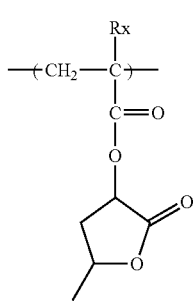
(IV-9)
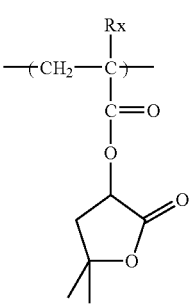
(IV-10)
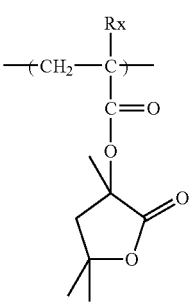
(IV-11)
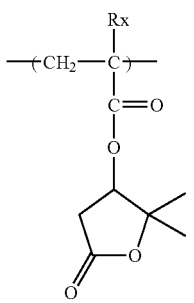
(IV-12)

(IV-13) 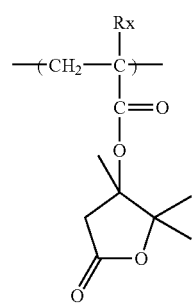
(IV-14) 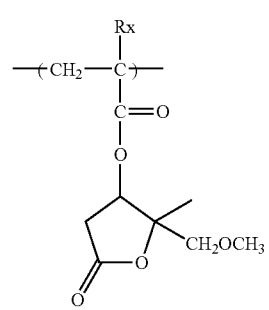
(IV-15) 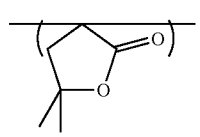
(IV-16) 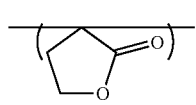
(In Formulae, Rx is H, CH₃ or CF₃.)
(Ib-1) 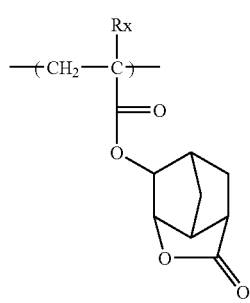
(Ib-2) 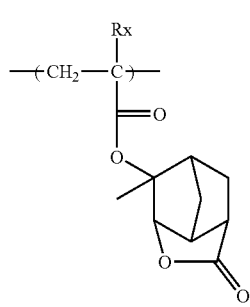
(Ib-3) 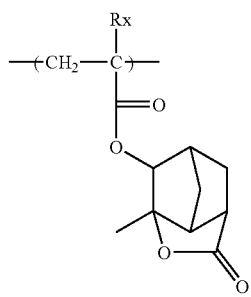
(Ib-4) 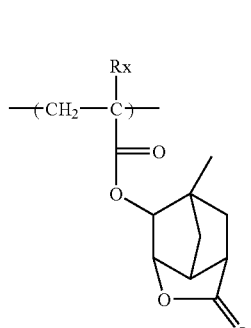
(Ib-5) 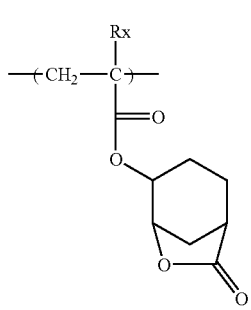
(Ib-6) 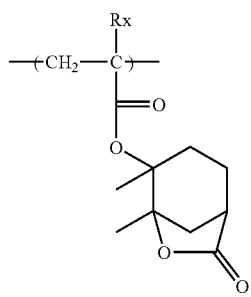
(Ib-7) 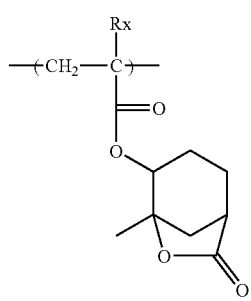

(Ib-8)
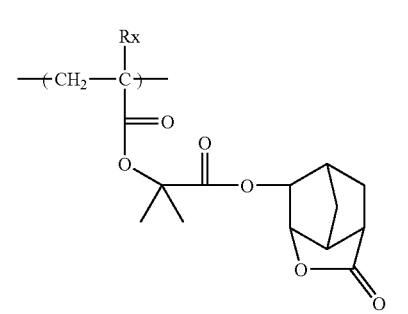
(Ib-9)
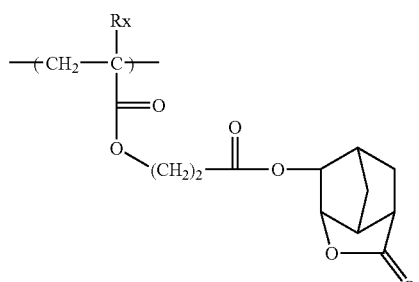
(Ib-10)
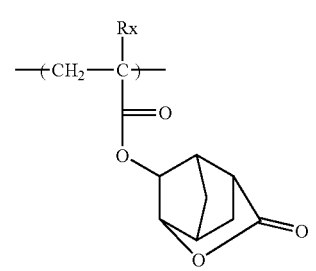
(Ib-11)
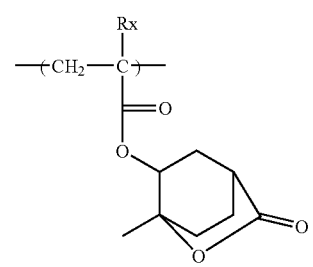
(In formulae, Rx is H, CH₃ or CF₃.)
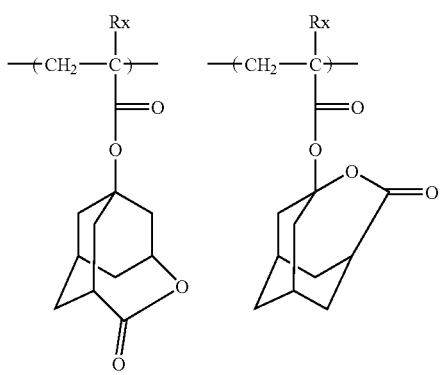
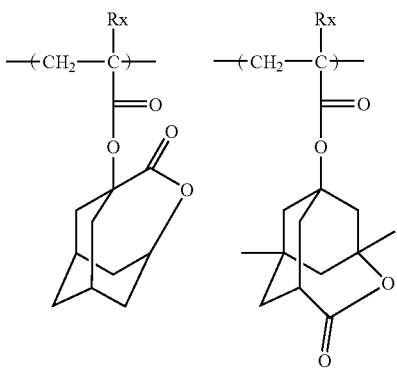
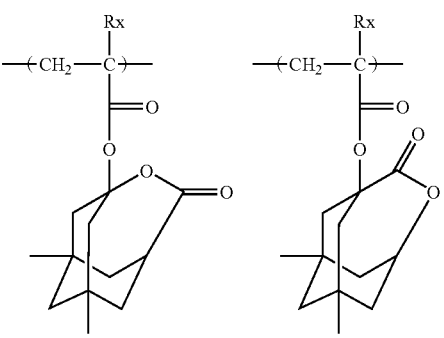
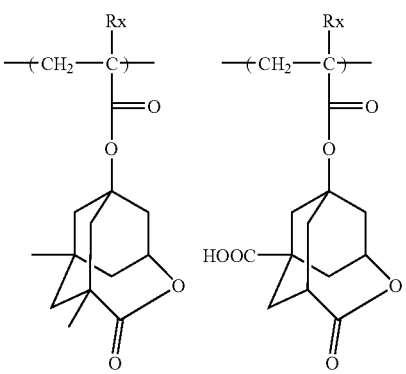
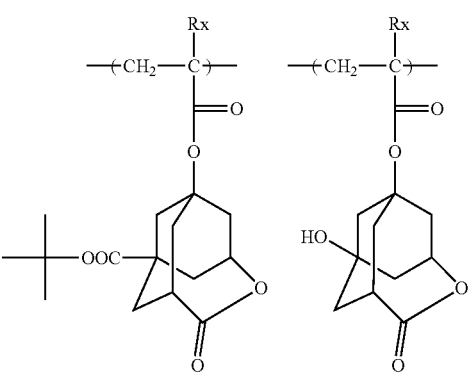

-continued

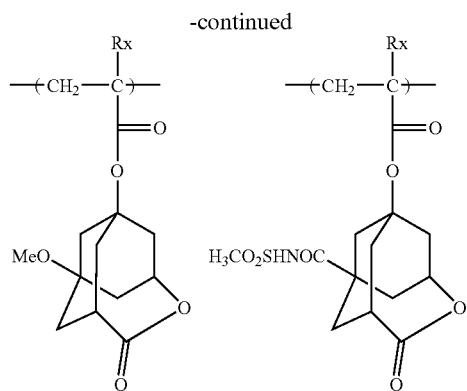

The alicyclic hydrocarbon-base acid decomposable resin for use in the present invention may contain a repeating unit having a group represented by the following formula (VII):

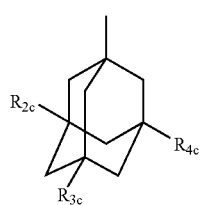

wherein $R_{2c}$ to $R_{4c}$ each independently represents a hydrogen atom or a hydroxyl group, provided that at least one of $R_{2c}$ to $R_{4c}$ represents a hydroxyl group.

The group represented by formula (VII) is preferably a dihydroxy form or a monohydroxy form, more preferably a dihydroxy form.

Examples of the repeating unit having a group represented by formula (VII) include a repeating unit where at least one of $R_{13}'$ to $R_{16}'$ in formula (II-A) or (II-B) has a group represented by formula (VII) (for example, when $R_5$ in —$COOR_5$ is a group represented by formula (VII)), and a repeating unit represented by the following formula (AII):

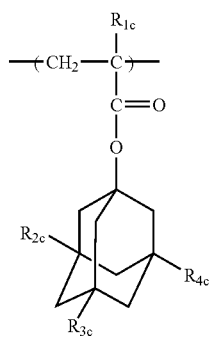

wherein $R_{1c}$ represents a hydrogen atom or a methyl group, and $R_{2c}$ to $R_{4c}$ each independently represents a hydrogen atom or a hydroxyl group, provided that at least one of $R_{2c}$ to $R_{4c}$ represents a hydroxyl group. A repeating unit where two of $R_{2c}$ to $R_{4c}$ are a hydroxyl group is preferred.

Specific examples of the repeating unit having the structure represented by formula (AII) are set forth below, but the present invention is not limited thereto.

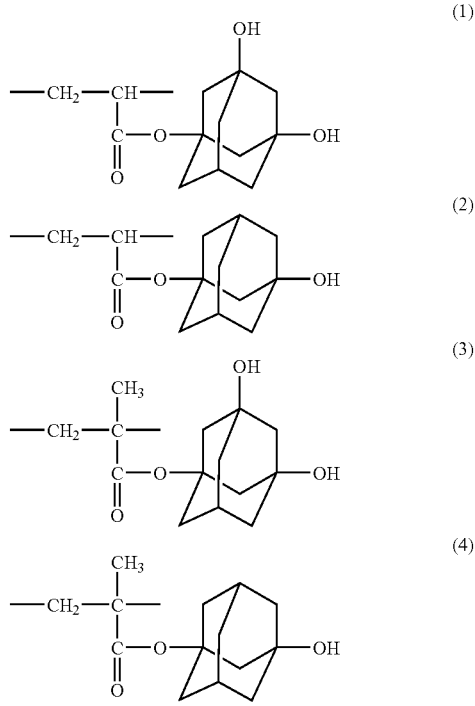

The alicyclic hydrocarbon-base acid decomposable resin for use in the present invention may contain a repeating unit represented by the following formula (VIII):

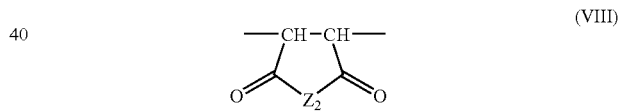

wherein $Z_2$ represents —O— or —N($R_{41}$)—, $R_{41}$ represents a hydrogen atom, a hydroxyl group, an alkyl group or —$OSO_2$—$R_{42}$, and $R_{42}$ represents an alkyl group, a cycloalkyl group or a camphor residue. The alkyl group of $R_{41}$ and $R_{42}$ may be substituted by a halogen atom (preferably a fluorine atom) or the like.

Specific examples of the repeating unit represented by formula (VIII) are set forth below, but the present invention is not limited thereto.

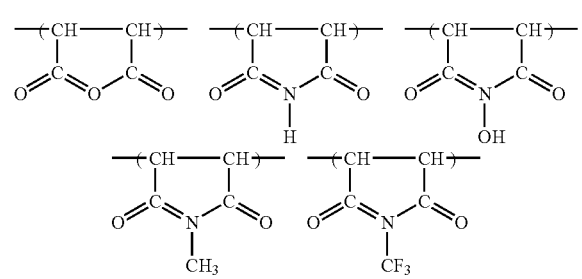

-continued

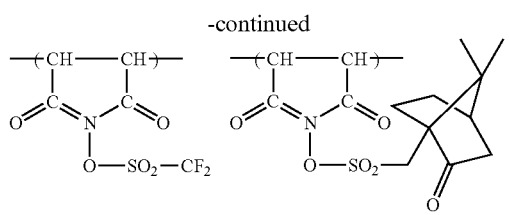

The alicyclic hydrocarbon-base acid decomposable resin for use in the present invention may contain, in addition to the above-described repeating units, various repeating units for the purpose of controlling the dry etching resistance, suitability for standard developer, adhesion to substrate, resist profile and properties generally required of the resist, such as resolution, heat resistance and sensitivity.

Examples of such repeating structural units include repeating structural units corresponding to the monomers described below, but the present invention is not limited thereto.

By containing these repeating structural units, the performance required of the alicyclic hydrocarbon-base acid decomposable resin, particularly, (1) solubility in the coating solvent, (2) film-forming property (glass transition point), (3) alkali developability, (4) film loss (selection of hydrophilic, hydrophobic or alkali-soluble group), (5) adhesion to substrate in unexposed area, (6) dry etching resistance and the like can be subtly controlled.

Examples of the monomer include compounds having one addition polymerizable unsaturated bond, selected from acrylic acid esters, methacrylic acid esters, acrylamides, methacrylamides, allyl compounds, vinyl ethers and vinyl esters.

Other than these, an addition polymerizable unsaturated compound copolymerizable with the monomer corresponding to the above-described various repeating structural units may be copolymerized.

In the alicyclic hydrocarbon-base acid decomposable resin, the molar ratio of each repeating structural unit contained is appropriately determined to control the dry etching resistance of resist, suitability for standard developer, adhesion to substrate, resist profile and performances generally required of the resist, such as resolution, heat resistance and sensitivity.

Preferred embodiments of the alicyclic hydrocarbon-base acid decomposable resin for use in the present invention include:

(1) a resin having a partial structure containing an alicyclic hydrocarbon represented by any one of formulae (pI) to (pVI) (side chain type), and (2) a resin containing a repeating unit represented by formula (II-AB) (main chain type), and the resin of (2) further includes:

(3) a resin having a repeating unit represented by formula (II-AB), a maleic anhydride derivative and a (meth)acrylate structure (hybrid type).

In the alicyclic hydrocarbon-base acid decomposable resin, the content of the repeating unit having an acid decomposable group is preferably from 10 to 60 mol %, more preferably from 20 to 50 mol %, still more preferably from 25 to 40 mol %, based on all repeating structural units.

In the alicyclic hydrocarbon-base acid decomposable resin, the content of the repeating unit having a partial structure containing an alicyclic hydrocarbon represented by any one of formulae (pI) to (pVI) is preferably from 30 to 70 mol %, more preferably from 35 to 65 mol %, still more preferably from 40 to 60 mol %, based on all repeating structural units.

In the alicyclic hydrocarbon-base acid decomposable resin, the content of the repeating unit represented by formula (II-AB) is preferably from 10 to 60 mol %, more preferably from 15 to 55 mol %, still more preferably from 20 to 50 mol %, based on all repeating structural units.

In the resin, the content of the repeating unit based on the monomer as the further copolymerization component can also be appropriately selected according to the desired resist performance, but the content is generally 99 mol % or less, more preferably 90 mol % or less, still more preferably 80 mol % or less, based on the total molar number of the repeating structural unit having a partial structure containing an alicyclic hydrocarbon represented by any one of formulae (pI) to (pVI) and the repeating unit represented by formula (II-AB).

When the composition of the present invention is used for exposure with ArF, the resin preferably has no aromatic group in view of the transparency to ArF light.

The alicyclic hydrocarbon-base acid decomposable resin for use in the present invention can be synthesized by an ordinary method (for example, radical polymerization). In the general synthesis method, for example, monomer species are charged into a reactor all at once or on the way of reaction and dissolved, if desired, in a reaction solvent such as tetrahydrofuran, 1,4-dioxane, ethers (e.g., diisopropyl ether), ketones (e.g., methyl ethyl ketone, methyl isobutyl ketone) and esters (e.g., ethyl acetate), or in a solvent which dissolves the composition of the present invention, such as propylene glycol monomethyl ether acetate which is described later. The obtained uniform solution is, if desired, heated in an inert gas atmosphere such as nitrogen or argon to start the polymerization by using a commercially available radical polymerization initiator (e.g., azo-base initiator, peroxide). If desired, the initiator may be added additionally or in parts. After the completion of reaction, the reactant is poured into a solvent and the desired polymer is recovered, for example, by a powder or solid recovery method. The reaction concentration is usually 20 mass % or more, preferably 30 mass % or more, more preferably 40 mass % or more, and the reaction temperature is from 10 to 150° C., preferably from 30 to 120° C., more preferably from 50 to 100° C.

In the case of using the composition of the present invention for the upper resist of a multilayer resist, the resin of the component (B) preferably has a silicon atom.

As for the resin having a silicon atom and undergoing decomposition under the action of an acid to increase the solubility in an alkali developer, resins having a silicon atom in at least either main chain or side chain all can be used. Examples of the resin having a siloxane structure in the side chain of resin include copolymers of an olefin-base monomer having a silicon atom in the side chain or a (meth) acrylic acid-base monomer having a maleic anhydride and an acid decomposable group in the side chain.

In the case of irradiating $F_2$ excimer laser light on the positive stimulus-sensitive composition of the present invention, the resin of the component (B) is preferably a resin having a structure that a fluorine atom is substituted to the main chain and/or the side chain of the polymer skeleton, and undergoing decomposition under the action of an acid to increase the solubility in an alkali developer (hereinafter sometimes referred to as a "fluorine group-containing resin"), more preferably a resin containing a hydroxyl group with the 1-position being substituted by a fluorine atom or a fluoroalkyl group, or a group where the hydroxyl group with the 1-position being substituted by a fluorine atom or a fluoroalkyl group is protected by an acid decomposable group, and most preferably a resin containing a hexafluoro-2-propanol structure or a structure that the hydroxyl group of hexafluoro-2-propanol is protected by an acid decomposable group. By introducing a fluorine atom, the transparency to far ultraviolet light, particularly $F_2$ (157 nm) light, can be enhanced.

Preferred examples of the fluorine group-containing resin in the acid decomposable resin (B) include a resin having at least one repeating unit represented by the following formulae (FA) to (FG):

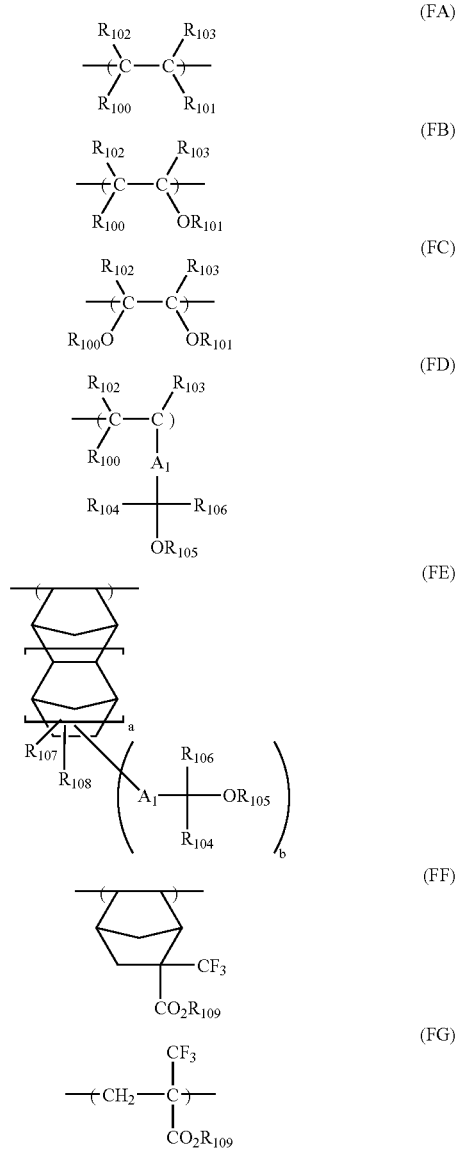

In these formulae, $R_{100}$ to $R_{103}$ each represents a hydrogen atom, a fluorine atom, an alkyl group or an aryl group.

$R_{104}$ and $R_{106}$ each is a hydrogen atom, a fluorine atom or an alkyl group and at least one of $R_{104}$ and $R_{106}$ is a fluorine atom or a fluoroalkyl group. $R_{104}$ and $R_{106}$ are preferably both a trifluoromethyl group.

$R_{105}$ is a hydrogen atom, an alkyl group, an acyl group, an alkoxycarbonyl group or a group of decomposing under the action of an acid.

$A_1$ is a single bond or a divalent linking group, for example, a linear, branched or cyclic alkylene group, an alkenylene group, an arylene group, —OCO—, —COO—, —CON($R_{24}$)— or a linking group containing multiple members thereof. $R_{24}$ is a hydrogen atom or an alkyl group.

$R_{107}$ and $R_{108}$ each is a hydrogen atom, a halogen atom, an alkyl group, an alkoxy group, an alkoxycarbonyl group or a group of decomposing under the action of an acid.

$R_{109}$ is a hydrogen atom, an alkyl group or a group of decomposing under the action of an acid.

b is 0, 1 or 2.

The repeating units represented by formulae (FA) to (FG) each contains at least one fluorine atom, preferably three or more fluorine atoms, per one repeating unit.

In formulae (FA) to (FG), the alkyl group is preferably an alkyl group having from 1 to 8 carbon atoms and specific examples thereof include a methyl group, an ethyl group, a propyl group, an n-butyl group, a sec-butyl group, a hexyl group, a 2-ethylhexyl group and an octyl group.

The cycloalkyl group may be monocyclic or polycyclic. The monocyclic type is preferably a cycloalkyl group having from 3 to 8 carbon atoms and examples thereof include a cyclopropyl group, a cyclopentyl group, a cyclohexyl group, a cycloheptyl group and a cyclooctyl group. The polycyclic type is preferably a cycloalkyl group having from 6 to 20 carbon atoms and examples thereof include an adamantyl group, a norbornyl group, an isoboronyl group, a camphanyl group, a dicyclopentyl group, an α-pinel group, a tricyclodecanyl group, a tetracyclododecyl group and an androstanyl group. In these monocyclic or polycyclic cycloalkyl groups, the carbon atom may be substituted by a heteroatom such as oxygen atom.

The fluoroalkyl group is preferably a fluoroalkyl group having from 1 to 12 carbon atoms and specific examples thereof include a trifluoromethyl group, a perfluoroethyl group, a perfluoropropyl group, a perfluorobutyl group, a perfluorohexyl group, a perfluorooctyl group, a perfluorooctylethyl group and a perfluorododecyl group.

The aryl group is preferably an aryl group having from 6 to 15 carbon atoms and specific examples thereof include a phenyl group, a tolyl group, a dimethylphenyl group, a 2,4,6-trimethylphenyl group, a naphthyl group, an anthryl group and a 9,10-dimethoxyanthryl group.

The aralkyl group is preferably an aralkyl group having from 7 to 12 carbon atoms and specific examples thereof include a benzyl group, a phenethyl group and a naphthylmethyl group.

The alkenyl group is preferably an alkenyl group having from 2 to 8 carbon atoms and specific examples thereof include a vinyl group, an allyl group, a butenyl group and a cyclohexenyl group.

The alkoxy group is preferably an alkoxy group having from 1 to 8 carbon atoms and specific examples thereof include a methoxy group, an ethoxy group, an n-propoxy group, an iso-propoxy group, a butoxy group, a pentoxy group, an allyloxy group and an octoxy group.

The acyl group is preferably an acyl group having from 1 to 10 carbon atoms and specific examples thereof include a formyl group, an acetyl group, a propanoyl group, a butanoyl group, a pivaloyl group, an octanoyl group and a benzoyl group.

The acyloxy group is preferably an acyloxy group having from 2 to 12 carbon atoms and examples thereof include an acetoxy group, a propionyloxy group and a benzoyloxy group.

The alkynyl group is preferably an alkynyl group having from 2 to 5 carbon atoms and examples thereof include an ethynyl group, a propynyl group and a butynyl group.

The alkoxycarbonyl group is preferably a secondary alkoxycarbonyl group, more preferably a tertiary alkoxycarbonyl group, and examples thereof include an i-propoxycarbonyl group, a tert-butoxycarbonyl group, a tert-amyloxycarbonyl group and a 1-methyl-1-cyclohexyloxycarbonyl group.

The halogen atom includes, for example, a fluorine atom, a chlorine atom, a bromine atom and an iodine atom.

The alkylene group is preferably an alkylene group having from 1 to 8 carbon atoms, which may have a substituent, and examples thereof include a methylene group, an ethylene group, a propylene group, a butylene group, a hexylene group and an octylene group.

The alkenylene group is preferably an alkenylene group having from 2 to 6 carbon atoms, which may have a substituent, and examples thereof include an ethenylene group, a propenylene group and a butenylene group.

The cycloalkylene group is preferably a cycloalkylene group having from 5 to 8 carbon atoms, which may have a substituent, and examples thereof include a cyclopentylene group and a cyclohexylene group.

The arylene group is preferably an arylene group having from 6 to 15 carbon atoms, which may have a substituent, and examples thereof include a phenylene group, a tolylene group and a naphthylene group.

These groups each may have a substituent and examples of the substituent include those having an active hydrogen, such as alkyl group, cycloalkyl group, aryl group, amino group, amido group, ureido group, urethane group, hydroxyl group and carboxyl group, a halogen atom (e.g., fluorine, chlorine, bromine, iodine), an alkoxy group (e.g., methoxy, ethoxy, propoxy, butoxy), a thioether group, an acyl group (e.g., acetyl, propanoyl, benzoyl), an acyloxy group (e.g., acetoxy, propanoyloxy, benzoyloxy), an alkoxycarbonyl group (e.g., methoxycarbonyl, ethoxycarbonyl, propoxycarbonyl), a cyano group and a nitro group.

The alkyl group, the cycloalkyl group and the aryl group include those described above, and the alkyl group may be further substituted by a fluorine atom or a cycloalkyl group.

Examples of the group of decomposing under the action of an acid to exhibit alkali solubility, which is contained in the fluorine group-containing resin of the present invention, include —O—C($R_{36}$)($R_{37}$)($R_{38}$), —O—C($R_{36}$)($R_{37}$)($R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($OR_{38}$) and —COO—C($R_{36}$)($R_{37}$)($OR_{39}$).

$R_{36}$ to $R_{39}$ each represents an alkyl, cycloalkyl, aryl, aralkyl or alkenyl group which may have a substituent, and $R_{01}$ and $R_{02}$ each represents a hydrogen atom or an alkyl, cycloalkyl, alkenyl, aralkyl or aryl group which may have a substituent.

Specific preferred examples include an ether or ester group of a tertiary alkyl group such as tert-butyl group, tert-amyl group, 1-alkyl-1-cyclohexyl group, 2-alkyl-2-adamantyl group, 2-adamantyl-2-propyl group and 2-(4-methylcyclohexyl)-2-propyl group, an acetal or acetal ester group such as 1-alkoxy-1-ethoxy group and tetrahydropyranyl group, a tert-alkylcarbonate group and a tert-alkylcarbonylmethoxy group.

Specific examples of the repeating structural units represented by formulae (FA) to (FG) are set forth below, but the present invention is not limited thereto.

(F-1)

(F-2)

(F-3)

(F-4)

(F-5)

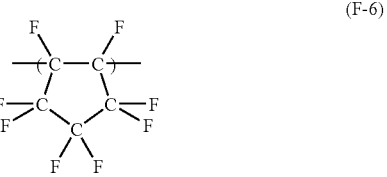
(F-6)

(F-7)

(F-8)

(F-9)

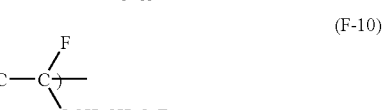
(F-10)

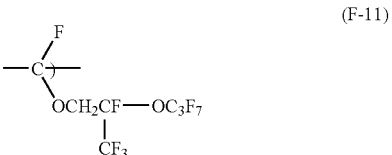
(F-11)

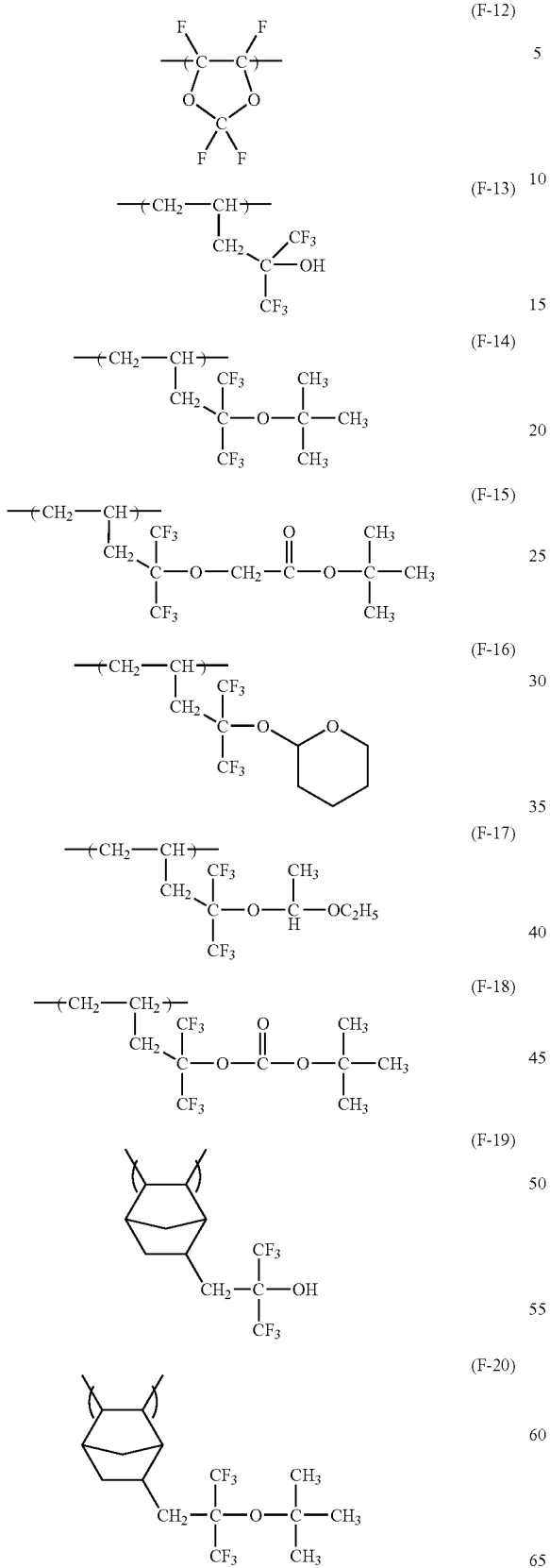
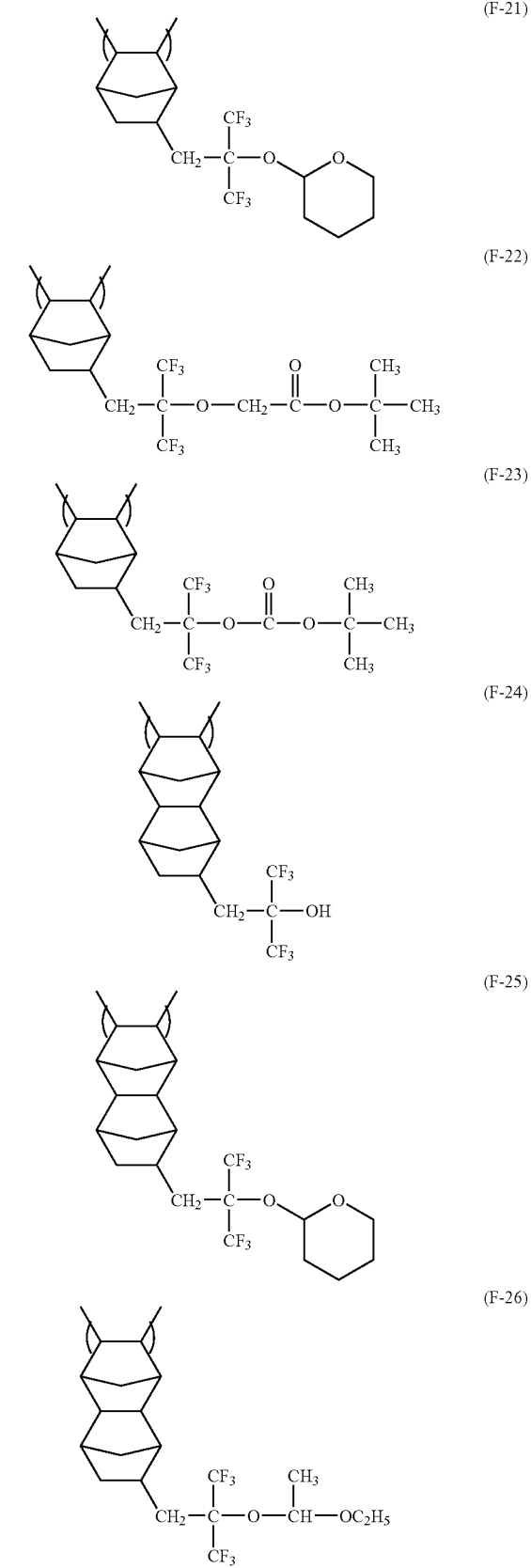

-continued
(F-27)
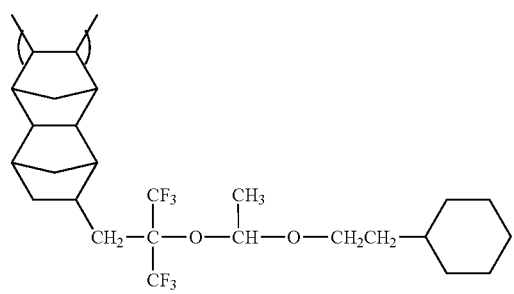
(F-28)
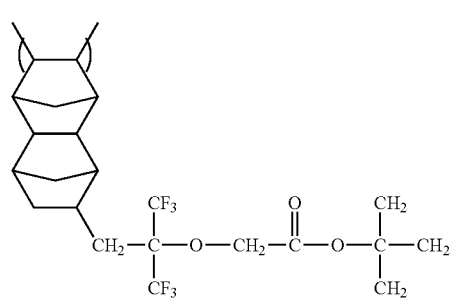
(F-29)
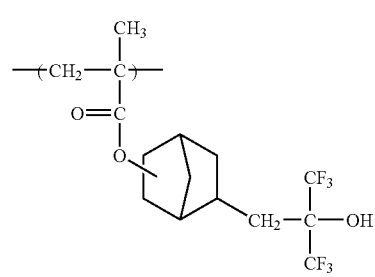
(F-30)
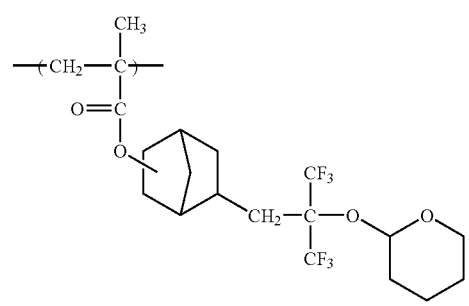
(F-31)
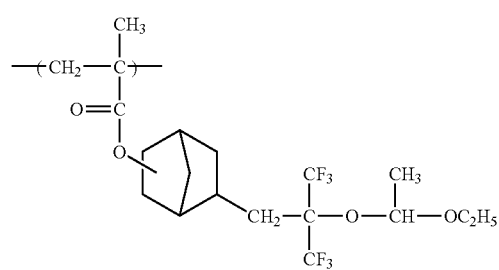
-continued
(F-32)
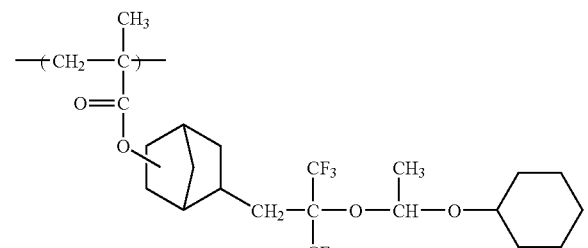
(F-33)
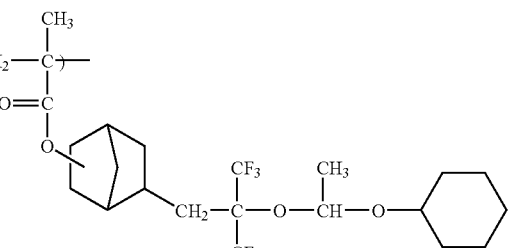
(F-34)
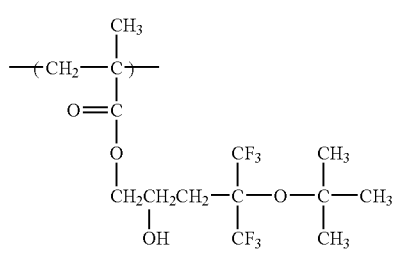
(F-35)
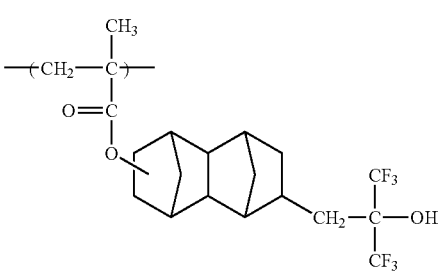
(F-36)
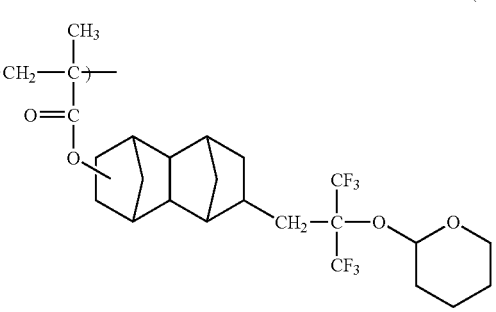

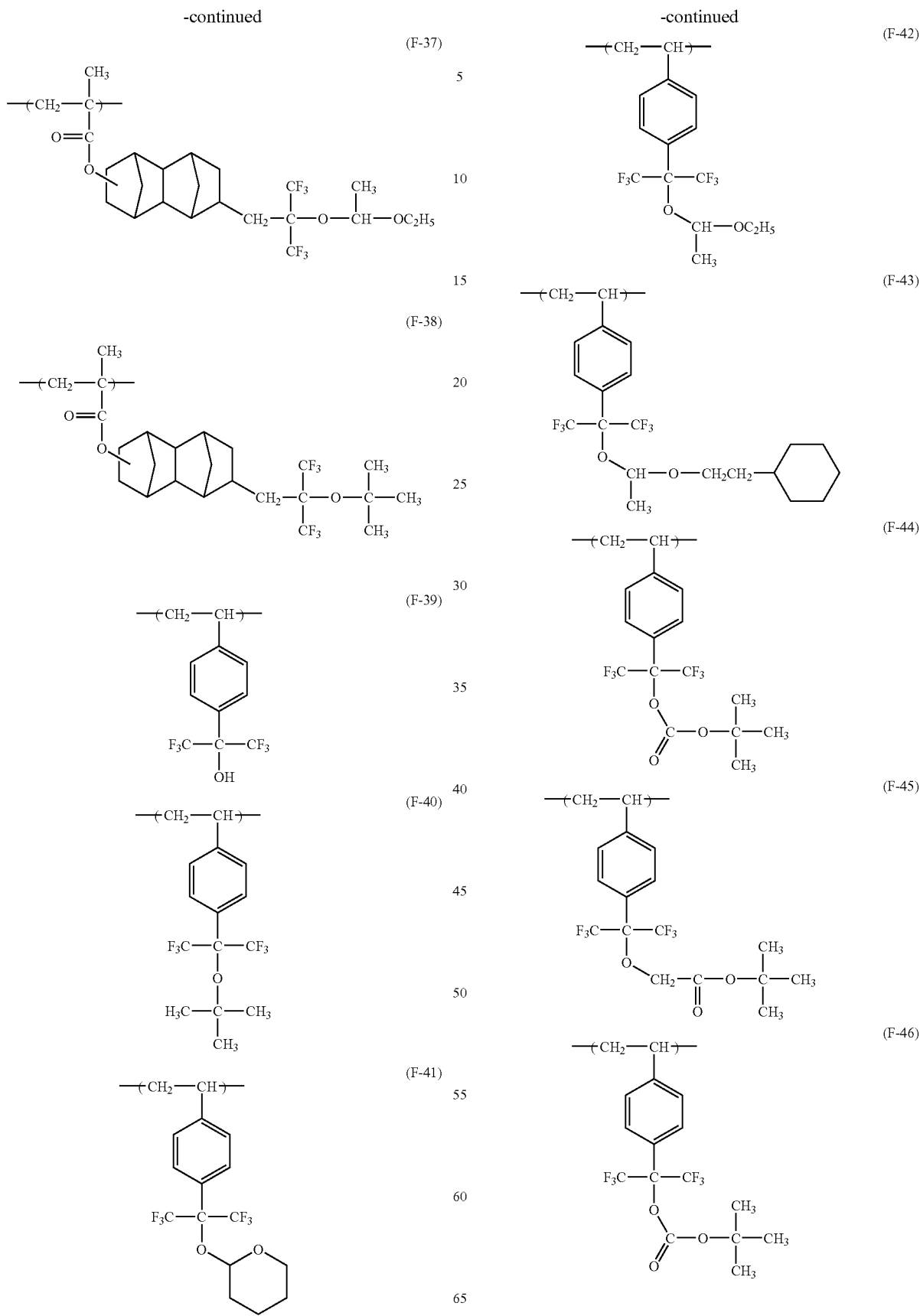

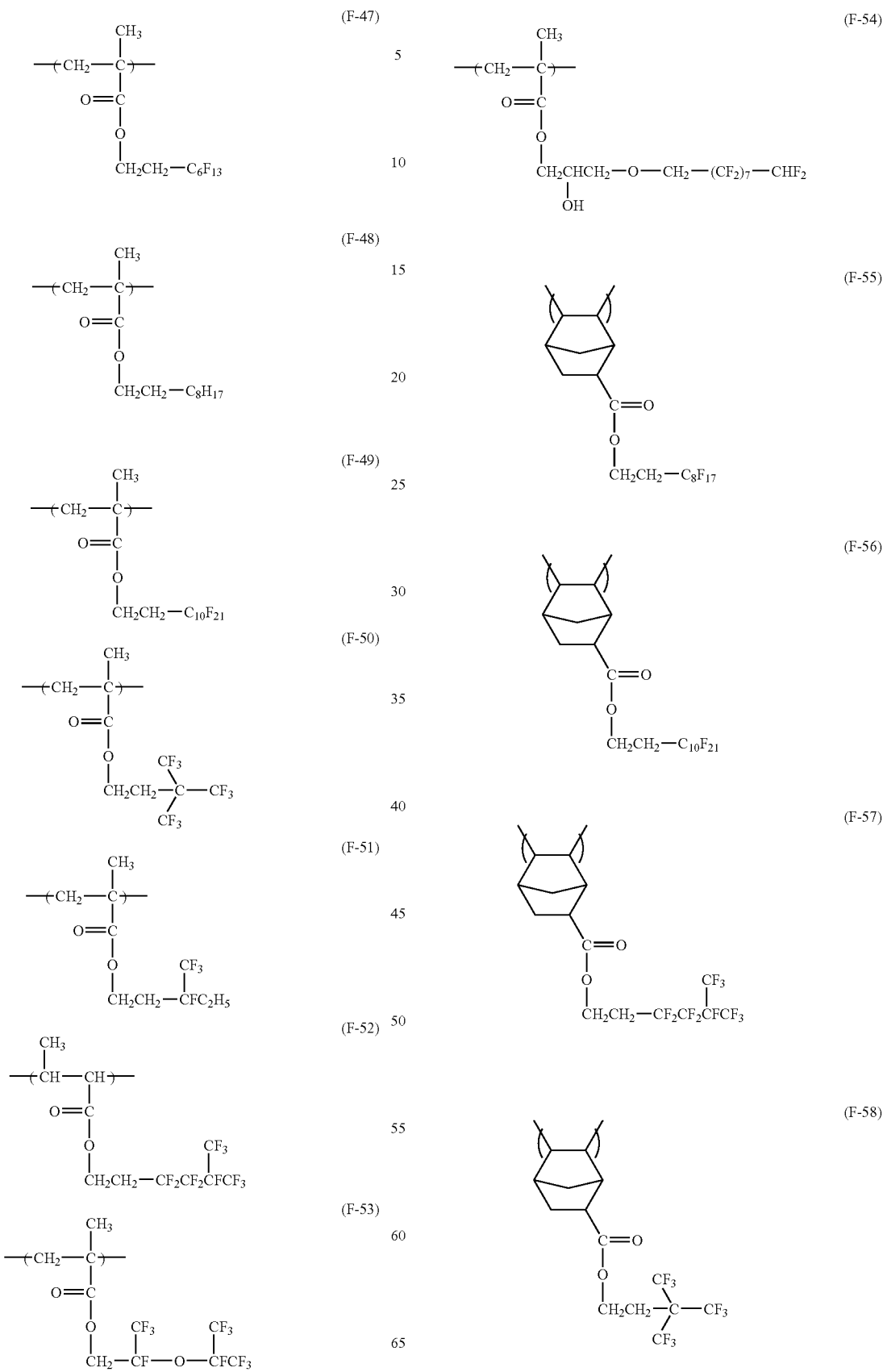

-continued (F-59) 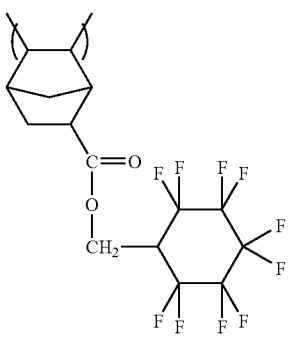

(F-60) 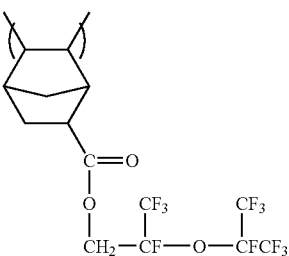

(F-61) 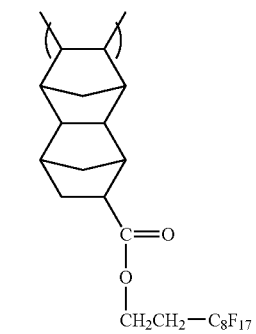

(F-62) 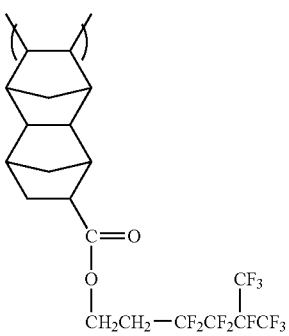

(F-63) 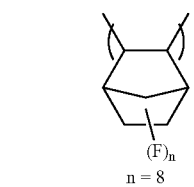

n = 8

(F-64) 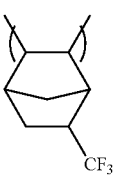

-continued (F-65) 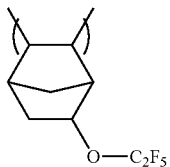

The total content of the repeating units represented by formulae (FA) to (FG) is generally from 10 to 80 mol %, preferably from 30 to 70 mol %, more preferably from 35 to 65 mol %, based on all repeating units constituting the resin.

In the resin of (B) for use in the present invention, in addition to these repeating structural units, other polymerizable monomers may be copolymerized for the purpose of enhancing the performance of resist of the present invention.

Examples of the copolymerization monomer which can be used include compounds having one addition polymerizable unsaturated bond, selected from acrylic acid esters other than those described above, methacrylic acid esters, acrylamides, methacrylamides, allyl compounds, vinyl ethers, vinyl esters, styrenes and crotonic acid esters.

From the standpoint of enhancing the dry etching resistance, controlling the alkali solubility and increasing the adhesive property to substrate, the fluorine-containing resin preferably contains another repeating unit in addition to the above-described fluorine atom-containing repeating unit. Preferred examples of the another repeating unit include:

1) repeating units having an alicyclic hydrocarbon structure represented by formulae (pI) to (pVI) and (II-AB); specifically, repeating units 1 to 23 and repeating units [II-1] to [II-32]; preferably repeating units 1 to 23 where Rx is $CF_3$;

2) repeating units having a lactone structure represented by formulae (Lc) and (V-1) to (V-5); specifically, repeating units (IV-1) to (IV-16) and repeating units (Ib-1) to (Ib-11);

3) repeating units represented by the following formulae (XV), (XVI) and (XVII); specifically repeating units (C-1) to (C-15).

In these repeating units, a fluorine atom may not be contained.

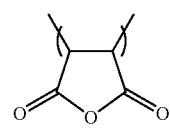 (XV)

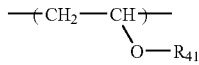 (XVI)

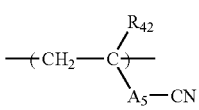 (XVII)

wherein $R_{41}$ represents an alkyl group, a cycloalkyl group, an aralkyl group or an aryl group, and $R_{41}$ may be substituted by an aryl group, $R_{42}$ represents a hydrogen atom, a halogen atom, a cyano group or an alkyl group, $A_5$ represents a single bond, a divalent alkylene, alkenylene, cycloalkylene or arylene group, —O—CO—$R_{22}$, —CO—O—$R_{23}$— or —CO—N($R_{24}$)—$R_{25}$—, $R_{22}$, $R_{23}$ and $R_{25}$, which may be the same or different, each represents a single bond or a divalent alkylene, alkenylene, cycloalkylene or arylene group which may have an ether group, an ester group, an amide group, a urethane group or a ureido group, $R_{24}$ represents a hydrogen atom or an alkyl, cycloalkyl, aralkyl or aryl group which may have a substituent, n represents 0 or 1, and x, y and z each represents an integer of 0 to 4.

Examples of each substituent are the same as those described above for the substituents of formula (FA) to (FG).

Specific examples of the repeating structural units represented by formulae (XVI) to (XVII) are set forth below, but the present invention is not limited thereto.

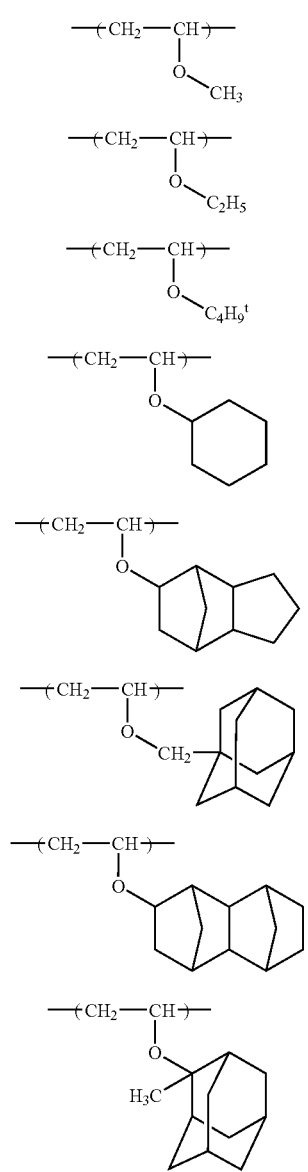

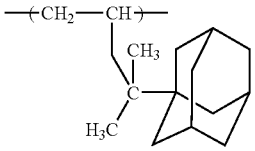

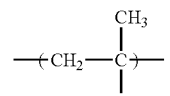

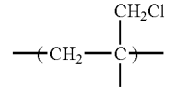

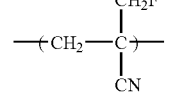

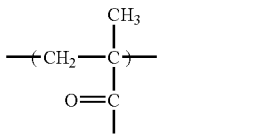

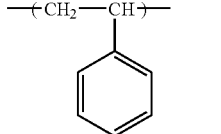

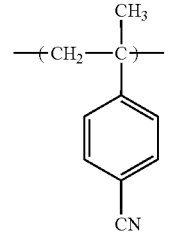

The content of the another repeating unit such as repeating units represented by formulae (XV) to (XVII) is generally from 0 to 70 mol %, preferably from 10 to 60 mol %, more preferably from 20 to 50 mol %, based on all repeating units constituting the resin.

The fluorine group-containing resin as the acid decomposable resin (B) may be contained in any repeating unit.

The content of the repeating unit having an acid decomposable group is from 10 to 70 mol %, preferably from 20 to 60 mol %, more preferably from 30 to 60 mol %, based on all repeating units.

The fluorine group-containing resin can be synthesized by radical polymerization almost in the same manner as the alicyclic hydrocarbon-base acid decomposable resin.

The weight average molecular weight of the component (B) for use in the present invention is preferably from 1,000 to 200,000 in terms of polystyrene by GPC method. With a weight average molecular weight of 1,000 or more, the heat resistance and dry etching resistance can be increased and with a weight average molecular weight of 200,000 or less, the developability can be enhanced and at the same time, by virtue of very low viscosity, the film-forming property can be improved.

In the positive stimulus-sensitive composition of the present invention, the amount of the resin as the component (B) blended in the entire composition is preferably from 40 to 99.99 mass %, more preferably from 50 to 99.97 mass %, based on the entire solid content.

[3] (C) Dissolution Inhibiting Compound that Decomposes Under the Action of an Acid to Increase the Solubility in an Alkali Developer and having a Molecular Weight of 3,000 or Less (Hereinafter Sometimes Referred to as a "Component (C)" or "Dissolution Inhibiting Compound")

In order to prevent reduction in the transmittance at 220 nm or less, the dissolution inhibiting compound (C) of decomposing under the action of an acid to increase the solubility in an alkali developer and having a molecular weight of 3,000 or less is preferably an alicyclic or aliphatic compound containing an acid decomposable group, such as acid decomposable group-containing cholic acid derivative described in *Proceeding of SPIE*, 2724, 355 (1996). Examples of the acid decomposable group and the alicyclic structure are the same as those described above for the alicyclic hydrocarbon-base acid decomposable resin.

In the case where the stimulus-sensitive composition of the present invention is exposed with a KrF excimer laser or irradiated with electron beams, the dissolution inhibiting compound preferably contains a structure that a phenolic hydroxyl group of a phenol compound is displaced by an acid decomposable group. The phenol compound preferably contains from 1 to 9 phenol skeletons, more preferably from 2 to 6 phenol skeletons.

The molecular weight of the dissolution inhibiting compound, for use in the present invention is 3,000 or less, preferably from 300 to 3,000, more preferably from 500 to 2,500.

The amount of the dissolution inhibiting compound added is preferably from 3 to 50 mass %, more preferably from 5 to 40 mass %, based on the solid content of the stimulus-sensitive composition.

Specific examples of the dissolution inhibiting compound are set forth below, but the present invention is not limited thereto.

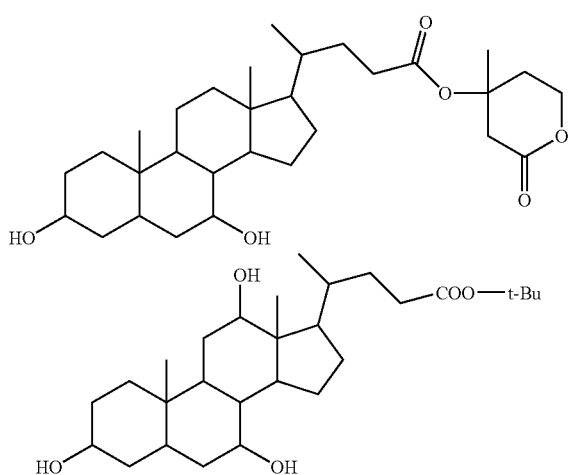

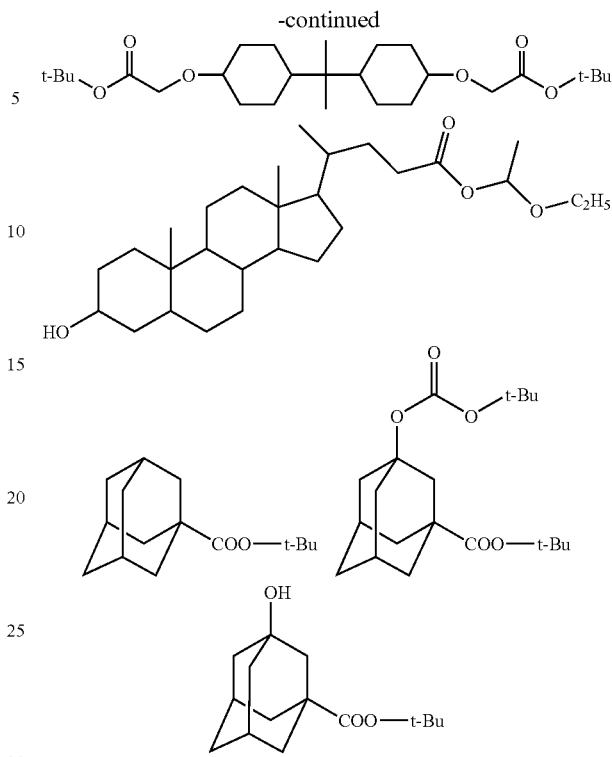

[4] (D) Resin Soluble in Alkali Developer (Hereinafter Sometimes Referred to as a "Component (D)" or "Alkali-soluble Resin")

The alkali dissolution rate of the alkali-soluble resin is preferably 20 Å/sec or more, more preferably 200 Å/sec or more (Å is angstrom), as measured (at 23° C.) in 0.261N tetramethylammonium hydroxide (TMAH).

Examples of the alkali-soluble resin for use in the present invention include, but are not limited to, novolak resin, hydrogenated novolak resin, acetone-pyrogallol resin, o-polyhydroxystyrene, m-polyhydroxystyrene, p-polyhydroxystyrene, hydrogenated polyhydroxystyrene, halogen- or alkyl-substituted polyhydroxystyrene, a hydroxystyrene-N-substituted maleimide copolymer, an o/p- or m/p-hydroxystyrene copolymer, polyhydroxystyrene with the hydroxyl group being partially O-alkylated (for example, 5 to 30 mol % being O-methylated, O-(1-methoxy)ethylated, O-2-tetrahydropyranylated or O-(tert-butoxycarbonyl)methylated) or O-acylated (for example, 5 to 30 mol % being o-acylated or O-tert-butoxy)carbonylated), a styrene-maleic anhydride copolymer, a styrene-hydroxystyrene copolymer, an α-methylstyrene-hydroxystyrene copolymer, a carboxyl group-containing methacrylic resin and a derivative thereof, and a polyvinyl alcohol derivative.

Among these alkali-soluble resins, preferred are novolak resin, o-polyhydroxystyrene, m-polyhydroxystyrene, p-polyhydroxystyrene, a copolymer thereof, alkyl-substituted polyhydroxystyrene, partially O-alkylated or O-acylated polyhydroxystyrene, a styrene-hydroxystyrene copolymer and an α-methylstyrene-hydroxystyrene copolymer.

The novolak resin can be obtained by subjecting predetermined monomers as main components and an aldehyde to addition condensation in the presence of an acidic catalyst.

The weight average molecular weight of the alkali-soluble resin is 2,000 or more, preferably from 5,000 to 200,000, more preferably from 5,000 to 100,000.

The weight average molecular weight used herein is defined as the value measured by gel permeation chromatography and calculated in terms of polystyrene.

In the present invention, these alkali-soluble resins (D) may be used in combination of two or more thereof.

The amount of the alkali-soluble resin used is from 40 to 97 mass %, preferably from 60 to 90 mass %, based on the entire solid content of the stimulus-sensitive composition.

[5] (E) Acid Crosslinking Agent that Cross-Links with the Alkali-soluble Resin by an Action of an Acid (Hereinafter Sometimes Referred to as a "Component (E)" or "Crosslinking Agent")

In the negative stimulus-sensitive composition of the present invention, a crosslinking agent is used.

The crosslinking agent may be any compound as long as it causes crosslinking of the resin soluble in an alkali developer under the action of an acid, but the following compounds (1) to (3) are preferred:

(1) hydroxymethyl, alkoxymethyl and acyloxymethyl forms of phenol derivative, (2) compounds having an N-hydroxymethyl group, an N-alkoxymethyl group or an N-acyloxymethyl group, and (3) compounds having an epoxy group.

The alkoxymethyl group is preferably an alkoxymethyl group having 6 or less carbon atoms and the acyloxymethyl group is preferably an acyloxymethyl group having 6 or less carbon atoms.

Among these crosslinking agent, particularly preferred are set forth below.

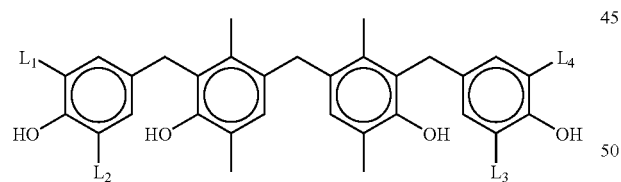

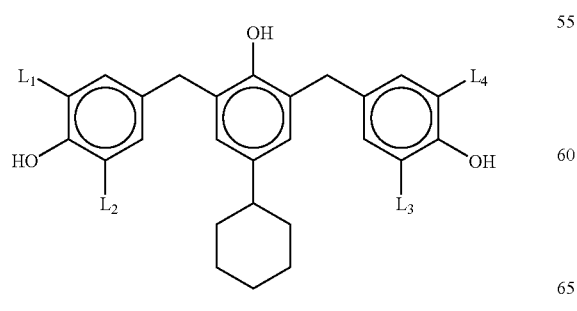

-continued

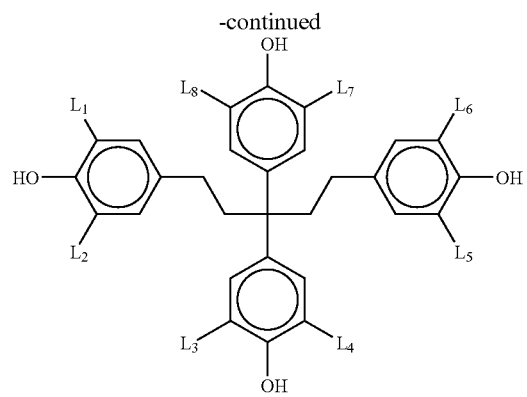

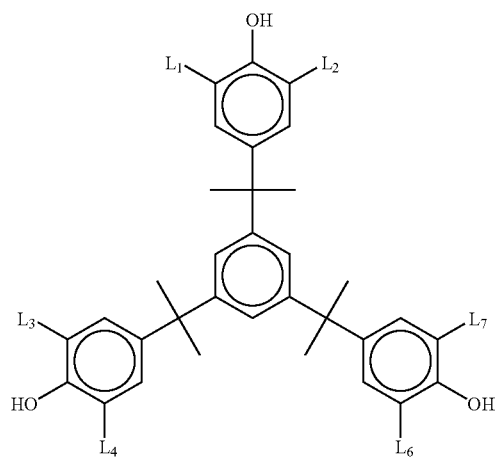

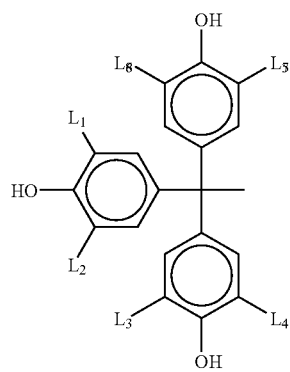

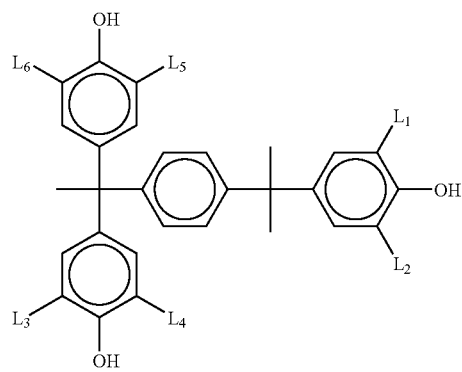

-continued

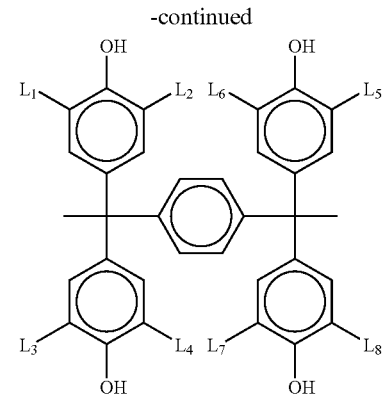

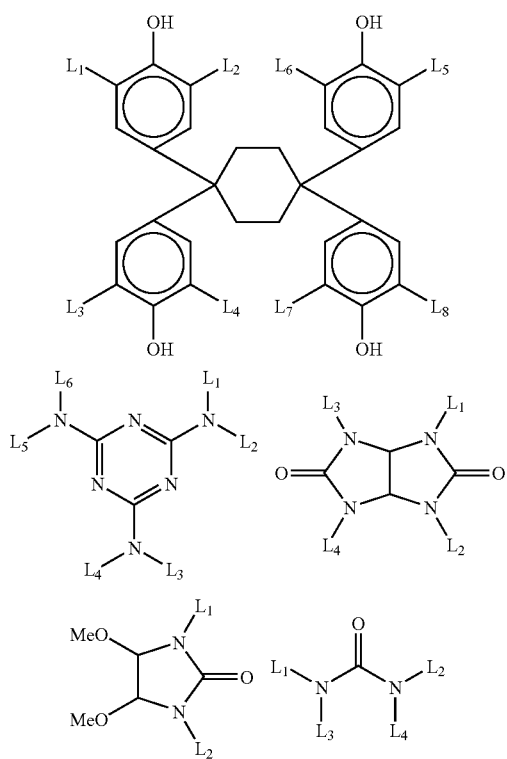

(wherein $L^1$ to $L^8$ may be the same or different and each represents a hydrogen atom, a hydroxymethyl group, a methoxymethyl group, an ethoxymethyl group or an alkyl group having from 1 to 6 carbon atoms).

The crosslinking agent is usually used in an amount of 3 to 70 mass %, preferably from 5 to 50 mass %, based on the solid content of the stimulus-sensitive composition.

<Other Components>

[6] (F) Basic Compound

The stimulus-sensitive composition of the present invention preferably contains (F) a basic compound so as to reduce the change of performance in aging from exposure to heating.

Preferred examples of the structure include structures represented by the following formulae (A) to (E):

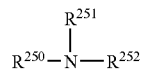

(A)

wherein $R^{250}$, $R^{251}$ and $R^{252}$ each independently represents a hydrogen atom, an alkyl group having from 1 to 20 carbon atoms or an aryl group having from 6 to 20 carbon atoms, and $R^{250}$ and $R^{251}$ may combine with each other to form a ring. The alkyl group may or may not have a substituent. The alkyl group having a substituent is preferably an aminoalkyl group having from 1 to 20 carbon atoms or a hydroxyalkyl group having from 1 to 20 carbon atoms.

These alkyl groups each may contain an oxygen atom, a sulfur atom or a nitrogen atom in the alkyl chain.

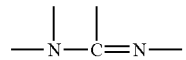

(B)

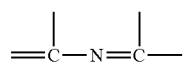

(C)

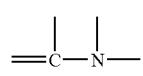

(D)

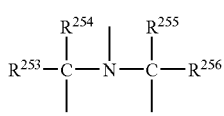

(E)

(wherein $R^{253}$, $R^{254}$, $R^{255}$ and $R^{256}$ each independently represents an alkyl group having from 1 to 6 carbon atoms).

Preferred examples of the compounds include a substituted or unsubstituted guanidine, a substituted or unsubstituted aminopyridine, a substituted or unsubstituted pyrazole, a substituted or unsubstituted pyrazoline, a substituted or unsubstituted piperazine, a substituted or unsubstituted aminomorpholine, a substituted or unsubstituted aminoalkylmorpholine and a substituted or unsubstituted piperidine, and more preferred examples of the compound include compounds having an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, and aniline derivatives having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]-octane, 1,5-diazabicyclo[4,3,0]non-5-ene and 1,8-diazabicyclo[5,4,0]undec-7-ene. Examples of the compound having an onium hydroxide structure include triaryl-sulfonium hydroxide, phenacylsulfonium hydroxide and sulfonium hydroxide having a 2-oxoalkyl group, specifically, triphenylsulfonium hydroxide, tris(tert-butylphenyl)-sulfonium hydroxide, bis(tert-butylphenyl)iodonium hydroxide, phenacylthiophenium hydroxide and 2-oxopropyl-thiphenium hydroxide. Examples of the compound having an onium carboxylate structure include the compounds having an onium hydroxide structure where the anion moiety is converted into a carboxylate, such as acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline and N,N-dimethylaniline. Examples of the alkylamine derivative having a hydroxyl group and/or an ether bond include ethanolamine, diethanolamine, triethanolamine and tris(methoxyethoxyethyl) amine. Examples of the aniline derivative having a hydroxyl group and/or an ether bond include N,N-bis(hydroxyethyl) aniline.

These basic compounds are used individually or in combination of two or more thereof. The amount of the basic compound used is usually from 0.001 to 10 mass %, preferably from 0.01 to 5 mass %, based on the solid content of the stimulus-sensitive composition. The amount used is preferably 0.001 mass % or more for obtaining sufficiently high addition effect and preferably 10 mass % or less in view of sensitivity and developability of unexposed area.

[7] (G) Surfactant Containing at least One of a Fluorine and a Silicon (Fluorine-containing and/or Silicon-containing Surfactant).

The stimulus-sensitive composition of the present invention preferably further contains a fluorine-containing and/or silicon-containing surfactant (any one of a fluorine-containing surfactant, a silicon-containing surfactant and a surfactant containing both a fluorine atom and a silicon atom, or two or more thereof).

When the stimulus-sensitive composition of the present invention contains a fluorine-containing and/or silicon-containing surfactant, a resist pattern with good sensitivity, resolution and adhesion and less development defects can be obtained on use of an exposure light source of 250 nm or less, particularly 220 nm or less.

Examples of the fluorine-containing and/or silicon-containing surfactant include surfactants described in JP-A-62-36663, JP-A-61-226746, JP-A-61-226745, JP-A-62-170950, JP-A-63-3.4540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include fluorine-containing surfactants and silicon-containing surfactants, such as EFtop EF301 and EF303 (produced by Shin-Akita Kasei K. K.), Florad FC430 and 431 (produced by Sumitomo 3M Inc.), Megafac F171, F173, F176, F189 and R08 (produced by Dainippon Ink & Chemicals, Inc.), Surflon S-382, SC101, 102, 103, 104, 105 and 106 (produced by Asahi Glass Co., Ltd.), and Troysol S-366 (produced by Troy Chemical). In addition, polysiloxane polymer KP-341 (produced by Shin-Etsu Chemical Co., Ltd.) may also be used as the silicon-containing surfactant.

Other than those known surfactants, surfactants using a polymer having a fluoro-aliphatic group, which is derived from a fluoro-aliphatic compound produced by telomerization (also called telomer process) or oligomerization (also called oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with (poly(oxyalkylene)) acrylate and/or (poly(oxyalkylene)) methacrylate and the polymer may have an irregular distribution or may be a block copolymer. Examples of the poly(oxyalkylene) group include a poly (oxyethylene) group, a poly(oxypropylene) group and a poly(oxybutylene group). This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxyalkylene)) acrylate (or methacrylate) may be not only a binary copolymer but also a ternary or greater copolymer comprising obtained by simultaneously copolymerizing two or more different fluoro-aliphatic group-containing monomers or two or more different (poly(oxyalkylene)) acrylates (or methacrylates).

Examples thereof include commercially available surfactants such as Megafac F178, F-470, F-473, F-475, F-476 and F-472 (produced by Dainippon Ink & Chemicals, Inc.), copolymers of an acrylate (or methacrylate) having $C_6F_{13}$ group and a (poly(oxyalkylene)) acrylate (or methacrylate), copolymers of an acrylate (or methacrylate) having $C_6F_{13}$ group, a (poly(oxyethylene)) acrylate (or methacrylate) and a (poly(oxypropylene)) acrylate (or methacrylate), copolymers of an acrylate (or methacrylate) having $C_8F_{17}$ group and a (poly(oxyalkylene)) acrylate (or methacrylate), and copolymers of an acrylate (or methacrylate) having $C_8F_{17}$ group, a (poly(oxyethylene)) acrylate (or methacrylate) and a (poly(oxypropylene)) acrylate (or methacrylate).

The amount of the fluorine-containing and/or silicon-containing surfactant used is preferably from 0.0001 to 2 mass %, more preferably from 0.001 to 1 mass %, based on the entire amount of the stimulus-sensitive composition (excluding the solvent).

[8] (H) Organic Solvent

In the stimulus-sensitive composition of the present invention, the above-described components are used by dissolving them in a predetermined organic solvent.

Examples of the organic solvent which can be used include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethylsulfoxide, N-methylpyrrolidone and tetrahydrofuran.

In the present invention, the organic solvents may be used individually or as a mixture thereof, but a mixed solvent obtained by mixing a solvent containing a hydroxyl group in the structure and a solvent not containing a hydroxyl group is preferably used. By using such a mixed solvent, the generation of particle during storage of the resist solution can be reduced.

Examples of the solvent containing a hydroxyl group include ethylene glycol, ethylene glycol monomethyl ether, ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent not containing a hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone, and butyl acetate are preferred, and propylene glycol monomethyl ether acetate, ethyl ethoxypropionate and 2-heptanone are most preferred.

The mixing ratio (by mass) of the solvent containing a hydroxyl group to the solvent not containing a hydroxyl group is from 1/99 to 99/1, preferably from 10/90 to 90/10, more preferably from 20/80 to 60/40. In view of the coating uniformity, a mixed solvent containing 50 mass % or more of a solvent not containing a hydroxyl group is particularly preferred.

<Other Additives>

The stimulus-sensitive composition of the present invention may further contain, if desired, a dye, a plasticizer, a surfactant other than the component (G), a photosensitizer and a compound which accelerates the solubility in a developer.

The compound which accelerates the dissolution in a developer, which can be used in the present invention, is a low molecular weight compound containing two or more phenolic OH groups or one or more carboxy group and having a molecular weight of 1,000 or less. In the case of containing a carboxyl group, an alicyclic or aliphatic compound is preferred.

The amount of the dissolution accelerating compound added is preferably from 2 to 50 mass %, more preferably from 5 to 30 mass %, based on the resin of component (B) or the resin of component (D). The amount added is preferably 50 mass % or less from the standpoint of preventing the development residue or deformation of pattern at the development.

The phenol compound having a molecular weight of 1,000 or less can be easily synthesized by one skilled in the art while referring to the method described, for example, in JP-A-4-122938, JP-A-2-28531, U.S. Pat. No. 4,916,210 and European Patent 219294.

Specific examples of the alicyclic or aliphatic compound having a carboxy group include, but are not limited to, carboxylic acid derivatives having a steroid structure, such as cholic acid, deoxycholic acid and lithocholic acid, adamantane carboxylic acid derivatives, an adamantane dicarboxylic acid, a cyclohexanecarboxylic acid and a cyclohexanedicarboxylic acid.

In the present invention, surfactants other than (G) the fluorine-containing and/or silicon-containing surfactant can also be added. Specific examples thereof include nonionic surfactants such as polyoxyethylene alkyl ethers, polyoxyethylene alkylallyl ethers, polyoxyethylene polyoxypropylene block copolymers, sorbitan fatty acid esters and polyoxyethylene sorbitan fatty acid esters.

One of these surfactants may be used alone or some of these surfactants may be used in combination.

<Use Method>

The, stimulus-sensitive composition of the present invention is used by dissolving the above-described components in a predetermined organic solvent, preferably a mixed solvent described above, and coating the obtained solution on a predetermined support as follows.

For example, the stimulus-sensitive composition is coated on a substrate (e.g., silicon/silicon dioxide-coated substrate) as used in the production of precision integrated circuit elements, by an appropriate coating method such as spinner or coater.

After the coating, the obtained film is subjected to irradiation with an actinic ray through a predetermined mask and developed by baking, whereby a good pattern can be obtained. Examples of the actinic ray include infrared light, visible light, ultraviolet light far ultraviolet light, X ray and electron beam. Among these, preferred are far ultraviolet light at a wavelength of 250 nm or less, more preferably 220 nm or less, specifically, KrF excimer laser (248 nm), ArF excimer laser (193 nm), $F_2$ excimer laser (157 nm), X ray and electron beam, and most preferred are ArF excimer laser and $F_2$ excimer laser. Incidentally, in the present invention, X ray and electron beam are included in the actinic ray.

In the development step, an alkali developer is used as follows. The alkali developer which can be used for the resist composition is an alkaline aqueous solution of an inorganic alkali such as sodium hydroxide, potassium hydroxide, sodium carbonate, sodium silicate, sodium metasilicate and aqueous ammonia, a primary amine such as ethylamine and n-propylamine, a secondary amine such as diethylamine and di-n-butylamine, a tertiary amine such as triethylamine and methyldiethylamine, an alcohol amine such as dimethyl-ethanolamine and triethanolamine, a quaternary ammonium salt such as tetramethylammonium hydroxide and tetraethylammonium hydroxide, or a cyclic amine such as pyrrole and piperidine.

In the alkali developer, alcohols and surfactant may be added in an appropriate amount.

The alkali concentration of the alkali developer is usually from 0.1 to 20 mass %.

The pH of the alkali developer is usually from 10.0 to 15.0.

EXAMPLES

The present invention is described in greater detail below by referring to Examples, but the present invention should not be construed as being limited thereto.

<Synthesis Example of Compound (A)>

Synthesis Example 1

Synthesis of Compound (I-1)):

Phenacyl bromide (13.0 g) and 21.2 g of methyl thiodipropionate were dissolved in 150 ml of acetonitrile and thereto, 12.7 g of silver tetrafluoroborate was added. The resulting mixed solution was reacted under reflux for 5 hours and the reaction solution was filtered to remove silver compound. The filtrate was concentrated and thereto, 100 ml of chloroform/hexane=1/1 was added. The powder precipitated was collected by filtration and dried to obtain 26 g of phenacyl-bis(methoxycarbonylethyl)sulfonium tetrafluoroborate.

The obtained tetrafluoroborate (15 g) was dissolved in 100 ml of chloroform and thereto, 12.9 g of potassium nonafluorobutanesulfonate dissolved in a water/acetonitrile mixed solvent was added. The reaction solution was subjected to liquid separation and the chloroform phase was washed with water and concentrated to obtain 20.3 g of Compound (I-1).

300 MHz $^1$H-NMR (CDCl$_3$):

δ3.15 (m. 4H), δ3.7 (s. 6H), δ3.9 (t. 4H), δ5.7 (s. 2H), δ7.5 (t. 2H), δ7.65 (t. 1H), δ8.0 (d. 2H)

<Synthesis of Resin (B)>

Synthesis Example 1

Synthesis of Resin (1) (Side Chain Type)):

2-Ethyl-2-adamantyl methacrylate and butyrolactone methacrylate were charged at a ratio of 55/45 and dissolved in methyl ethyl ketone/tetrahydrofuran=5/5 to prepare 100 mL of a solution having a solid concentration of 20%. To this solution, 2 mol % of V-65 produced by Wako Pure Chemical Industries, Ltd. was added and the resulting solution was added dropwise to 10 mL of methyl ethyl ketone heated at 60° C., over 4 hours in a nitrogen atmosphere. After the completion of dropwise addition, the reaction solution was heated for 4 hours, 1 mol % of V-65 was again added thereto and the resulting solution was stirred for 4 hours. After the completion of reaction, the reaction solution was cooled to room temperature and crystallized in 3 L of a distilled water/ISO propyl alcohol (=1/1) mixed solvent and Resin (1) as the precipitated white powder was recovered.

The polymer composition ratio determined from $C^{13}$NMR was 46/54. The mass average molecular weight in terms of standard polystyrene as determined by GPC was 10,700.

Resins (2) to (12) and (26) to (31) were synthesized in the same manner as in Synthesis Example 1.

Synthesis Example 2

Synthesis of Resin (13) (Main Chain Type)

Into a separable flask, tert-butyl norbornenecarboxylate, butyrolactone norbornenecarboxylate and maleic anhydride (molar ratio: 40/10/50) and also THF (reaction temperature, 60 mass %) were charged and heated at 60° C. in a nitrogen stream. When the reaction temperature was stabilized, 2 mol % of radical initiator V-601 produced by Wako Pure Chemical Industries, Ltd. was added to initiate the reaction. After heating for 12 hours, the obtained reaction mixture was 2-fold diluted with tetrahydrofuran and then charged into a mixed solution of hexane/isopropyl alcohol=1/1 to precipitate white powder. The precipitated powder was collected by filtration and dried to obtain the objective Resin (13).

The molecular weight of Resin (13) obtained was analyzed by GPC and found to be 8,300 (mass average) in terms of polystyrene. Also, by NMR spectrum, the molar ratio of tert-butyl norbornenecarboxylate/butyrolactone norbornenecarboxylate/malic anhydride repeating units in Resin (1) was confirmed to be 42/8/50.

Resins (14) to (19) were synthesized in the same manner as in Synthesis Example 2.

Synthesis Example 3

Synthesis of Resin (20) (Hybrid Type)):

Norbornene, maleic anhydride, tert-butyl acrylate and 2-methylcyclohexyl-2-propyl acrylate at a molar ratio of 35/35/20/10 were charged into a reactor and dissolved in tetrahydrofuran to prepare a solution having a solid content of 60%. This solution was heated at 65° C. in a nitrogen stream. When the reaction temperature was stabilized, 1 mol % of radical initiator V-601 produced by Wako Pure Chemical Industries, Ltd. was added to initiate the reaction. After heating for 8 hours, the obtained reaction mixture was 2-fold diluted with tetrahydrofuran and then charged into a 5-fold volume of hexane to precipitate white powder. The precipitated powder was collected by filtration, dissolved in methyl ethyl ketone and-re-precipitated in a 5-fold volume of hexane/tert-butyl methyl ether (=1/1) mixed solvent. The white powder precipitated was collected by filtration and dried to obtain the objective Resin (20).

The molecular weight of Resin (20) obtained was analyzed by GPC and found to be 12,100 (mass average) in terms of polystyrene. Also, by NMR spectrum, the molar ratio of norbornene/maleic anhydride/tert-butyl acrylate/2-methylcyclohexyl-2-propyl acrylate in the composition of Resin (1) was found to be 32/39/19/10.

Resins (21) to (25) were synthesized in the same manner as in Synthesis Example 3.

The structure and molecular weight of each of Resins (1) to (31) are shown below.

-continued
| | Molecular Weight |
|---|---|
| (3) 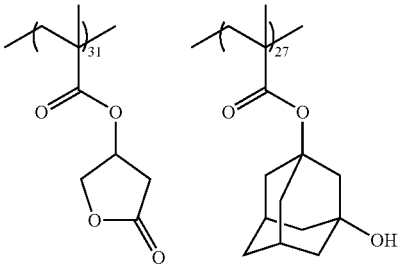 | 8300 |
| (4) 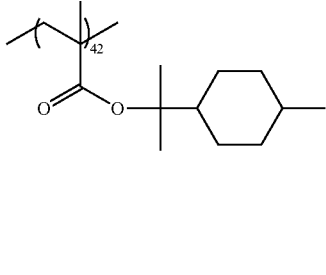 | 10300 |
| (5) 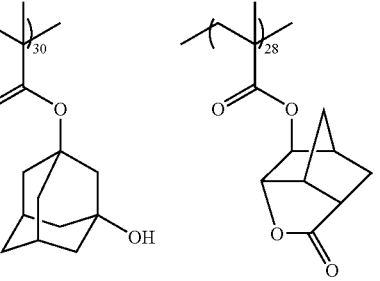 | 8900 |
| (6) 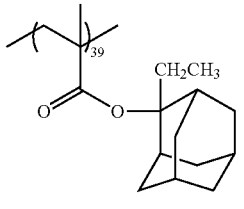 | 11300 |
| (7) 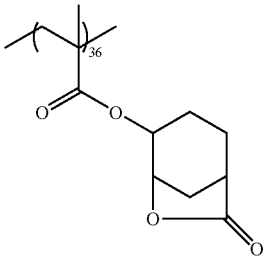 | 8900 |

| | Molecular Weight |
|---|---|
| (8) | 11700 |
| (9) | 9800 |
| (10) | 8700 |
| (11) | 13400 |
| (12) | 10900 |

| | Molecular Weight |
|---|---|
| (13) | 8300 |
| (14) | 8200 |
| (15) | 9600 |
| (16) | 5800 |
| (17) | 4700 |
| (18) | 8500 |
| (19) | 8900 |

-continued

| | Molecular Weight |
|---|---|
| (20) | 12100 |
| (21) | 13900 |
| (22) | 12400 |
| (23) | 12700 |
| (24) | 10800 |
| (25) | 9300 |

-continued

| | Molecular Weight |
|---|---|
| (26) | 9300 |
| (27) | 7600 |
| (28) | 7300 |
| (29) | 7600 |
| (30) | 8400 |

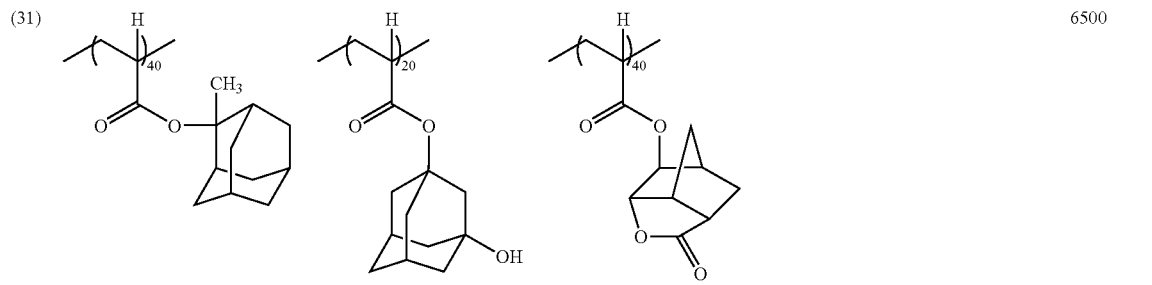
(31)    Molecular Weight 6500
<Fluorine Group-Containing Resin>
Structures of Fluorine Group-Containing Resins (FII-1) to (FII-40) used in Examples are shown below.
Also, the weight average molecular weight and the like of each of Fluorine Group-Containing Resins (FII-1) to (FII-40) are shown in Tables 1 and 2 below.
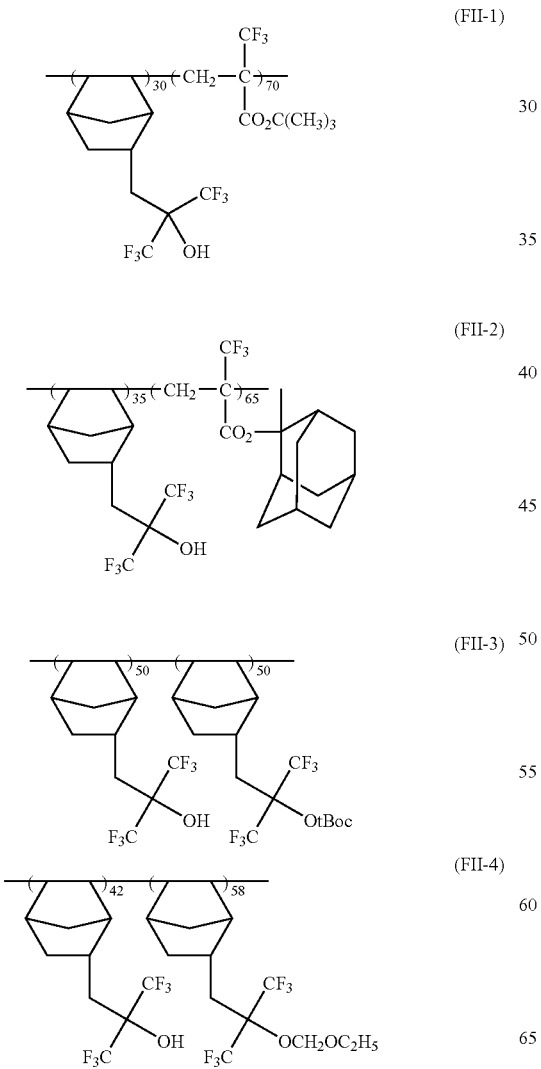
(FII-1)
(FII-2)
(FII-3)
(FII-4)
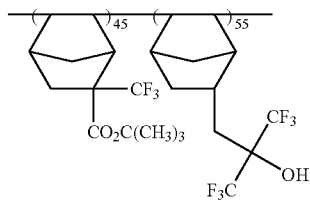
(FII-5)
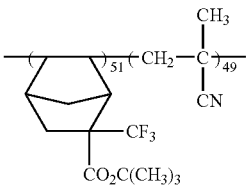
(FII-6)
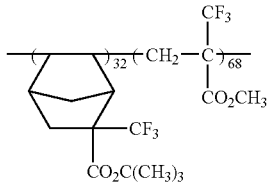
(FII-7)
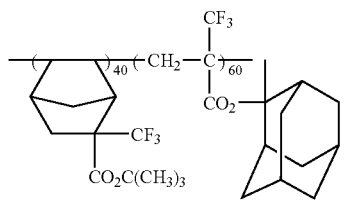
(FII-8)
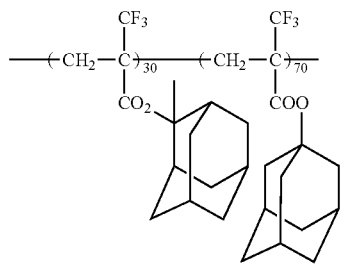
(FII-9)

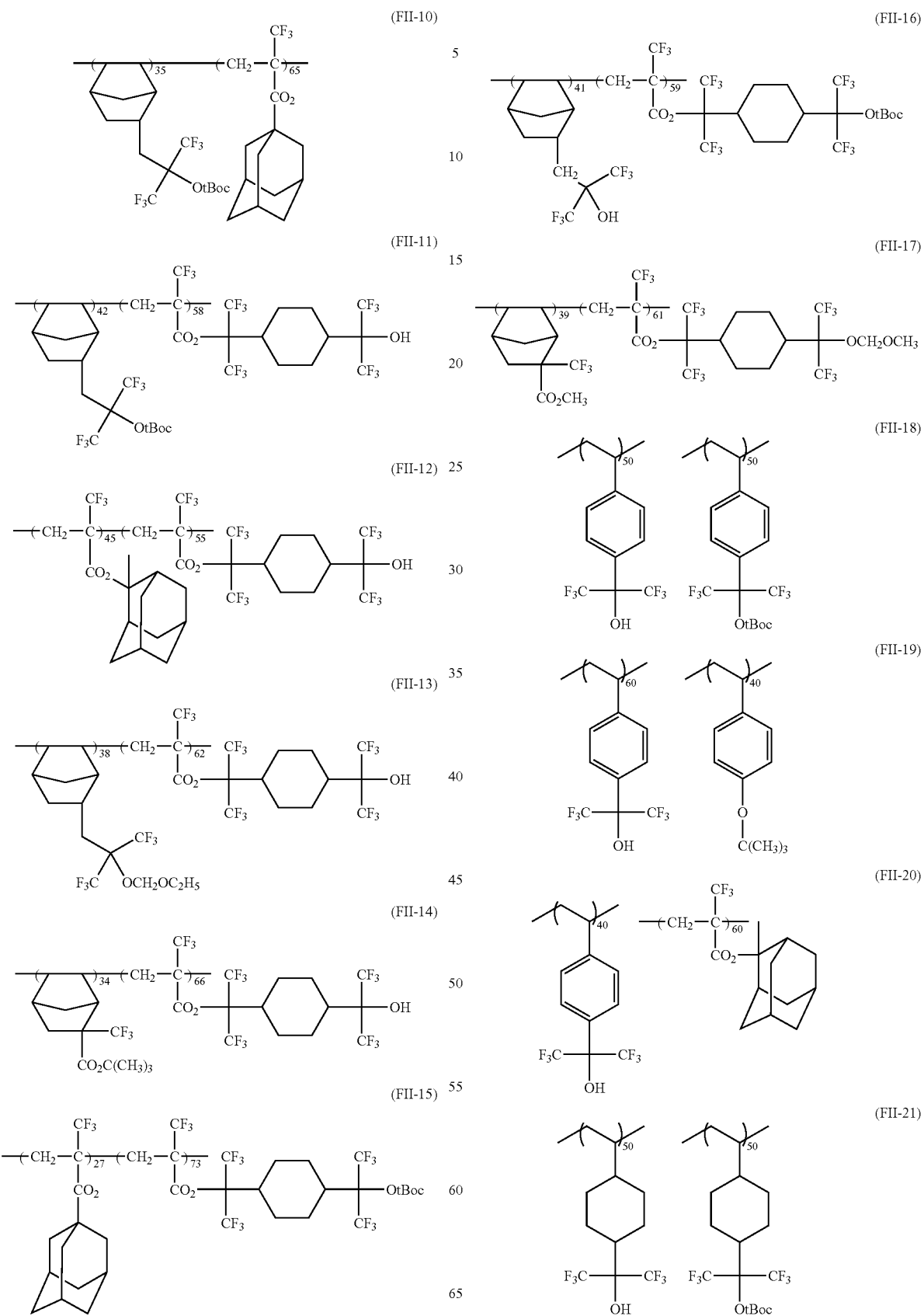

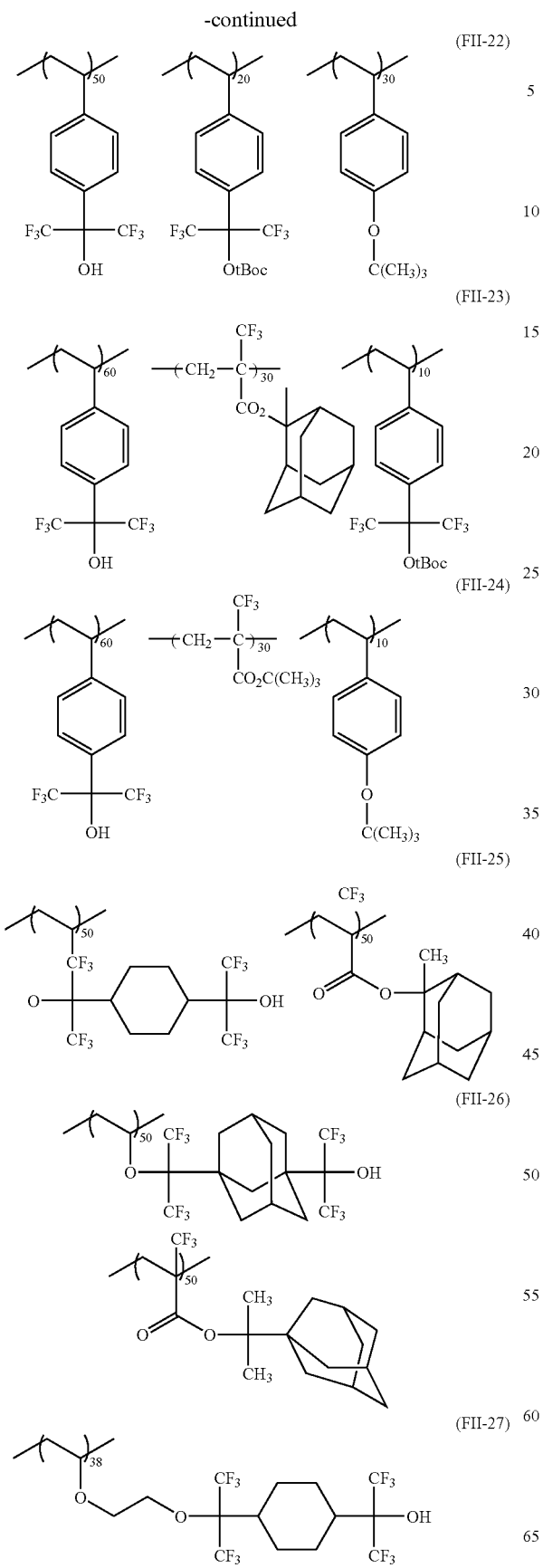
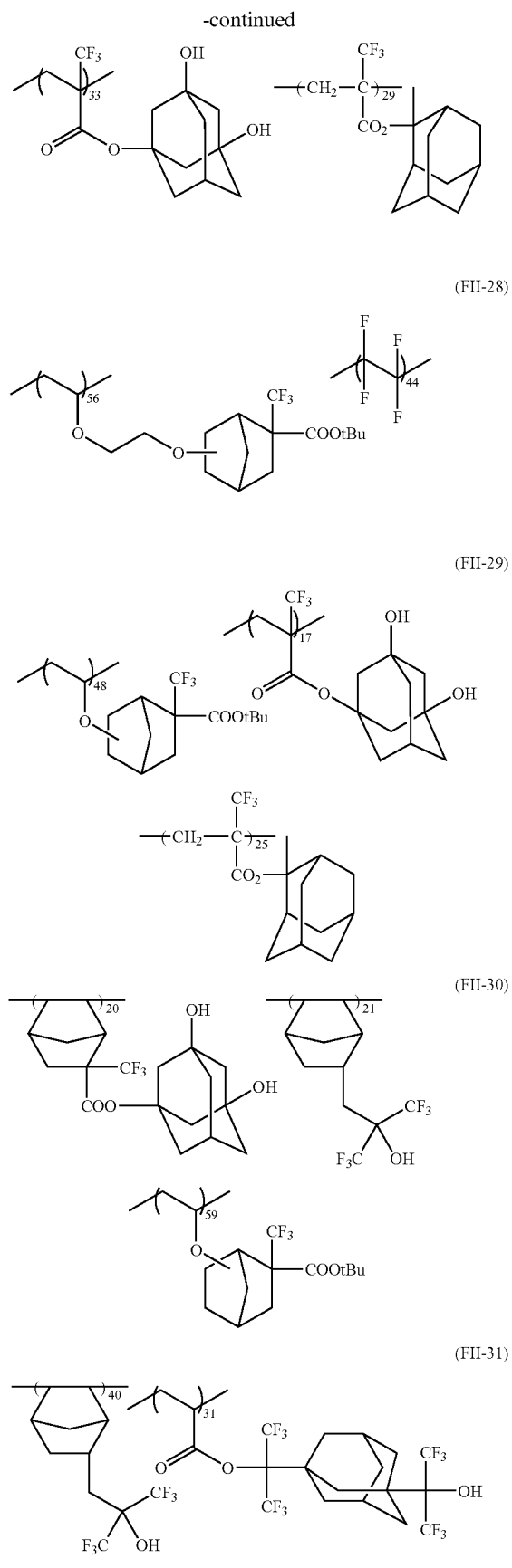

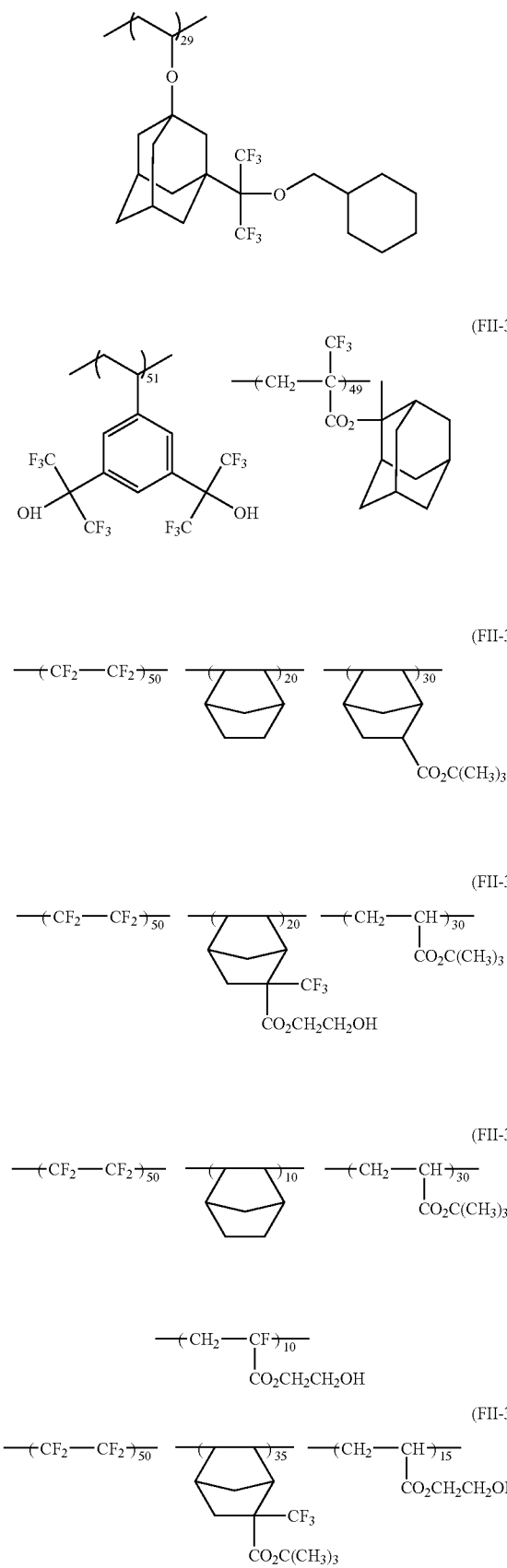
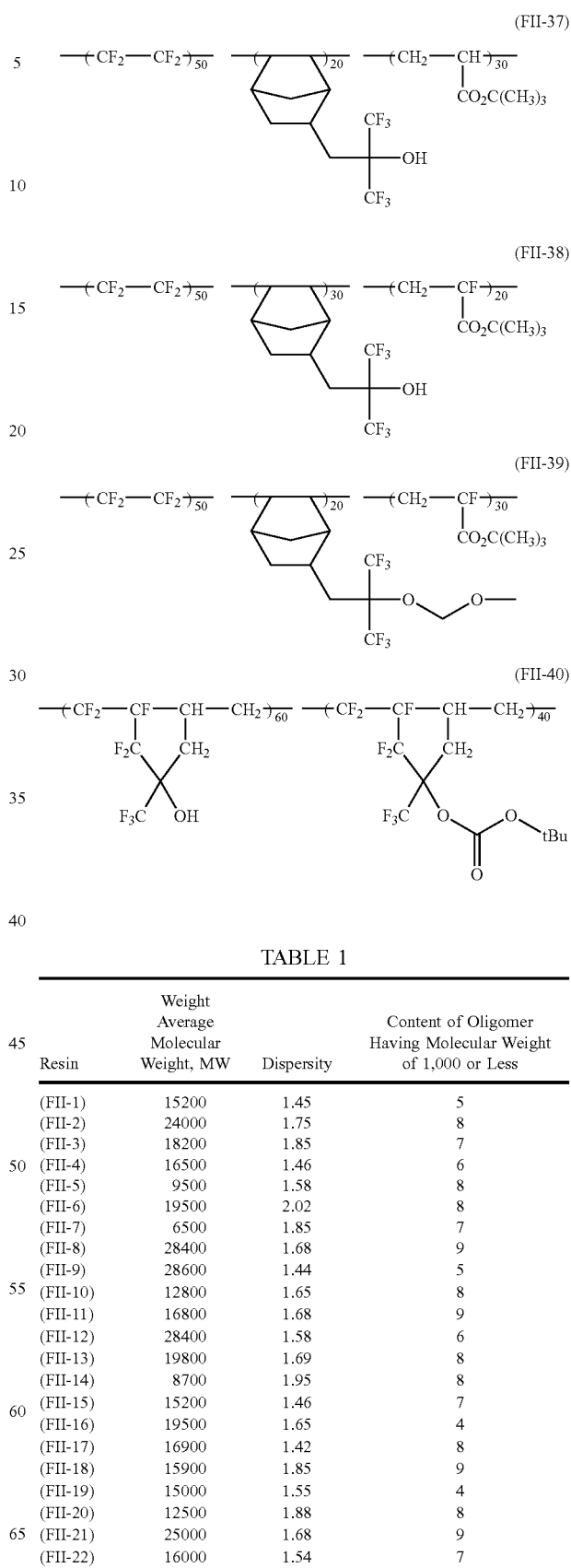
TABLE 1
| Resin | Weight Average Molecular Weight, MW | Dispersity | Content of Oligomer Having Molecular Weight of 1,000 or Less |
|---|---|---|---|
| (FII-1) | 15200 | 1.45 | 5 |
| (FII-2) | 24000 | 1.75 | 8 |
| (FII-3) | 18200 | 1.85 | 7 |
| (FII-4) | 16500 | 1.46 | 6 |
| (FII-5) | 9500 | 1.58 | 8 |
| (FII-6) | 19500 | 2.02 | 8 |
| (FII-7) | 6500 | 1.85 | 7 |
| (FII-8) | 28400 | 1.68 | 9 |
| (FII-9) | 28600 | 1.44 | 5 |
| (FII-10) | 12800 | 1.65 | 8 |
| (FII-11) | 16800 | 1.68 | 9 |
| (FII-12) | 28400 | 1.58 | 6 |
| (FII-13) | 19800 | 1.69 | 8 |
| (FII-14) | 8700 | 1.95 | 8 |
| (FII-15) | 15200 | 1.46 | 7 |
| (FII-16) | 19500 | 1.65 | 4 |
| (FII-17) | 16900 | 1.42 | 8 |
| (FII-18) | 15900 | 1.85 | 9 |
| (FII-19) | 15000 | 1.55 | 4 |
| (FII-20) | 12500 | 1.88 | 8 |
| (FII-21) | 25000 | 1.68 | 9 |
| (FII-22) | 16000 | 1.54 | 7 |

TABLE 1-continued

| Resin | Weight Average Molecular Weight, MW | Dispersity | Content of Oligomer Having Molecular Weight of 1,000 or Less |
|---|---|---|---|
| (FII-23) | 14600 | 1.95 | 5 |
| (FII-24) | 17500 | 1.48 | 5 |
| (FII-25) | 16500 | 1.52 | 6 |
| (FII-26) | 14600 | 1.63 | 5 |

TABLE 2

| Resin | Weight Average Molecular Weight, Mw | Dispersity |
|---|---|---|
| (FII-27) | 8300 | 1.55 |
| (FII-28) | 8300 | 1.62 |
| (FII-29) | 8000 | 1.52 |
| (FII-30) | 9200 | 1.71 |
| (FII-31) | 10200 | 1.47 |
| (FII-32) | 7900 | 1.35 |
| (FII-33) | 6800 | 1.60 |
| (FII-34) | 7400 | 1.59 |

TABLE 2-continued

| Resin | Weight Average Molecular Weight, Mw | Dispersity |
|---|---|---|
| (FII-35) | 8300 | 1.70 |
| (FII-36) | 4800 | 1.55 |
| (FII-37) | 4700 | 1.51 |
| (FII-38) | 6400 | 1.69 |
| (FII-39) | 9600 | 1.70 |
| (FII-40) | 4600 | 1.68 |

Examples 1 to 30 and Comparative Example 1

<Preparation of Resist>

The components shown in Tables 3 to 6 below were dissolved in a solvent to prepare a solution having a solid concentration of 12 mass % and this solution was filtered through a 0.1-μm polytetrafluoroethylene filter or polyethylene filter to prepare a positive resist solution. The prepared positive resist solutions were evaluated by the following methods and the results are shown in Tables 3 to 6.

TABLE 3

| | Acid Generator (g) | Acid Generator Used in Combination (g) | Resin | Basic Compound (g) | Surfactant (0.03 g) | Solvent (mass ratio) | Component (C) (g) | Sensitivity (mJ/cm$^2$) | Profile |
|---|---|---|---|---|---|---|---|---|---|
| Example 1 | I-1 (0.04) | — | (1) 10 g | DBN (0.02) | W-1 | A1 = 100 | — | 16.3 | ○ |
| Example 2 | I-3 (0.04) | z40 (0.03) | (2) 10 g | TMEA (0.02) | W-1 | A1 = 100 | — | 19.7 | ○ |
| Example 3 | I-12 (0.03) | z38 (0.04) | (3) 10 g | TPSA (0.02) | W-2 | A1 = 100 | — | 18.2 | ○ |
| Example 4 | I-11 (0.03) | — | (4) 10 g | HEP (0.01) | W-2 | A3/B1 (80/20) | — | 15.7 | ○ |
| Example 5 | I-9 (0.05) | — | (5) 10 g | TOA (0.03) | W-3 | A2/B1 (90/10) | — | 17.2 | ○ |
| Example 6 | I-54 (0.05) | z5 (0.02) z44 (0.02) | (6) 10 g | TBAH (0.01) | W-3 | A4/B1 (90/10) | LCB (1) | 15.8 | ○ |
| Example 7 | I-4 (0.04) | z14 (0.02) | (7) 10 g | TPA (0.007) | W-4 | A1/B1 (50/50) | — | 19.2 | ○ |
| Example 8 | I-29 (0.05) | z38 (0.02) | (8) 10 g | DBN (0.02) | W-4 | A1/B1 (90/10) | — | 16.6 | ○ |
| Example 9 | I-5 (0.05) | — | (9) 10 g | TPI (0.03) | W-1 | A5/B2 (90/10) | — | 15.4 | ○ |
| Example 10 | I-18 (0.05) | z27 (0.02) z49 (0.03) | (10) 5 g (13) 5 g | TPI (0.02) | W-1 | A1/B1 (95/5) | — | 19.4 | ○ |

TABLE 4

| | Acid Generator (g) | Acid Generator Used in Combination (g) | Resin | Basic Compound (g) | Surfactant (0.03 g) | Solvent (mass ratio) | Component (C) (g) | Sensitivity (mJ/cm$^2$) | Profile |
|---|---|---|---|---|---|---|---|---|---|
| Example 11 | I-48 (0.02) | z15 (0.02) z31 (0.005) | (11) 5 g (14) 5 g | DIA (0.02) | W-2 | A1/B1 (90/10) | — | 17.7 | ○ |
| Example 12 | I-21 (0.05) | z38 (0.02) | (12) 6 g (15) 4 g | DIA (0.01) HAP (0.01) | W-2 | A1/B1 (95/5) | — | 15.8 | ○ |
| Example 13 | I-2 (0.03) | — | (16) 10 g | TPI (0.03) | W-3 | A1/B1 (95/5) | — | 17.5 | ○ |
| Example 14 | I-56 (0.02) | — | (17) 10 g | DBN (0.02) | W-3 | A1/B1 (95/5) | — | 16.8 | ○ |
| Example 15 | I-38 (0.04) | z16 (0.01) z34 (0.01) | (18) 3 g (31) 7 g | DIA (0.02) | W-4 | A1/B1 (80/20) | — | 15.3 | ○ |
| Example 16 | I-6 (0.03) | z13 (0.01) z24 (0.04) | (19) 10 g | TPA (0.01) | W-4 | A1 = 100 | — | 17.8 | ○ |
| Example 17 | I-50 (0.02) | z38 (0.02) | (20) 10 g | TPA (0.03) | W-4 | A1 = 100 | — | 18.3 | ○ |
| Example 18 | I-57 (0.03) | — | (21) 10 g | DCMA (0.01) | W-4 | A1 = 100 | — | 16.3 | ○ |
| Example 19 | I-47 (0.04) | — | (22) 10 g | TPI (0.02) | W-4 | A1/B1 (95/5) | — | 15.7 | ○ |
| Example 20 | I-46 (0.03) | z38 (0.015) z41 (0.03) | (26) 5 g (23) 5 g | TPI (0.03) | W-4 | A1/B1 (95/5) | — | 18.2 | ○ |

TABLE 5

| | Acid Generator (g) | Acid Generator Used in Combination (g) | Resin | Basic Compound (g) | Surfactant (0.03 g) | Solvent (mass ratio) | Component (C) (g) | Sensitivity (mJ/cm$^2$) | Profile |
|---|---|---|---|---|---|---|---|---|---|
| Example 21 | I-16 (0.01) | z5 (0.02) z4 (0.005) | (27) 5 g (24) 5 g | DBN (0.02) | W-1 | A1/B1 (95/5) | — | 17.8 | ○ |
| Example 22 | I-7 (0.005) | z44 (0.02) z14 (0.01) | (28) 5 g (25) 5 g | DIA (0.01) HAP (0.01) | W-1 | A1/B1 (80/20) | — | 15.8 | ○ |
| Example 23 | I-53 (0.03) | z38 (0.015) z50 (0.02) | (29) 10 g | TPSA (0.02) | W-2 | A1/B1 (90/10) | — | 17.3 | ○ |
| Example 24 | I-52 (0.05) | — | (30) 10 g | HEP (0.01) | W-2 | A3/B2 (80/20) | — | 16.5 | ○ |
| Example 25 | I-12 (0.06) | — | (31) 10 g | DIA (0.02) | W-3 | A2/B1 (90/10) | — | 17.2 | ○ |

TABLE 6

| | Acid Generator (g) | Acid Generator Used in Combination (g) | Resin | Basic Compound (g) | Surfactant (0.03 g) | Solvent (mass ratio) | Component (C) (g) | Sensitivity (mJ/cm$^2$) | Profile |
|---|---|---|---|---|---|---|---|---|---|
| Example 26 | I-59 (0.05) | z14 (0.3) | (28) 10 g | DIA (0.03) | W-4 | A1/B1 (60/40) | — | 14.3 | ○ |
| Example 27 | I-60 (0.1) | z14 (0.2) Z50 (0.3) | (4) 5 g (29) 5 g | DIA (0.015) PEA (0.015) | W-4 | A1/A5 (60/40) | — | 14.6 | ○ |
| Example 28 | I-59 (0.1) I-63 (0.3) | Z40 (0.1) Z44 (0.1) | (30) 5 g (11) 5 g | DIA (0.02) PEA (0.015) | W-4 | A1/A5 (40/60) | — | 14.2 | ○ |
| Example 29 | I-59 (0.2) | Z5 (0.1) Z6 (0.1) | (28) 10 g | DIA (0.02) | W-4 | A1/B1 (40/60) | — | 15.0 | ○ |
| Example 30 | I-59 (0.1) | z1 (0.1) z36 (0.4) | (31) 10 g | DIA (0.03) | W-4 | A1/B1 (60/40) | — | 14.5 | ○ |
| Comparative Example 1 | PAG-A (0.04) | — | (1) 10 g | DBN (0.02) | W-1 | A1 = 100 | — | 22.0 | Δ |

Abbreviations in Tables are as follows. The resins and acid generators not shown below are already exemplified above. In each Table, when multiple resins or solvents are used, the ratio is a ratio by mass.

[Acid Generator]

PAG-A:

[Basic Compound]
DBN: 1,5-diazabicyclo[4.3.0]-non-5-ene
TPI: 2,4,5-triphenylimidazole
TPSA: triphenylsulfonium acetate
HEP: N-hydroxyethylpiperidine
DIA: 2,6-diisopropylaniline
DCMA: dicyclohexylmethylamine
TPA: tripentylamine
TOA: tri-n-octylamine
HAP: hydroxyantipyrine
TBAH: tetrabutylammonium hydroxide
TMEA: tris(methoxyethoxyethyl)amine
PEN: N-phenyldiethanolamine

[Surfactant]
W-1: Megafac F176 (produced by Dainippon Ink & Chemicals, Inc.) (fluorine-containing surfactant)
W-2: Megafac R08 ((produced by Dainippon Ink & Chemicals, Inc.) (fluorine/silicon-containing surfactant)
W-3: polysiloxane polymer KP-341 (produced by Shin-Etsu Chemical Co., Ltd.) (silicon-containing surfactant)
W-4: Troysol S-366 (produced by Troy Chemical)

[Solvent]
A1: propylene glycol methyl ether acetate
A2: 2-heptanone
A3: ethyl ethoxypropionate
A4: γ-butyrolactone
A5: cyclohexanone
B1: propylene glycol methyl ether
B2: ethyl lactate

[Dissolution Inhibitor]
LCB: tert-butyl lithocholate

<Evaluation of Resist>

On a silicon wafer treated with hexamethyl-disilazane, an antireflective film DUV-42 produced by Brewer Science Co., Ltd. was uniformly coated by a spin coater to a thickness of 600 Å, dried on a hot plate at 100° C. for 90 seconds, and then dried by heating at 190° C. for 240 seconds. Thereafter, each positive resist solution was coated by spin coater and dried at 120° C. for 90 seconds to form a resist film of 0.30 μm.

The formed resist film was exposed by an ArF excimer laser stepper (manufactured by ISI, NA=0.6) and immediately after the exposure, heated on a hot plate at 120° C. for 90 seconds. Thereafter, the resist film was developed with an aqueous 2.38% tetramethylammonium hydroxide solution at 23° C. for 60 seconds, rinsed with pure water for 30 seconds and dried to obtain a line pattern.

(1) Sensitivity

The sensitivity indicates a minimum exposure amount of reproducing a mask pattern of 1/1 line-and-space pattern of 0.15 μm.

(2) Profile

The profile of lines in the 1/1 line-and-space of 0.15 μm was observed by a scanning microscope. A rectangular profile was rated ○, a profile having a slightly tapered shape or a slightly skirt-like shape was rated Δ, and a profile having a completely tapered shape or a completely skirt-like shape was rated X.

As apparent from Tables 3 to 6, the positive resist compositions of Examples 1 to 30 exhibit high sensitivity and excellent pattern profile.

Examples 31 to 33 and Comparative Example 2

(1) Formation of Lower Resist Layer

FHi-028DD Resist (resist for i-line, produced by Fujifilm Olin Co., Ltd.) was coated on a 6-inch silicon wafer by using spin coater Mark 8 manufactured by Tokyo Electron Ltd. and then baked at 90° C. for 90 seconds to obtain a uniform film having a thickness of 0.55 μm.

This film was further heated at 200° C. for 3 minutes to form a lower resist layer having a thickness of 0.40 μm.

(2) Formation of Upper Resist Layer

The components shown in Table 7 below were dissolved in a solvent to prepare a solution having a solid concentration of 11 mass % and this solution was microfiltered through a membrane filter having a pore size of 0.1 μm to prepare an upper resist composition.

The prepared upper resist composition was coated on the lower resist layer in the same manner and heated at 130° C. for 90 seconds to form an upper resist layer having a thickness of 0.20 μm.

TABLE 7

| | Acid Generator (g) | Acid Generator Used in Combination (g) | Resin | Basic Compound (g) | Surfactant (0.03 g) | Solvent (mass ratio) | Component (C) (g) | Sensitivity (mJ/cm$^2$) | Profile |
|---|---|---|---|---|---|---|---|---|---|
| Example 31 | I-1 (0.04) | z5 (0.02) z44 (0.02) | SI-1 | DIA (0.02) PEA (0.02) | W-4 | A1/B1 (60/40) | — | 15.8 | ○ |
| Example 32 | I-5 (0.04) | z14 (0.02) | SI-2 PEA (0.02) | DIA (0.02) | W-4 | A1/B1 (60/40) | — | 19.3 | ○ |
| Example 33 | I-54 (0.06) | z38 (0.02) | SI-3 | DIA (0.02) PEA (0.02) | W-4 | A1/B1 (60/40) | — | 17.5 | ○ |
| Comparative Example 2 | PAG-A (0.04) | z5 (0.02) z44 (0.02) | SI-1 | DIA (0.02) PEA (0.02) | W-4 | A1/B1 (60/40) | — | 20.3 | X |

Resins (SI-1) to (SI-3) in Table 7 are shown below.

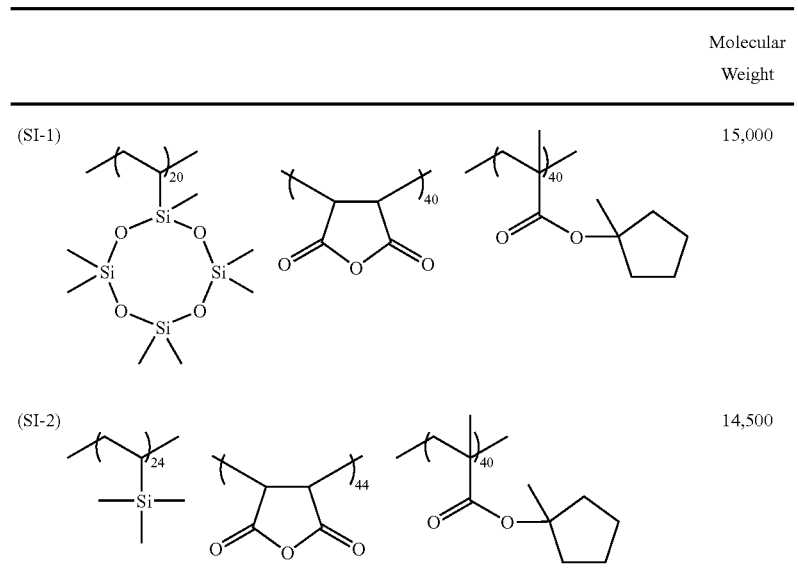

| | | Molecular Weight |
|---|---|---|
| (SI-3) | 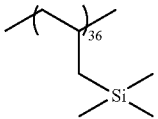 | 9,600 |

(3) Evaluation of Resist

The wafer obtained above was exposed by an ArF excimer laser stepper 9300 (manufactured by ISI) having mounted thereon a resolution mask, while changing the exposure amount.

Subsequently, the wafer was heated at 120° C. for 90 seconds, developed with a tetrahydroammonium hydroxide developer (2.38 mass %) for 60 seconds, rinsed with distilled water and dried to obtain an upper layer pattern.

The thus-obtained resist pattern of silicon wafer was observed by SEM and the resist was evaluated as follows.

Assuming that the sensitivity is an exposure amount of reproducing a 180-nm isolated contact hole in 130 nm, the pattern profile at this exposure amount was observed through a scanning microscope. A rectangular profile was rated ○, a profile having a slightly tapered shape or a slightly skirt-like shape was rated Δ, and a profile having a completely tapered shape or a completely skirt-like shape was rated X. The evaluation results are shown in Table 6. As apparent from Table 6, the positive resist compositions of Examples 31 to 33 exhibit high sensitivity and excellent pattern profile.

Examples 34 to 53 and Comparative Example 3

<Preparation of Resist>

The components shown in Tables 8 and 9 below were dissolved in a solvent and the resulting solution was filtered through a 0.1-μm polytetrafluoroethylene filter to prepare a positive resist solution.

<Evaluation of Resist>

On a silicon wafer treated with hexamethyl-disilazane, each positive resist solution was coated by a spin coater and dried on a vacuum contact-type hot plate at 120° C. for 90 seconds to obtain a resist film having a thickness of 0.1 μm.

The obtained resist film was exposed by using a 157-nm laser exposure/dissolution behavior analyzer VUVES-4500 (manufactured by Litho Tech Japan Corp.) and immediately after the exposure, heated on a hot plate at 120° C. for 90 seconds. Thereafter, the resist film was developed with an aqueous 2.38 mass % tetramethylammonium hydroxide solution for 60 seconds and rinsed with pure water to obtain a sample wafer. Using these wafers, the exposure amount (sensitivity) for resolving a large pattern was determined. The results are shown in Tables 8 and 9.

TABLE 8

| | Acid Generator (g) | Acid Generator Used in Combination (g) | Resin | Basic Compound (g) | Surfactant (0.03 g) | Solvent (mass ratio) | Sensitivity (mJ/cm²) |
|---|---|---|---|---|---|---|---|
| Example 34 | I-1 (0.04) | — | FII-1 (10) | DIA (0.05) | W-1 | A1 (130) | 4.3 |
| Example 35 | I-3 (0.04) | z40 (0.03) | FII-2 (10) | TPI (0.04) | W-1 | A1 (80) B2 (40) | 2.5 |
| Example 36 | I-12 (0.03) | z38 (0.04) | FII-8 (8) FII-33 (2) | TOA (0.04) | W-2 | A1 (125) B1 (5) | 5.3 |
| Example 37 | I-11 (0.03) | — | FII-11 (4) FII-34 (6) | HEP (0.06) | W-2 | A1 (100) B1 (40) | 3.2 |
| Example 38 | I-9 (0.05) | — | FII-12 (3) FII-35 (7) | DBN (0.05) | W-3 | A1 (110) B2 (40) | 4.7 |
| Example 39 | I-54 (0.05) | z5 (0.02) z44 (0.02) | FII-13 (10) | DIA (0.04) PEA (0.04) | W-1 | A1 (80) B1 (70) | 3.8 |
| Example 40 | I-4 (0.04) | z14 (0.02) | FII-14 (9) FII-39 (1) | TPA (0.04) | W-2 | A1 (90) B2 (60) | 5.8 |
| Example 41 | I-29 (0.05) | z38 (0.02) | FII-16 (10) | TPSA (0.1) | W-4 | A1 (70) B2 (40) | 5.2 |
| Example 42 | I-5 (0.05) | — | FII-18 (5) FII-1 (5) | TBAH (0.03) | W-1 | A1 (80) B2 (30) | 3.5 |
| Example 43 | I-18 (0.03) | z27 (0.02) z49 (0.03) | FII-20 (5) FII-5 (5) | TMEA (0.05) | W-1 | A1 (80) B1 (70) | 4.3 |

TABLE 9

| | Acid Generator (g) | Acid Generator Used in Combination (g) | Resin | Basic Compound (g) | Surfactant (0.03 g) | Solvent (mass ratio) | Sensitivity (mJ/cm$^2$) |
|---|---|---|---|---|---|---|---|
| Example 44 | I-48 (0.02) | z15 (0.02) z31 (0.005) | FII-27 (5) FII-32 (5) | HAP (0.05) | W-1 | A1 (150) | 2.7 |
| Example 45 | I-21 (0.05) | z38 (0.02) | FII-28 (5) FII-27 (5) | DBN (0.04) | W-2 | A2 (70) B1 (80) | 4.3 |
| Example 46 | I-2 (0.03) | — | FII-29 (8) FII-3 (2) | DIA (0.01) PEA (0.01) | W-1 | A1 (100) B2 (60) | 5.8 |
| Example 47 | I-56 (0.02) | — | FII-30 (2) FII-31 (5) | PEA (0.05) | W-1 | A1 (110) B1 (70) | 3.3 |
| Example 48 | I-38 (0.04) | z1.6 (0.01) z34 (0.01) | FII-38 (10) | TPI (0.04) | W-1 | A1 (80) B2 (40) | 5.2 |
| Example 49 | I-6 (0.03) | z13 (0.01) z24 (0.04) | FII-40 (5) F11-1 (5) | TOA (0.04) | W-2 | A1 (125) A3 (5) | 2.8 |
| Example 50 | I-50 (0.02) | z38 (0.02) | FII-19 (3) FII-28 (7) | HEP (0.06) | W-2 | A1 (100) B1 (40) | 4.5 |
| Example 51 | I-57 (0.03) | — | FII-11 (5) F11-3 (5) | DBN (0.03) | W-3 | A1 (110) B2 (40) | 5.3 |
| Example 52 | I-47 (0.04) | — | FII-32 (4) FII-30 (6) | DIA (0.04) PEA (0.04) | W-1 | A1 (80) B1 (70) | 3.6 |
| Example 53 | I-46 (0.03) | z38 (0.015) z41 (0.03) | FII-5 (7) FII-28 (3) | TPA (0.04) | W-2 | A1 (90) B2 (60) | 4.2 |
| Comparative Example 3 | PAG-A (0.04) | — | FII-1 (10) | DIA (0.05) | W-1 | A1 (130) | 10.2 |

As apparent from Tables 8 and 9, the positive resist compositions of Examples 34 to 53 exhibit excellent sensitivity.

In Examples above, ArF excimer laser light and $F_2$ excimer laser light were used as the actinic ray, but the same results were obtained also when the exposure was performed by using KrF excimer laser light or electron beam.

The stimulus-sensitive composition of the present invention is estimated to exert the same effects also for EUV light.

According to the present invention, a stimulus-sensitive composition exhibiting high sensitivity and excellent profile, a compound for use in the stimulus-sensitive composition, and a pattern forming method using the stimulus-sensitive composition can be provided.

The entire disclosure of each and every foreign patent application from which the benefit of foreign priority has been claimed in the present application is incorporated herein by reference, as if fully set forth.

What is claimed is:

1. A stimulus-sensitive composition comprising a compound that generates one of an acid and a radical by external stimulation, the compound being represented by formula (I'):

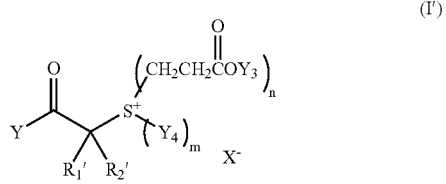

wherein Y represents an aryl group, an alkyl group, a cycloalkyl group, an alkenyl group, a —C(=O)—$Y_{3a}$ group or a —$Y_{3b}$—C(=O)—$Y_{3c}$ group, wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group, wherein $R_3$ and $R_4$ each independently represents a hydrogen atom, an alkyl group or a cycloalkyl group, and $Y_{3b}$ represents a divalent linking group resulting from removal of one hydrogen atom from the $Y_{3a}$, $R_1'$ and $R_2'$ each independently represents a hydrogen atom, an alkyl group or a cycloalkyl group, $Y_3$ and $Y_4$ each independently represents an alkyl group or a cycloalkyl group, $X^-$ represents a non-nucleophilic anion, m represents 0 or 1, and n represents 1 or 2, provided that m+n=2.

2. A pattern forming method comprising:

forming a resist film by using the stimulus-sensitive composition according to claim 1; and exposing and developing the resist film.

3. The stimulus-sensitive composition according to claim 1, further comprising at least one of (F) a basic compound and (G) a surfactant containing at least one of a fluorine and a silicon.

4. The stimulus-sensitive composition according to claim 3, wherein (F) the basic compound is one of (i) a compound having a structure selected from an imidazole structure, a diazabicyclo structure, an onium hydroxide structure, an onium carboxylate structure, a trialkylamine structure, an aniline structure and a pyridine structure, (ii) an alkylamine derivative having at least one of a hydroxyl group and an ether bond, and (iii) an aniline derivative having at least one of a hydroxyl group and an ether bond.

5. A compound represented by formula (I'):

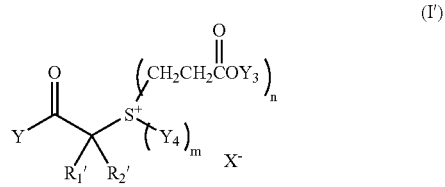

wherein Y represents an aryl group, an alkyl group, a cycloalkyl group, an alkenyl group, a —C(=O)—$Y_{3a}$ group or a —$Y_{3b}$—C(=O)—$Y_{3c}$ group, wherein $Y_{3a}$ and $Y_{3c}$ each represents an alkyl group, a cycloalkyl group, an aryl group, an alkenyl group, an alkoxy group, an aryloxy group, a hydroxyl group, a —$NR_3R_4$ group, a —NHC(=O)—$R_3$ group or a —$NHSO_2R_3$ group, wherein $R_3$ and $R_4$ each independently represents a hydrogen atom, an alkyl group or a cycloalkyl group, and $Y_{3b}$ represents a divalent linking group resulting from removal of one hydrogen atom from the $Y_{3a}$, $R_1'$ and $R_2'$ each independently represents a hydrogen atom, an alkyl group or a cycloalkyl group, $Y_3$ and $Y_4$ each independently represents an alkyl group or a cycloalkyl group, $X^-$ represents a non-nucleophilic anion, m represents 0 or 1, and n represents 1 or 2, provided that m+n=2.

6. A positive stimulus-sensitive composition comprising:
    (A) a compound that generates an acid upon irradiation with an actinic ray, according to claim 4; and
    (B) a resin that increases a solubility of the resin in an alkali developer by an action of an acid.

7. The positive stimulus-sensitive composition according to claim 6, wherein the resin (B) has a fluorine atom in the main or side chain.

8. The positive stimulus-sensitive composition according to claim 6, wherein the resin (B) has a hexafluoro-isopropanol structure.

9. The positive stimulus-sensitive composition according to claim 6, wherein the resin (B) has a hydroxystyrene structure.

10. The positive stimulus-sensitive composition as according to claim 6, wherein the resin (B) has a monocyclic or polycyclic alicyclic hydrocarbon structure.

11. The positive stimulus-sensitive composition according to claim 10, wherein the resin (B) further has a lactone structure.

12. The positive stimulus-sensitive composition according to claim 6, further comprising (C) a dissolution inhibiting compound that increases a solubility of the compound (C) by an action of an acid, the compound (C) having a molecular weight of 3,000 or less.

13. A positive stimulus-sensitive composition comprising:
    (A) a compound that generates an acid upon irradiation with an actinic ray, according to claim 4;
    (D) a resin soluble in an alkali developer; and
    (C) a dissolution inhibiting compound that increases a solubility of the compound (C) by an action of an acid, the compound (C) having a molecular weight of 3,000 or less.

14. A negative stimulus-sensitive composition comprising:
    (A) a compound that generates an acid upon irradiation with an actinic ray, according to claim 4;
    (D) a resin soluble in an alkali developer; and
    (E) an acid crosslinking agent that cross-links with the alkali developer-soluble resin by an action of an acid.

* * * * *